(12) United States Patent
Kawamura et al.

(10) Patent No.: US 9,688,913 B2
(45) Date of Patent: Jun. 27, 2017

(54) LIQUID CRYSTAL COMPOSITION, LIQUID CRYSTAL DISPLAY DEVICE, AND LIQUID CRYSTAL DISPLAY

(71) Applicant: DIC CORPORATION, Tokyo (JP)

(72) Inventors: Joji Kawamura, Kita-adachi-gun (JP); Masahiro Niwa, Kita-adachi-gun (JP); Makoto Negishi, Kita-adachi-gun (JP)

(73) Assignee: DIC CORPORATION, Tokyo (JP)

( * ) Notice: Subject to any disclaimer, the term of this patent is extended or adjusted under 35 U.S.C. 154(b) by 0 days.

(21) Appl. No.: 14/394,883

(22) PCT Filed: Mar. 5, 2013

(86) PCT No.: PCT/JP2013/055948
§ 371 (c)(1),
(2) Date: Oct. 16, 2014

(87) PCT Pub. No.: WO2014/136202
PCT Pub. Date: Sep. 12, 2014

(65) Prior Publication Data
US 2015/0361343 A1    Dec. 17, 2015

(51) Int. Cl.
*C09K 19/34* (2006.01)
*C09K 19/20* (2006.01)
(Continued)

(52) U.S. Cl.
CPC .......... *C09K 19/3402* (2013.01); *C07C 13/28* (2013.01); *C07C 25/18* (2013.01);
(Continued)

(58) Field of Classification Search
CPC ............ C09K 19/0466; C09K 19/3402; C09K 2019/3004; C09K 2019/3025; C09K 2019/3422
See application file for complete search history.

(56) References Cited

U.S. PATENT DOCUMENTS 6,210,603 B1 * 4/2001 Kondo .................... C07C 17/12
   252/299.6
8,617,419 B2 * 12/2013 Ohgiri ..................... C09K 19/32
   252/299.01
(Continued)

FOREIGN PATENT DOCUMENTS

JP        2009-185285 A    8/2009

OTHER PUBLICATIONS

Written opinion of PCT/JP2013/055948 dated Apr. 16, 2013 (6 pages).

*Primary Examiner* — Cynthia H Kelly
*Assistant Examiner* — Anna Malloy
(74) *Attorney, Agent, or Firm* — Westerman, Hattori, Daniels & Adrian, LLP

(57) ABSTRACT

A liquid crystal composition includes one or more of compounds represented by general formula (i) below and one or more of compounds represented by general formula (ii) below.
In the formulae, $R^{11a}$ and $R^{21a}$ each independently represent an alkyl group having 1 to 8 carbon atoms where one —$CH_2$— or two or more non-adjacent —$CH_2$— in the alkyl group may each independently be substituted with —CH=CH—, —C≡C—, —O—, —CO—, —COO—, or —OCO—; one or more hydrogen atoms in the alkyl group may be substituted with a fluorine atom or a chlorine atom; $X^{11a}$, $X^{12a}$, $X^{13a}$, $X^{14a}$, and $X^{21a}$ each independently represent a hydrogen atom or a fluorine atom; $A^{21a}$, $A^{22a}$, and $A^{23a}$ each independently represent a trans-1,4-cyclohexylene group or a 1,4-phenylene group whose hydrogen atom may be substituted with a fluorine atom or a chlorine atom.

[Chem. 1]

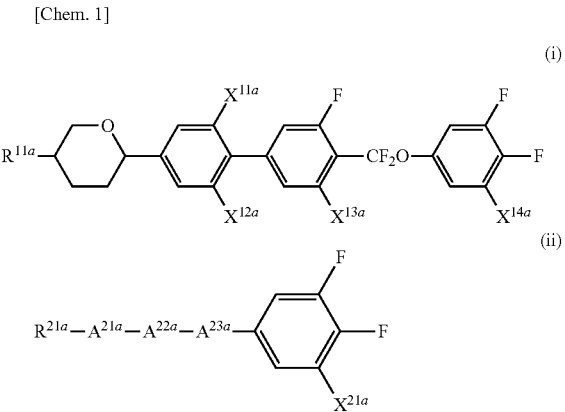

17 Claims, 1 Drawing Sheet

(51) Int. Cl.
  *C09K 19/30* (2006.01)
  *C09K 19/42* (2006.01)
  *C07C 13/28* (2006.01)
  *C07C 25/18* (2006.01)
  *C07C 43/225* (2006.01)
  *C07C 69/753* (2006.01)
  *C07D 309/06* (2006.01)
  *C09K 19/02* (2006.01)
  *G02F 1/1339* (2006.01)
  *C09K 19/04* (2006.01)
  *G02F 1/1341* (2006.01)
  *G02F 1/137* (2006.01)
  *C09K 19/12* (2006.01)

(52) U.S. Cl.
  CPC ......... *C07C 43/225* (2013.01); *C07C 69/753* (2013.01); *C07D 309/06* (2013.01); *C09K 19/0216* (2013.01); *C09K 19/20* (2013.01); *C09K 19/3066* (2013.01); *C09K 19/42* (2013.01); *C07C 2101/14* (2013.01); *C09K 2019/0466* (2013.01); *C09K 2019/123* (2013.01); *C09K 2019/124* (2013.01); *C09K 2019/301* (2013.01); *C09K 2019/3004* (2013.01); *C09K 2019/3019* (2013.01); *C09K 2019/3025* (2013.01); *C09K 2019/3422* (2013.01); *G02F 1/1339* (2013.01); *G02F 1/13394* (2013.01); *G02F 2001/13398* (2013.01); *G02F 2001/13415* (2013.01); *G02F 2001/13706* (2013.01)

(56) References Cited

U.S. PATENT DOCUMENTS

| | | |
|---|---|---|
| 2009/0194739 A1 | 8/2009 | Wittek et al. |
| 2012/0141694 A1 | 6/2012 | Matsumoto et al. |
| 2012/0256124 A1* | 10/2012 | Ohgiri .................... C09K 19/32 252/299.61 |

\* cited by examiner

LIQUID CRYSTAL COMPOSITION, LIQUID CRYSTAL DISPLAY DEVICE, AND LIQUID CRYSTAL DISPLAY

TECHNICAL FIELD

The present invention relates to a nematic liquid crystal composition with a positive dielectric anisotropy (Δ∈) which is useful as a liquid crystal display material, and to a liquid crystal display device and a liquid crystal display using the nematic liquid crystal composition.

BACKGROUND ART

Liquid crystal display devices are used in watches, calculators, various measuring instruments, automobile panels, word processors, electronic notepads, printers, computers, televisions, clocks, advertizing boards, and the like. Representative examples of liquid crystal display modes include a TN (twisted nematic) mode, an STN (super twisted nematic) mode, a vertical alignment mode that uses TFTs (thin film transistors), and an IPS (in-plane switching) mode. The liquid crystal compositions used in these liquid crystal display devices are required to be stable against outer factors such as moisture, air, heat, and light, have a liquid crystal phase in a temperature range as wide as possible about room temperature, have a low viscosity, and operate at a low drive voltage. A liquid crystal composition is constituted by several to several tens of compounds in order to optimize, for example, the dielectric anisotropy (Δ∈) and/or the refractive index anisotropy (Δn) for individual liquid crystal display devices.

In vertical alignment (VA) mode displays, a liquid crystal composition having negative Δ∈ is used. In horizontal alignment mode displays such as TN mode, STN mode, and IPS (in-plane switching) mode displays, a liquid crystal composition having positive Δ∈ is used. A drive system in which display is conducted by vertically aligning a liquid crystal composition having positive Δ∈ when no voltage is applied and by applying a transverse electric field has also been reported. This further increases the demand for liquid crystal compositions having positive Δ∈. In all drive systems, low-voltage driving, high-speed response, and a wide operating temperature range are required. That is, it is required that the absolute value of positive Δ∈ is high, the viscosity (η) is low, and the nematic phase-isotropic liquid phase transition temperature (Tni) is high. Furthermore, to control Δn×d, which is a product of Δn and cell gap (d), to be a desired value, Δn of the liquid crystal composition needs to be adjusted in an appropriate range in accordance with the cell gap. In addition, since an importance is given to high-speed response when liquid crystal display devices are applied to televisions or the like, a liquid crystal composition having a low rotational viscosity ($\gamma_1$) is demanded.

For example, a liquid crystal composition that contains a liquid crystal compound having positive Δ∈ and represented by formula (A-1) below or formula (A-2) below and a liquid crystal compound having neutral Δ∈ and represented by formula (B) below in a combined manner has been disclosed as a liquid crystal composition with the aim of achieving high-speed response. The features of such a liquid crystal composition are that the liquid crystal compound having positive Δ∈ has a —CF$_2$O— structure and the liquid crystal compound having neutral Δ∈ has an alkenyl group. These features are well-known in the field of liquid crystal compositions (refer to PTLs 1 to 4).

[Chem. 1]

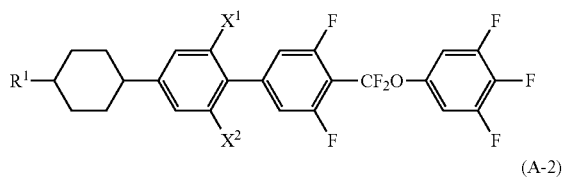

(A-1)

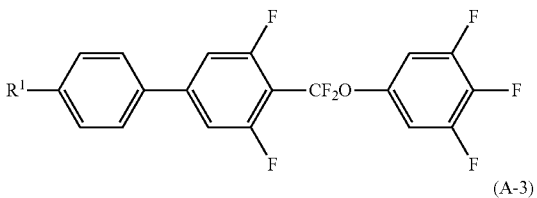

(A-2)

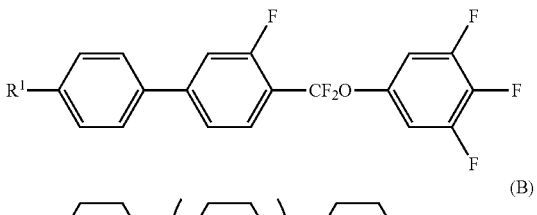

(A-3)

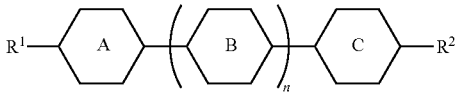

(B)

With the increasing number of applications of liquid crystal display devices, methods of using the liquid crystal display devices and methods of producing the liquid crystal display devices have also been markedly changed. In order to catch up with these changes, it has been desired to optimize properties other than known basic physical properties. Specifically, regarding liquid crystal display devices that use a liquid crystal composition, VA mode liquid crystal display devices, IPS mode liquid crystal display devices, and the like have been widely used, and very large display devices having a 50-inch or larger display size have been practically used. Regarding a method for injecting a liquid crystal composition into a substrate, with the increase in the substrate size, a one-drop-fill (ODF) method has been mainly used instead of an existing vacuum injection method. However, it has been found that a drop mark formed when a liquid crystal composition is dropped onto a substrate results in a problem of a decrease in the display quality. Furthermore, in the production process of liquid crystal display devices by the ODF method, an optimum amount of liquid crystal needs to be dropped in accordance with the size of a liquid crystal display device. If the amount of liquid crystal dropped highly deviates from the optimum amount, the predesigned balance of the refractive index and driving electric field of the liquid crystal display device is lost, which causes display defects such as formation of spots and contrast defects. In particular, in small-size liquid crystal display devices heavily used for fashionable smart phones, the optimum amount of liquid crystal dropped is small and thus it is difficult to control the deviation from the optimum amount within a particular range. Therefore, to maintain a high production yield of the liquid crystal display device, for example, it is necessary that the liquid crystal composition is less affected by a sudden change in pressure in a dropping device and an impact that occur when liquid crystal is dropped and thus the liquid crystal composition can be continuously dropped in a stable manner for a long time.

As described above, liquid crystal compositions used for active-matrix driving liquid crystal display devices that are driven with a TFT device and the like need to be developed in consideration of a method for producing a liquid crystal display device in addition to properties such as high specific resistance, high voltage holding ratio, and stability against outer factors, e.g., light and heat, to which an importance has been conventionally given, while maintaining the properties and performance required for liquid crystal display devices, such as high-speed response.

CITATION LIST

Patent Literature

PTL 1: Japanese Unexamined Patent Application Publication No. 2008-037918
PTL 2: Japanese Unexamined Patent Application Publication No. 2008-038018
PTL 3: Japanese Unexamined Patent Application Publication No. 2010-275390
PTL 4: Japanese Unexamined Patent Application Publication No. 2011-052120

SUMMARY OF INVENTION

Technical Problem

It is an object of the present invention to provide a liquid crystal composition which has positive $\Delta\epsilon$, has a liquid crystal phase over a wide temperature range, has a low viscosity, has high solubility at low temperature, has a high specific resistance and a high voltage holding ratio, is stable against heat and light, and does not easily cause display defects such as image sticking and drop marks and with which a liquid crystal display device having high display quality can be produced at a high yield; and also to provide a liquid crystal display device that uses the liquid crystal composition.

Solution to Problem

The inventors of the present invention have studied various liquid crystal compounds and various chemical substances and have found that the object can be achieved by combining particular liquid crystal compounds to each other. Thus, the present invention has been completed. That is, the first aspect of the present invention is a liquid crystal composition below, the second aspect of the present invention is a liquid crystal device below, and the third aspect of the present invention is a liquid crystal display below.

[1] A liquid crystal composition contains one or more of compounds represented by general formula (i) below and one or more of compounds represented by general formula (ii) below.

[Chem. 2]

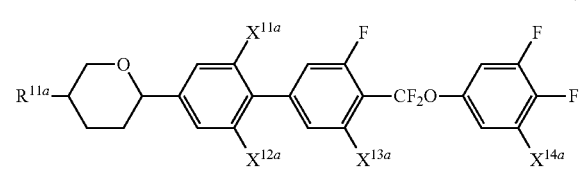

(i)

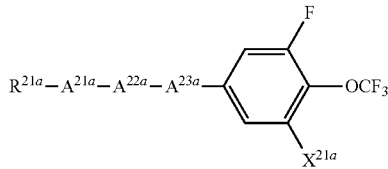

(ii)

(In the formulae, $R^{11a}$ and $R^{21a}$ each independently represent an alkyl group having 1 to 8 carbon atoms where one —$CH_2$— or two or more non-adjacent —$CH_2$— in the alkyl group may each independently be substituted with —CH=CH—, —C≡C—, —O—, —CO—, —COO—, or —OCO—; one or more hydrogen atoms in the alkyl group may be substituted with a fluorine atom or a chlorine atom; $X^{11a}$, $X^{12a}$, $X^{13a}$, $X^{14a}$, and $X^{21a}$ each independently represent a hydrogen atom or a fluorine atom; $A^{11a}$, $A^{22a}$, and $A^{23a}$ each independently represent a trans-1,4-cyclohexylene group or a 1,4-phenylene group whose hydrogen atom may be substituted with a fluorine atom or a chlorine atom.)

[2] In the liquid crystal composition according to [1], $X^{11a}$ and $X^{12a}$ in the general formula (i) each represent a hydrogen atom.

[3] In the liquid crystal composition according to [1] or [2], $X^{13a}$ in the general formula (i) represents a fluorine atom.

[4] In the liquid crystal composition according to any one of [1] to [3], $X^{14a}$ in the general formula (i) represents a fluorine atom.

[5] In the liquid crystal composition according to any one of [1] to [4], $A^{23a}$ in the general formula (ii) represents a 1,4-phenylene group, two hydrogen atoms that bond to the 1,4-phenylene group being substituted with fluorine atoms.

[6] In the liquid crystal composition according to any one of [1] to [5], $X^{21a}$ in the general formula (ii) represents a hydrogen atom.

[7] In the liquid crystal composition according to any one of [1] to [6], the compounds represented by the general formula (ii) correspond to a compound represented by formula (39.2) below.

[Chem. 3]

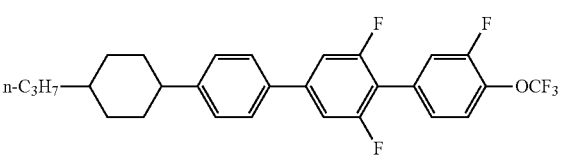

(39.2)

[8] The liquid crystal composition according to any one of [1] to [7] contains a compound represented by general formula (L) below.

[Chem. 4]

$$R^{L1}-B^{L1}-L^{L1}-B^{L2}-(L^{L2}-B^{L3})_{OL}-R^{L2} \qquad (L)$$

(In the formula, $R^{L1}$ and $R^{L2}$ each independently represent an alkyl group having 1 to 8 carbon atoms where one —$CH_2$— or two or more non-adjacent —$CH_2$— in the alkyl group may each independently be substituted with —CH=CH—, —C≡C—, —O—, —CO—, —COO—, or —OCO—;

OL represents 0, 1, 2, or 3;

$B^{L1}$, $B^{L2}$, and $B^{L3}$ each independently represent a group selected from the group consisting of:

(a) a 1,4-cyclohexylene group (one —$CH_2$— or two or more non-adjacent —$CH_2$— present in the group may be substituted with —O—) and (b) a 1,4-phenylene group (one —CH= or two or more non-adjacent —CH= present in the group may be substituted with —N=), where one or more hydrogen atoms in the group (a) and the group (b) may each independently be substituted with a cyano group, a fluorine atom, or a chlorine atom;

$L^{L1}$ and $L^{L2}$ each independently represent a single bond, —$CH_2CH_2$—, —$(CH_2)_4$—, —$OCH_2$—, —$CH_2O$—, —COO—, —OCO—, —$OCF_2$—, —$CF_2O$—, —CH=N—, N=CH—, —CH=CH—, —CF=CF—, or —C≡C—; and when OL represents 2 or 3 and thus a plurality of $L^{L2}$ are present, the plurality of $L^{L2}$ may be the same or different and when OL represents 2 or 3 and thus a plurality of $B^{L3}$ are present, the plurality of $B^{L3}$ may be the same or different.)

[9] The liquid crystal composition according to any one of [1] to [8] contains a compound represented by general formula (M) below.

[Chem. 5]

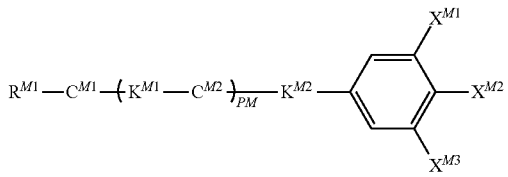

(M)

(In the formula, $R^{M1}$ represents an alkyl group having 1 to 8 carbon atoms where one —$CH_2$— or two or more non-adjacent —$CH_2$— in the alkyl group may each independently be substituted with —CH=CH—, —C≡C—, —O—, —CO—, —COO—, or —OCO—;

PM represents 0, 1, 2, 3, or 4;

$C^{M1}$ and $C^{M2}$ each independently represent a group selected from the group consisting of:

(d) a 1,4-cyclohexylene group (one —$CH_2$— or two or more non-adjacent —$CH_2$— present in the group may be substituted with —O— or —S—) and (e) a 1,4-phenylene group (one —CH= or two or more non-adjacent —CH= present in the group may be substituted with —N=), where one or more hydrogen atoms in the group (d) and the group (e) may each independently be substituted with a cyano group, a fluorine atom, or a chlorine atom;

$K^{M1}$ and $K^{M2}$ each independently represent a single bond, —$CH_2CH_2$—, —$(CH_2)_4$—, —$OCH_2$—, —$CH_2O$—, —$OCF_2$—, —$CF_2O$—, —COO—, —OCO—, or —C≡C—;

when PM represents 2, 3, or 4 and thus a plurality of $K^{M1}$ are present, the plurality of $K^{M1}$ may be the same or different and when PM represents 2, 3, or 4 and thus a plurality of $C^{M2}$ are present, the plurality of $C^{M2}$ may be the same or different;

$X^{M1}$ and $X^{M3}$ each independently represent a hydrogen atom, a chlorine atom, or a fluorine atom; and $X^{M2}$ represents a hydrogen atom, a fluorine atom, a chlorine atom, a cyano group, a trifluoromethyl group, a fluoromethoxy group, a difluoromethoxy group, a trifluoromethoxy group, or a 2,2,2-trifluoroethyl group, the compound represented by the general formula (M) excluding the compounds represented by the general formula (i) and the compounds represented by the general formula (ii).)

[10] A liquid crystal display device uses the liquid crystal composition according to any one of [1] to [9].

[11] A liquid crystal display device for an IPS mode uses the liquid crystal composition according to any one of [1] to [9].

[12] A liquid crystal display device for an FFS mode uses the liquid crystal composition according to any one of [1] to [9].

[13] A liquid crystal display device for an OCB mode uses the liquid crystal composition according to any one of [1] to [9].

[14] A liquid crystal display device for an ECB mode uses the liquid crystal composition according to any one of [1] to [9].

[15] A liquid crystal display device for a VA mode uses the liquid crystal composition according to any one of [1] to [9].

[16] A liquid crystal display device for a VA-IPS mode uses the liquid crystal composition according to any one of [1] to [9].

[17] A liquid crystal display uses the liquid crystal display device according to any one of [10] to [16].

Advantageous Effects of Invention

The liquid crystal composition having a positive dielectric anisotropy according to the present invention has a liquid crystal phase over a wide temperature range, a viscosity much lower than before, and high solubility at low temperature, and the specific resistance and voltage holding ratio of the liquid crystal composition hardly changes through the influence of heat or light. Therefore, the liquid crystal composition of the present invention is highly practical (applicable) for liquid crystal products, and an IPS mode or FFS mode liquid crystal display device using the liquid crystal composition can achieve high-speed response. Furthermore, even after the liquid crystal composition of the present invention undergoes the production process of a liquid crystal display device, the liquid crystal composition stably exhibits its performance. As a result, display defects due to the production process are suppressed and a liquid crystal display device can be produced at a high yield. Therefore, the liquid crystal composition of the present invention is quite useful.

DESCRIPTION OF EMBODIMENTS

Figure 1:
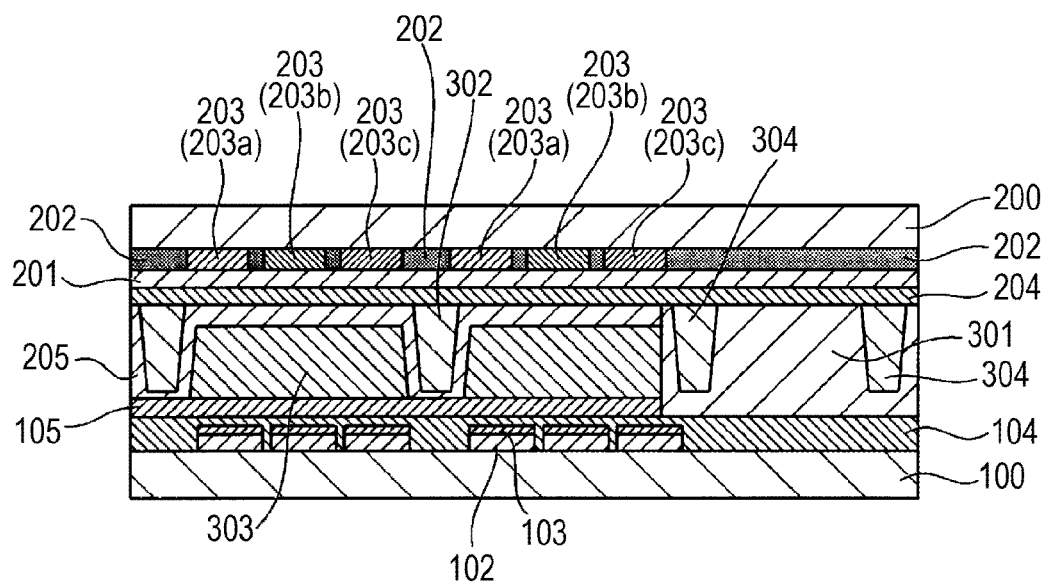
FIG. 1 is a cross-sectional view showing a liquid crystal display device of the present invention. In the drawing, a substrate including elements 100 to 105 is referred to as a "backplane" and a substrate including elements 200 to 205 is referred to as a "frontplane".

A liquid crystal composition having a positive dielectric anisotropy according to a first embodiment of the present invention contains a component (A), which is a dielectrically positive component. The component (A) is constituted by compounds with a dielectric anisotropy of 2 or more.

Note that the dielectric anisotropy of each of the compounds is obtained by extrapolating measured values of the dielectric anisotropy of a composition prepared by adding the compound to a liquid crystal composition whose dielectric anisotropy is about 0 at 25° C.

In the following compositions, "%" means "mass %" unless otherwise specified.

The component (A) contains one or more of compounds represented by general formula (i) below and one or more of compounds represented by general formula (ii) below.

[Chem. 6]

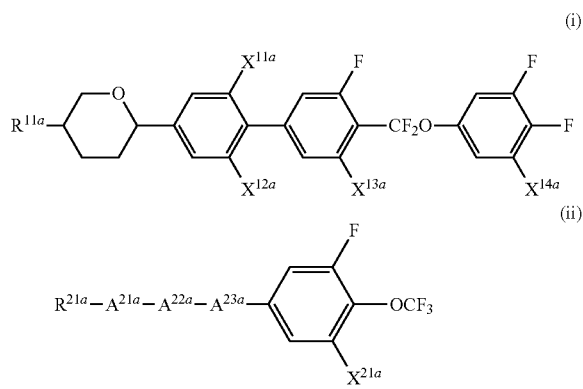

<Compounds Represented by General Formula (i)>

In the general formula (i), $R^{11a}$ represents an alkyl group having 1 to 8 carbon atoms where one —$CH_2$— or two or more non-adjacent —$CH_2$— in the alkyl group may each independently be substituted with —CH=CH—, —C≡C—, —O—, —CO—, —COO—, or —OCO— and hydrogen atoms in the alkyl group may be substituted with fluorine atoms or chlorine atoms.

The number of carbon atoms in the alkyl group is preferably 1 to 6, more preferably 1 to 4, and further preferably 2 or 3.

In the general formula (i), $X^{11a}$, $X^{11a}$, $X^{13a}$, and $X^{14a}$ each independently represent a hydrogen atom or a fluorine atom.

Preferably, at least one of $X^{11a}$ and $X^{12a}$ represents a hydrogen atom. More preferably, both of $X^{11a}$ and $X^{12a}$ represent hydrogen atoms.

$X^{13a}$ preferably represents a fluorine atom and $X^{14a}$ preferably represents a fluorine atom. More preferably, both of $X^{13a}$ and $X^{14a}$ represent fluorine atoms.

The content of the compounds represented by the general formula (i) has its upper limit and lower limit for each embodiment in consideration of characteristics such as solubility at low temperature, transition temperature, electrical reliability, and double refractive index.

The lower limit of the content of the compounds is preferably 1%, more preferably 3%, and more preferably 6% relative to the total mass of the liquid crystal composition of the present invention. The upper limit of the content of the compounds is preferably 30%, more preferably 25%, more preferably 22%, more preferably 20%, and more preferably 18% relative to the total mass.

In the case where only one of the compounds represented by the general formula (i) is used, the lower limit of the content of the compound is preferably 1%, more preferably 2%, and more preferably 3% relative to the total mass. The upper limit of the content of the compound is preferably 20%, more preferably 15%, and more preferably 10% relative to the total mass.

In the case where two of the compounds represented by the general formula (i) are used, the lower limit of the total content of the two compounds is preferably 2%, more preferably 4%, and more preferably 6% relative to the total mass. The upper limit of the total content of the two compounds is preferably 30%, more preferably 25%, more preferably 22%, more preferably 20%, and more preferably 18% relative to the total mass.

In the case where an importance is given to the solubility of the liquid crystal composition, two of the compounds represented by the general formula (i) are preferably used. When the content of the compounds represented by the general formula (i) needs to be increased, the two compounds are preferably used.

For example, the content of the compounds relative to the total mass of the liquid crystal composition of the present invention is 2 to 15 mass % in one embodiment of the present invention, 2 to 12 mass % in another embodiment, 2 to 10 mass % in still another embodiment, 4 to 15 mass % in still yet another embodiment, 4 to 12 mass % in still yet another embodiment, 4 to 10 mass % in still yet another embodiment, 6 to 15 mass % in still yet another embodiment, 6 to 12 mass % in still yet another embodiment, and 6 to 10 mass % in still yet another embodiment.

Furthermore, for example, the content of the compounds relative to the total mass of the liquid crystal composition of the present invention is 8 to 24 mass % in one embodiment of the present invention, 8 to 20 mass % in another embodiment, 8 to 18 mass % in still another embodiment, 10 to 24 mass % in still yet another embodiment, 10 to 20 mass % in still yet another embodiment, 10 to 18 mass % in still yet another embodiment, 12 to 24 mass % in still yet another embodiment, 12 to 20 mass % in still yet another embodiment, and 12 to 18 mass % in still yet another embodiment.

The compounds represented by the general formula (i) are preferably compounds represented by general formula (X-6).

[Chem. 7]

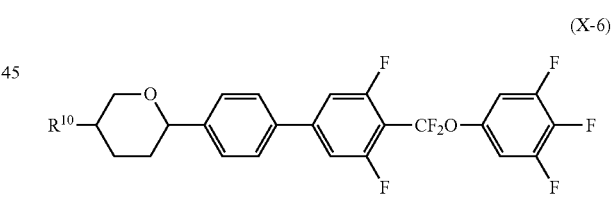

(In the formula, $R^{10}$ represents an alkyl group having 1 to 5 carbon atoms, an alkenyl group having 2 to 5 carbon atoms, or an alkoxy group having 1 to 4 carbon atoms.)

Although the number of compounds that can be combined with each other is not particularly limited, one or more of the compounds represented by the general formula (X-6) are preferably combined with each other in consideration of solubility at low temperature, transition temperature, electrical reliability, double refractive index, and the like.

More specifically, the compounds represented by general formula (X-6) and used for the liquid crystal composition of the present invention are preferably compounds represented by formula (44.1) to formula (44.4). Among the compounds, the compound represented by the formula (44.1) and/or the compound represented by the formula (44.2) are preferably contained in the liquid crystal composition.

[Chem. 8]

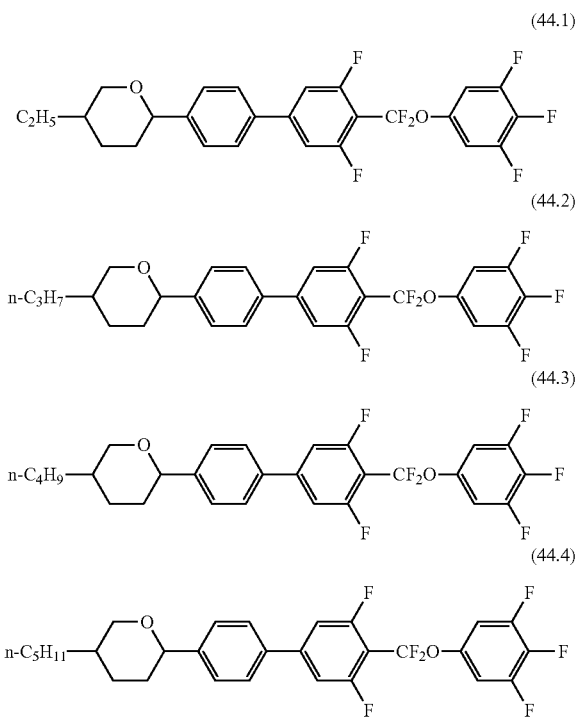

In the liquid crystal composition of the present invention, the lower limit of the content of the compound represented by the formula (44.1) is preferably 1 mass % and more preferably 3 mass % relative to the total mass of the liquid crystal composition of the present invention and the upper limit of the content is preferably 25 mass %, more preferably 20 mass %, more preferably 15 mass %, and more preferably 11 mass % relative to the total mass in consideration of solubility at low temperature, transition temperature, electrical reliability, and the like.

For example, the content of the compound represented by the formula (44.1) relative to the total mass of the liquid crystal composition of the present invention is 2 to 10 mass % in one embodiment of the present invention, 2 to 7 mass % in another embodiment, 2 to 5 mass % in still another embodiment, 3 to 10 mass % in still yet another embodiment, 3 to 7 mass % in still yet another embodiment, and 3 to 5 mass % in still yet another embodiment.

Furthermore, for example, the content of the compound represented by the formula (44.1) relative to the total mass of the liquid crystal composition of the present invention is 3 to 15 mass % in one embodiment of the present invention, 3 to 12 mass % in another embodiment, 3 to 9 mass % in still another embodiment, 5 to 15 mass % in still yet another embodiment, 5 to 12 mass % in still yet another embodiment, and 5 to 9 mass % in still yet another embodiment.

In the liquid crystal composition of the present invention, the lower limit of the content of the compound represented by the formula (44.2) is preferably 1 mass % and more preferably 3 mass % relative to the total mass of the liquid crystal composition of the present invention and the upper limit of the content is preferably 15 mass % and more preferably 11 mass % relative to the total mass in consideration of solubility at low temperature, transition temperature, electrical reliability, and the like.

For example, the content of the compound represented by the formula (44.2) relative to the total mass of the liquid crystal composition of the present invention is 2 to 10 mass % in one embodiment of the present invention, 2 to 7 mass % in another embodiment, 2 to 5 mass % in still another embodiment, 3 to 10 mass % in still yet another embodiment, 3 to 7 mass % in still yet another embodiment, and 3 to 5 mass % in still yet another embodiment.

Furthermore, for example, the content of the compound represented by the formula (44.2) relative to the total mass of the liquid crystal composition of the present invention is 2 to 16 mass % in one embodiment of the present invention, 2 to 14 mass % in another embodiment, 2 to 12 mass % in still another embodiment, 2 to 10 mass % in still yet another embodiment, 4 to 16 mass % in still yet another embodiment, 4 to 14 mass % in still yet another embodiment, and 4 to 12 mass % in still yet another embodiment, 4 to 10 mass % in still yet another embodiment, 6 to 16 mass % in still yet another embodiment, 6 to 14 mass % in still yet another embodiment, 6 to 12 mass % in still yet another embodiment and 6 to 10 mass % in still yet another embodiment.

In the liquid crystal composition of the present invention, the lower limit of the total content of the compound represented by the formula (44.1) and the compound represented by the formula (44.2) is preferably 2%, more preferably 4%, and more preferably 6% and the upper limit of the total content is preferably 30%, more preferably 25%, more preferably 22%, more preferably 20%, and more preferably 18% in consideration of solubility at low temperature, transition temperature, electrical reliability, and the like.

For example, the total content of the compound represented by the formula (44.1) and the compound represented by the formula (44.2) relative to the total mass of the liquid crystal composition of the present invention is 2 to 15 mass % in one embodiment of the present invention, 2 to 12 mass % in another embodiment, 2 to 10 mass % in still another embodiment, 4 to 15 mass % in still yet another embodiment, 4 to 12 mass % in still yet another embodiment, 4 to 10 mass % in still yet another embodiment, 6 to 15 mass % in still yet another embodiment, 6 to 12 mass % in still yet another embodiment, and 6 to 10 mass % in still yet another embodiment.

Furthermore, for example, the total content of the compound represented by the formula (44.1) and the compound represented by the formula (44.2) relative to the total mass of the liquid crystal composition of the present invention is 8 to 24 mass % in one embodiment of the present invention, 8 to 20 mass % in another embodiment, 8 to 18 mass % in still another embodiment, 10 to 24 mass % in still yet another embodiment, 10 to 20 mass % in still yet another embodiment, 10 to 18 mass % in still yet another embodiment, 12 to 24 mass % in still yet another embodiment, 12 to 20 mass % in still yet another embodiment, and 12 to 18 mass % in still yet another embodiment.

<Compound Represented by General Formula (ii)>

In the general formula (ii), $R^{21a}$ represents an alkyl group having 1 to 8 carbon atoms where one —$CH_2$— or two or more non-adjacent —$CH_2$— in the alkyl group may each independently be substituted with —CH=CH—, —C≡C—, —O—, —CO—, —COO—, or —OCO— and one or more hydrogen atoms in the alkyl group may be substituted with fluorine atoms or chlorine atoms.

The number of carbon atoms in the alkyl group is preferably 1 to 6, more preferably 2 to 5, more preferably 2 or 3, and more preferably 3. The alkyl group preferably has a straight chain.

In the general formula (ii), $X^{21a}$ preferably represents a hydrogen atom.

In the general formula (ii), $A^{21a}$ preferably represents a trans-1,4-cyclohexylene group.

In the general formula (ii), $A^{22a}$ preferably represents a 1,4-phenylene group. Four hydrogen atoms are more preferably bonded to the phenylene group (hydrogen atoms in the phenylene group are not substituted).

In the general formula (ii), $A^{23a}$ preferably represents a 1,4-phenylene group. One or two hydrogen atoms bonded to the phenylene group are preferably substituted with fluorine atoms, and two hydrogen atoms bonded to the phenylene group are more preferably substituted with fluorine atoms.

In the general formula (ii), preferably, $A^{21a}$ represents a trans-1,4-cyclohexylene group, $A^{22a}$ represents a (non-substituted) 1,4-phenylene group to which four hydrogen atoms are bonded, and $A^{23a}$ represents a 1,4-phenylene group in which one or two hydrogen atoms are substituted with fluorine atoms.

Although the number of compounds that can be combined with each other is not particularly limited, a plurality of the compounds represented by the general formula (ii) can be used in combination in accordance with desired characteristics such as solubility at low temperature, transition temperature, electrical reliability, and double refractive index. For example, the number of the compounds represented by the general formula (ii) is one in one embodiment of the present invention and two in another embodiment of the present invention.

The content of the compounds represented by the general formula (ii) has a preferred upper limit and a preferred lower limit for each embodiment in consideration of solubility at low temperature, transition temperature, electrical reliability, double refractive index, and the like.

The lower limit of the content of the compounds is preferably 1%, more preferably 2%, and more preferably 4% relative to the total mass of the liquid crystal composition of the present invention. The upper limit of the content of the compounds is preferably 25%, more preferably 20%, more preferably 15%, more preferably 12%, more preferably 10%, and more preferably 8% relative to the total mass.

In the case where only one of the compounds represented by the general formula (ii) is used, the lower limit of the content of the compound is preferably 1%, more preferably 2%, more preferably 3%, and more preferably 4% relative to the total mass. The upper limit of the content of the compound is preferably 25%, more preferably 20%, more preferably 15%, more preferably 12%, more preferably 10%, and more preferably 8% relative to the total mass.

In the case where two of the compounds represented by the general formula (ii) are used, the lower limit of the total content of the two compounds is preferably 2%, more preferably 4%, and more preferably 6% relative to the total mass. The upper limit of the total content of the two compounds is preferably 25%, more preferably 20%, more preferably 17%, and more preferably 15% relative to the total mass.

One or more of the compounds represented by the general formula (ii) can be used, but one compound is preferably used.

The content of the compounds represented by the general formula (ii) relative to the total mass is 2 to 15 mass % in one embodiment, 2 to 12 mass % in another embodiment, 2 to 10 mass % in still another embodiment, 2 to 8 mass % in still yet another embodiment, 4 to 15 mass % in still yet another embodiment, 4 to 12 mass % in still yet another embodiment, 4 to 10 mass % in still yet another embodiment, and 4 to 8 mass % in still yet another embodiment.

The compounds represented by the general formula (ii) are preferably compounds represented by general formula (X-2-1) below.

[Chem. 9]

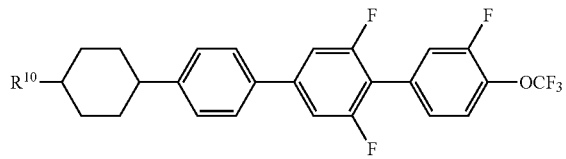

(X-2-1)

(In the formula, $R^{10}$ represents an alkyl group having 1 to 5 carbon atoms, an alkenyl group having 2 to 5 carbon atoms, or an alkoxy group having 1 to 4 carbon atoms.)

Compounds that can be combined with each other are not particularly limited. One or more of the compounds can be combined with each other in consideration of solubility at low temperature, transition temperature, electrical reliability, double refractive index, and the like, but one of the compounds represented by the general formula (X-2-1) is preferably used.

In consideration of solubility at low temperature, transition temperature, electrical reliability, and the like, the lower limit of the total content of the compounds represented by the general formula (X-2-1) is preferably 1%, more preferably 2%, more preferably 3%, and more preferably 4% relative to the total mass of the liquid crystal composition of the present invention. The upper limit of the total content of the compounds is preferably 25%, more preferably 20%, more preferably 15%, more preferably 12%, more preferably 10%, and more preferably 8% relative to the total mass.

The content of the compounds represented by the general formula (X-2-1) relative to the total mass is 2 to 15 mass % in one embodiment, 2 to 12 mass % in another embodiment, 2 to 10 mass % in still another embodiment, 2 to 8 mass % in still yet another embodiment, 4 to 15 mass % in still yet another embodiment, 4 to 12 mass % in still yet another embodiment, 4 to 10 mass % in still yet another embodiment, and 4 to 8 mass % in still yet another embodiment.

More specifically, the compounds represented by the general formula (X-2-1) and used for the liquid crystal composition of the present invention are preferably compounds represented by formula (39.1) to formula (39.4). Among the compounds, the liquid crystal composition preferably contains the compound represented by the formula (39.1) and/or the compound represented by the formula (39.2).

[Chem. 10]

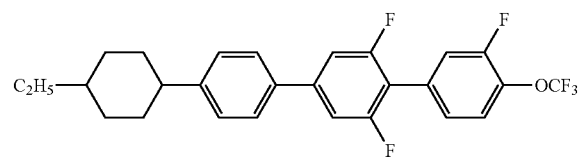

(39.1)

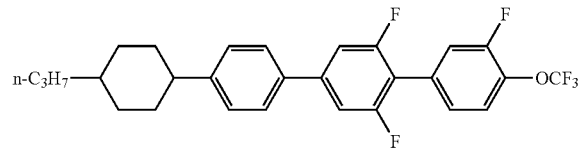

(39.2)

-continued

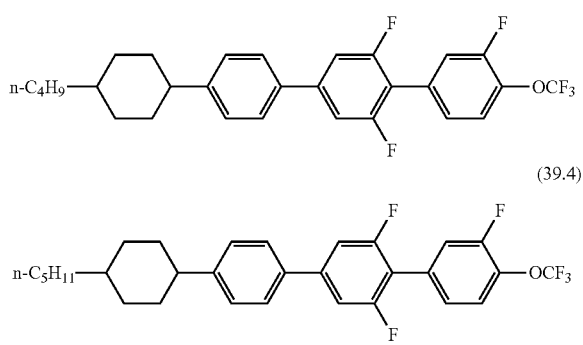

In the liquid crystal composition of the present invention, the lower limit of the content of the compound represented by the formula (39.1) is preferably 1%, more preferably 2%, more preferably 3%, and more preferably 4% relative to the total mass of the liquid crystal composition of the present invention and the upper limit of the content is preferably 25%, more preferably 20%, more preferably 15%, more preferably 12%, and more preferably 10% relative to the total mass.

The content of the compound represented by the formula (39.1) relative to the total mass is 2 to 15 mass % in one embodiment, 2 to 12 mass % in another embodiment, 2 to 10 mass % in still another embodiment, 2 to 8 mass % in still yet another embodiment, 4 to 15 mass % in still yet another embodiment, 4 to 12 mass % in still yet another embodiment, 4 to 10 mass % in still yet another embodiment, and 4 to 8 mass % in still yet another embodiment.

In the liquid crystal composition of the present invention, the lower limit of the content of the compound represented by the formula (39.2) is preferably 1%, more preferably 2%, more preferably 3%, and more preferably 4% relative to the total mass of the liquid crystal composition of the present invention and the upper limit of the content is preferably 25%, more preferably 20%, more preferably 15%, more preferably 12%, more preferably 10%, and more preferably 8% relative to the total mass.

The content of the compound represented by the formula (39.2) relative to the total mass is 2 to 15 mass % in one embodiment, 2 to 12 mass % in another embodiment, 2 to 10 mass % in still another embodiment, 2 to 8 mass % in still yet another embodiment, 4 to 15 mass % in still yet another embodiment, 4 to 12 mass % in still yet another embodiment, 4 to 10 mass % in still yet another embodiment, and 4 to 8 mass % in still yet another embodiment.

The compounds represented by the general formula (ii) are preferably compounds represented by general formula (X-2-2) below.

[Chem. 11]

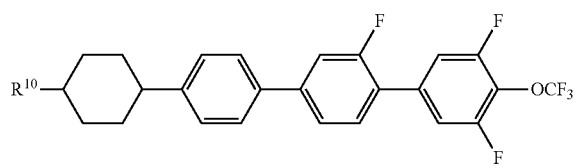

(In the formula, $R^{10}$ represents an alkyl group having 1 to 5 carbon atoms, an alkenyl group having 2 to 5 carbon atoms, or an alkoxy group having 1 to 4 carbon atoms.)

Compounds that can be combined with each other are not particularly limited. One or more of the plurality of compounds represented by the general formula (X-2-2) are preferably combined with each other in consideration of solubility at low temperature, transition temperature, electrical reliability, double refractive index, and the like.

The content of the compounds represented by the general formula (X-2-2) is preferably 1 mass % or more and 20 mass % or less, more preferably 2 mass % or more and 10 mass % or less, and more preferably 3 mass % or more and 6 mass % or less relative to the total mass of the liquid crystal composition of the present invention in consideration of solubility at low temperature, transition temperature, electrical reliability, and the like.

More specifically, the compounds represented by the general formula (X-2-2) and used for the liquid crystal composition of the present invention are preferably compounds represented by formula (40.1) to formula (40.4). Among the compounds, the liquid crystal composition preferably contains a compound represented by formula (40.2).

[Chem. 12]

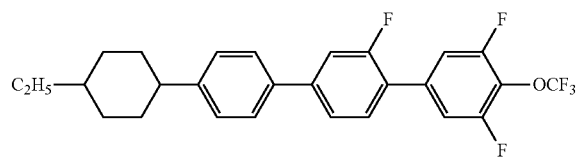

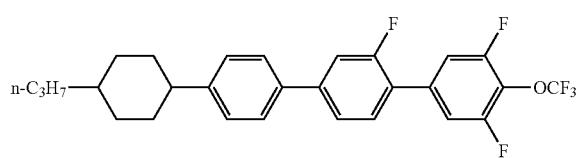

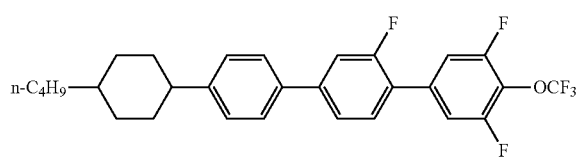

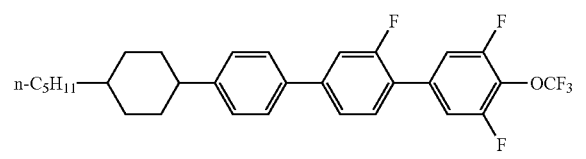

In the liquid crystal composition of the present invention, the content of the compound represented by the formula (40.2) is preferably 1 mass % or more and 20 mass % or less, more preferably 2 mass % and 15 mass % or less, 3 mass % or more and 10 mass % or less, and 3 mass % or more and 6 mass % or less relative to the total mass of the liquid crystal composition of the present invention.

In the preferred range, the content may be 3 to 5 mass %, 3 to 4 mass %, 4 to 6 mass %, or 5 to 6 mass %.

Among the compounds represented by the general formula (i) and the compounds represented by the general formula (ii), two to four compounds in total are preferably used, three or four compounds in total are more preferably used, and three compounds in total are particularly preferably used. In this case, particularly preferably, the compounds represented by the formula (44.1) and the formula (44.2) are used as the compounds represented by the general formula (i) and the compound represented by the formula (39.2) is used as the compounds represented by the general formula (ii).

The lower limit of the total content of the compounds represented by the general formula (i) and the compounds represented by the general formula (ii) is preferably 8 mass %, more preferably 10 mass %, and more preferably 12 mass % relative to the total mass of the liquid crystal composition of the present invention. The upper limit of the total content is preferably 50 mass %, more preferably 40 mass %, more preferably 35 mass %, more preferably 30 mass %, and more preferably 25 mass % relative to the total mass.

The combination of the lower limit and the upper limit is preferably in the range of 8 to 50 mass %. In this preferred range, examples of the content according to one embodiment include 8 to 20 mass %, 8 to 18 mass %, 8 to 16 mass %, 10 to 20 mass %, 10 to 18 mass %, 10 to 16 mass %, 12 to 20 mass %, 12 to 18 mass %, and 12 to 16 mass %.

Examples of the content according to another embodiment include 12 to 30 mass %, 12 to 27 mass %, 12 to 25 mass %, 12 to 23 mass %, 16 to 30 mass %, 16 to 27 mass %, 16 to 25 mass %, and 16 to 23 mass %.

Three compounds in total, that is, two of the compounds represented by the general formula (i) and one of the compounds represented by the general formula (ii) are preferably used. The lower limit of the total content of the three compounds is preferably 8 mass %, more preferably 10 mass %, and more preferably 12 mass % relative to the total mass. The upper limit of the total content is preferably 50 mass %, more preferably 40 mass %, more preferably 35 mass %, more preferably 30 mass %, and more preferably 25 mass % relative to the total mass.

The combination of the lower limit and the upper limit is preferably in the range of 8 to 50 mass %. In this preferred range, examples of the content according to one embodiment include 8 to 20 mass %, 8 to 18 mass %, 8 to 16 mass %, 10 to 20 mass %, 10 to 18 mass %, 10 to 16 mass %, 12 to 20 mass %, 12 to 18 mass %, and 12 to 16 mass %.

Examples of the content according to another embodiment include 12 to 30 mass %, 12 to 27 mass %, 12 to 25 mass %, 12 to 23 mass %, 16 to 30 mass %, 16 to 27 mass %, 16 to 25 mass %, and 16 to 23 mass %.

In the case where an importance is given to the solubility of the liquid crystal composition, three of the compounds in total or four of the compounds in total are preferably used. When the total content of the compounds represented by the general formula (i) and the compounds represented by the general formula (ii) needs to be increased, three of the compounds in total or four of the compounds in total are preferably used.

The liquid crystal composition according to the first embodiment of the present invention may also contain one or more of compounds represented by general formula (L) below.

[Chem. 13]

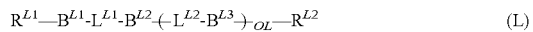
(L)

(In the formula, $R^{L1}$ and $R^{L2}$ each independently represent an alkyl group having 1 to 8 carbon atoms where one —$CH_2$— or two or more non-adjacent —$CH_2$— in the alkyl group may each independently be substituted with —CH=CH—, —C≡C—, —O—, —CO—, —COO—, or —OCO—;

OL represents 0, 1, 2, or 3;

$B^{L1}$, $B^{L2}$, and $B^{L3}$ each independently represent a group selected from the group consisting of:

(a) a 1,4-cyclohexylene group (one —$CH_2$— or two or more non-adjacent —$CH_2$— present in the group may be substituted with —O—) and (b) a 1,4-phenylene group (one —CH= or two or more non-adjacent —CH= present in the group may be substituted with —N=), where one or more hydrogen atoms in the group (a) and the group (b) may each independently be substituted with a cyano group, a fluorine atom, or a chlorine atom;

$L^{L1}$ and $L^{L2}$ each independently represent a single bond, —$CH_2CH_2$—, —$(CH_2)_4$—, —$OCH_2$—, —$CH_2O$—, —COO—, —OCO—, —$OCF_2$—, —$CF_2O$—, —CH=N—N=CH—, —CH=CH—, —CF=CF—, or —C≡C—; and when OL represents 2 or 3 and thus a plurality of $L^{L2}$ are present, the plurality of $L^{L2}$ may be the same or different and when OL represents 2 or 3 and thus a plurality of $B^{L3}$ are present, the plurality of $B^{L3}$ may be the same or different.)

Although the number of compounds that can be combined with each other is not particularly limited, a plurality of the compounds represented by the general formula (L) can be suitably used in combination in accordance with desired characteristics such as solubility at low temperature, transition temperature, electrical reliability, and double refractive index. For example, the number of the compounds used is one in one embodiment of the present invention. The number of the compounds is two in another embodiment of the present invention. The number of the compounds is three in still another embodiment of the present invention. The number of the compounds is four in still yet another embodiment of the present invention. The number of the compounds is five in still yet another embodiment of the present invention. The number of the compounds is six in still yet another embodiment of the present invention. The number of the compounds is seven in still yet another embodiment of the present invention. The number of the compounds is eight in still yet another embodiment of the present invention. The number of the compounds is nine in still yet another embodiment of the present invention. The number of the compounds is ten or more in still yet another embodiment of the present invention.

In the liquid crystal composition of the present invention, the content of the compounds represented by the general formula (L) needs to be appropriately adjusted in accordance with the required characteristics such as solubility at low temperature, transition temperature, electrical reliability, double refractive index, process compatibility, drop marks, image sticking, and dielectric anisotropy.

For example, the content of the compounds is 1 to 95 mass % relative to the total mass of the liquid crystal composition of the present invention in one embodiment of the present invention. The content is 10 to 95 mass % in another embodiment of the present invention. The content is 20 to 95 mass % in still another embodiment of the present invention. The content is 30 to 95 mass % in still yet another embodiment of the present invention. The content is 40 to 95 mass % in still yet another embodiment of the present invention. The content is 50 to 95 mass % in still yet another embodiment of the present invention. The content is 55 to 95 mass % in still yet another embodiment of the present invention. The content is 60 to 95 mass % in still yet another embodiment of the present invention. The content is 65 to 95 mass % in still yet another embodiment of the present invention. The content is 70 to 95 mass % in still yet another embodiment of the present invention. The content is 75 to 95 mass % in still yet another embodiment of the present invention. The content is 80 to 95 mass % in still yet another embodiment of the present invention.

Furthermore, the content of the compounds is 1 to 95% relative to the total mass of the liquid crystal composition of the present invention in one embodiment of the present invention. The content is 1 to 85% in another embodiment of the present invention. The content is 1 to 75% in still another embodiment of the present invention. The content is 1 to 65% in still yet another embodiment of the present invention. The content is 1 to 55% in still yet another embodiment of the present invention. The content is 1 to 45% in still yet another embodiment of the present invention. The content is 1 to 35% in still yet another embodiment of the present invention. The content is 1 to 25% in still yet another embodiment of the present invention.

When the liquid crystal composition of the present invention needs to have low viscosity to achieve high response speed, the lower limit and the upper limit are preferably set to be high. When the liquid crystal composition of the present invention needs to have high Tni to achieve good temperature stability, the lower limit and the upper limit are preferably set to be high. When the dielectric anisotropy is increased to maintain low drive voltage, the lower limit and the upper limit are preferably set to be low.

In the case where a ring structure to which $R^{L1}$ and $R^{L2}$ are bonded is a phenyl group (aromatic group), $R^{L1}$ and $R^{L2}$ preferably each represent a linear alkyl group having 1 to 5 carbon atoms, a linear alkoxy group having 1 to 4 (or more) carbon atoms, or an alkenyl group having 4 or 5 carbon atoms. In the case where a ring structure to which $R^{L1}$ and $R^{L2}$ are bonded is a saturated ring structure such as cyclohexane, pyran, or dioxane, $R^{L1}$ and $R^{L2}$ preferably each represent a linear alkyl group having 1 to 5 carbon atoms, a linear alkoxy group having 1 to 4 (or more) carbon atoms, or a linear alkenyl group having 2 to 5 carbon atoms.

In the case where the chemical stability of the liquid crystal composition is required, the compounds represented by the general formula (L) preferably do not include chlorine atoms in their molecules.

The compounds represented by the general formula (L) are preferably, for example, compounds selected from the group of compounds represented by general formula (I)

[Chem. 14]

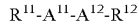
(I)

(In the formula, $R^{11}$ and $R^{12}$ each independently represent an alkyl group having 1 to 5 carbon atoms, an alkoxy group having 1 to 5 carbon atoms, or an alkenyl group having 2 to 5 carbon atoms; and $A^{11}$ and $A^{12}$ each independently represent a 1,4-cyclohexylene group, a 1,4-phenylene group, a 2-fluoro-1,4-phenylene group, or a 3-fluoro-1,4-phenylene group.)

Although the number of compounds that can be combined with each other is not particularly limited, a plurality of the compounds represented by the general formula (I) can be suitably used in combination in accordance with the required characteristics such as solubility at low temperature, transition temperature, electrical reliability, and double refractive index. For example, the number of the compounds used is one in one embodiment of the present invention. The number of the compounds is two in another embodiment of the present invention. The number of the compounds is three in still another embodiment of the present invention. The number of the compounds is four in still yet another embodiment of the present invention. The number of the compounds is five in still yet another embodiment of the present invention. The number of the compounds is six or more in still yet another embodiment of the present invention.

In the liquid crystal composition of the present invention, the content of the compounds represented by the general formula (I) needs to be appropriately adjusted in accordance with the required characteristics such as solubility at low temperature, transition temperature, electrical reliability, double refractive index, process compatibility, drop marks, image sticking, and dielectric anisotropy.

For example, the content of the compounds is 3 to 75 mass % relative to the total mass of the liquid crystal composition of the present invention in one embodiment of the present invention. The content is 15 to 75 mass % in another embodiment of the present invention. The content is 18 to 75 mass % in still another embodiment of the present invention. The content is 20 to 75 mass % in still yet another embodiment of the present invention. The content is 29 to 75 mass % in still yet another embodiment of the present invention. The content is 35 to 75 mass % in still yet another embodiment of the present invention. The content is 42 to 75 mass % in still yet another embodiment of the present invention. The content is 47 to 75 mass % in still yet another embodiment of the present invention. The content is 53 to 75 mass % in still yet another embodiment of the present invention. The content is 56 to 75 mass % in still yet another embodiment of the present invention. The content is 60 to 75 mass % in still yet another embodiment of the present invention. The content is 65 to 75 mass % in still yet another embodiment of the present invention.

Furthermore, for example, the content of the compounds is 3 to 75 mass % relative to the total mass of the liquid crystal composition of the present invention in one embodiment of the present invention. The content is 3 to 65 mass % in another embodiment of the present invention. The content is 3 to 55 mass % in still another embodiment of the present invention. The content is 3 to 50 mass % in still yet another embodiment of the present invention. The content is 3 to 45 mass % in still yet another embodiment of the present invention. The content is 3 to 40 mass % in still yet another embodiment of the present invention. The content is 3 to 35 mass % in still yet another embodiment of the present invention. The content is 3 to 30 mass % in still yet another embodiment of the present invention.

When the liquid crystal composition of the present invention needs to have low viscosity to achieve high response speed, the lower limit and the upper limit are preferably set to be high. When the liquid crystal composition of the present invention needs to have high Tni to achieve good temperature stability, the lower limit and the upper limit are preferably set to be middle. When the dielectric anisotropy is increased to maintain low drive voltage, the lower limit and the upper limit are preferably set to be low.

In the case where a ring structure to which $R^{M1}$ is bonded is a phenyl group (aromatic group), $R^{M1}$ preferably represents a linear alkyl group having 1 to 5 carbon atoms, a linear alkoxy group having 1 to 4 carbon atoms, or an alkenyl group having 4 or 5 carbon atoms. In the case where a ring structure to which $R^{M1}$ is bonded is a saturated ring structure such as cyclohexane, pyran, or dioxane, $R^{M1}$ preferably represents a linear alkyl group having 1 to 5 carbon atoms, a linear alkoxy group having 1 to 4 carbon atoms, or a linear alkenyl group having 2 to 5 carbon atoms.

Furthermore, the compounds represented by the general formula (I) are preferably compounds selected from the group of compounds represented by general formula (I-1).

[Chem. 15]

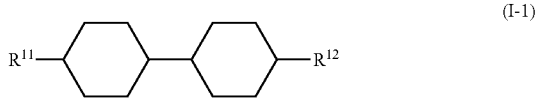
(I-1)

(In the formula, $R^{11}$ and $R^{12}$ each independently represent an alkyl group having 1 to 5 carbon atoms, an alkoxy group having 1 to 5 carbon atoms, or an alkenyl group having 2 to 5 carbon atoms.)

Although the number of compounds that can be combined with each other is not particularly limited, a plurality of the compounds represented by the general formula (I-1) can be suitably used in combination in accordance with the required characteristics such as solubility at low temperature, transition temperature, electrical reliability, and double refractive index. For example, the number of the compounds used is one in one embodiment of the present invention. The number of the compounds is two in another embodiment of the present invention. The number of the compounds is three in still another embodiment of the present invention. The number of the compounds is four in still yet another embodiment of the present invention. The number of the compounds is five or more in still yet another embodiment of the present invention.

In the liquid crystal composition of the present invention, the content of the compounds represented by the general formula (I-1) needs to be appropriately adjusted in accordance with the required characteristics such as solubility at low temperature, transition temperature, electrical reliability, double refractive index, process compatibility, drop marks, image sticking, and dielectric anisotropy.

For example, the content of the compounds is 3 to 70 mass % relative to the total mass of the liquid crystal composition of the present invention in one embodiment of the present invention. The content is 15 to 70 mass % in another embodiment of the present invention. The content is 18 to 70 mass % in still another embodiment of the present invention. The content is 25 to 70 mass % in still yet another embodiment of the present invention. The content is 29 to 70 mass % in still yet another embodiment of the present invention. The content is 31 to 70 mass % in still yet another embodiment of the present invention. The content is 35 to 70 mass % in still yet another embodiment of the present invention. The content is 43 to 70 mass % in still yet another embodiment of the present invention. The content is 47 to 70 mass % in still yet another embodiment of the present invention. The content is 50 to 70 mass % in still yet another embodiment of the present invention. The content is 53 to 70 mass % in still yet another embodiment of the present invention. The content is 56 to 70 mass % in still yet another embodiment of the present invention.

For example, the content of the compounds is 3 to 70 mass % relative to the total mass of the liquid crystal composition of the present invention in one embodiment of the present invention. The content is 3 to 60 mass % in another embodiment of the present invention. The content is 3 to 50 mass % in still another embodiment of the present invention. The content is 3 to 45 mass % in still yet another embodiment of the present invention. The content is 3 to 40 mass % in still yet another embodiment of the present invention. The content is 3 to 35 mass % in still yet another embodiment of the present invention. The content is 3 to 30 mass % in still yet another embodiment of the present invention. The content is 3 to 26 mass % in still yet another embodiment of the present invention.

When the liquid crystal composition of the present invention needs to have low viscosity to achieve high response speed, the lower limit and the upper limit are preferably set to be high. When the liquid crystal composition of the present invention needs to have high Tni to achieve good temperature stability, the lower limit and the upper limit are preferably set to be middle. When the dielectric anisotropy is increased to maintain low drive voltage, the lower limit and the upper limit are preferably set to be low.

Furthermore, the compounds represented by the general formula (I-1) are preferably compounds selected from the group of compounds represented by general formula (I-1-1).

[Chem. 16]

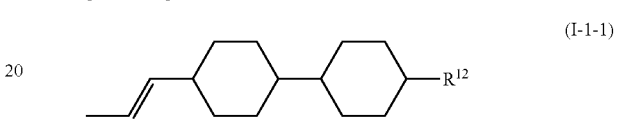
(I-1-1)

(In the formula, $R^{12}$ represents an alkyl group having 1 to 5 carbon atoms, an alkenyl group having 2 to 5 carbon atoms, or an alkoxy group having 1 to 5 carbon atoms.)

In the liquid crystal composition of the present invention, the content of the compounds represented by the general formula (I-1-1) needs to be appropriately adjusted in accordance with the required characteristics such as solubility at low temperature, transition temperature, electrical reliability, double refractive index, process compatibility, drop marks, image sticking, and dielectric anisotropy.

For example, the content of the compounds is 2 to 60 mass % relative to the total mass of the liquid crystal composition of the present invention in one embodiment of the present invention. The content is 4 to 60 mass % in another embodiment of the present invention. The content is 7 to 60 mass % in still another embodiment of the present invention. The content is 11 to 60 mass % in still yet another embodiment of the present invention. The content is 13 to 60 mass % in still yet another embodiment of the present invention. The content is 15 to 60 mass % in still yet another embodiment of the present invention. The content is 17 to 60 mass % in still yet another embodiment of the present invention. The content is 20 to 60 mass % in still yet another embodiment of the present invention. The content is 25 to 60 mass % in still yet another embodiment of the present invention. The content is 30 to 60 mass % in still yet another embodiment of the present invention. The content is 32 to 60 mass % in still yet another embodiment of the present invention. The content is 35 to 60 mass % in still yet another embodiment of the present invention.

For example, the content of the compounds is 2 to 60 mass % relative to the total mass of the liquid crystal composition of the present invention in one embodiment of the present invention. The content is 2 to 50 mass % in another embodiment of the present invention. The content is 2 to 40 mass % in still another embodiment of the present invention. The content is 2 to 35 mass % in still yet another embodiment of the present invention. The content is 2 to 30 mass % in still yet another embodiment of the present invention. The content is 2 to 25 mass % in still yet another embodiment of the present invention. The content is 2 to 20 mass % in still yet another embodiment of the present invention. The content is 2 to 15 mass % in still yet another embodiment of the present invention.

Furthermore, the compounds represented by the general formula (I-1-1) are preferably compounds selected from the group of compounds represented by formula (1.1) to formula (1.3), more preferably a compound represented by formula (1.2) or a compound represented by formula (1.3), and particularly preferably a compound represented by formula (1.3).

[Chem. 17]

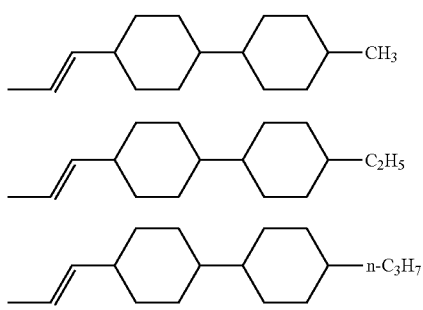

When the compound represented by the formula (1.2) is used alone, the content of the compound represented by the formula (1.2) is preferably high because the response speed is improved. When the compound represented by the formula (1.3) is used alone, the content of the compound represented by the formula (1.3) is preferably in the following range because an electrically and optically reliable liquid crystal composition having high response speed can be provided.

The content of the compound represented by the formula (1.3) is preferably 5 mass % or more and 35 mass % or less, more preferably 5 mass % or more and 30 mass % or less, more preferably 5 mass % or more and 25 mass % or less, particularly preferably 5 mass % or more and 20 mass % or less, and most preferably 10 mass % or more and 17 mass % or less relative to the total mass of the liquid crystal composition of the present invention.

Examples of the content in the most preferable range include 10 mass % or more and 16 mass % or less, 10 mass % or more and 15 mass % or less, 10 mass % or more and 12 mass % or less, 12 mass % or more and 17 mass % or less, 15 mass % or more and 17 mass % or less, and 16 mass % or more and 17 mass % or less.

Furthermore, the compounds represented by the general formula (I-1) are preferably compounds selected from the group of compounds represented by general formula (I-1-2).

[Chem. 18]

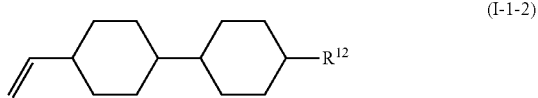

(In the formula, $R^{12}$ represents an alkyl group having 1 to 5 carbon atoms, an alkoxy group having 1 to 5 carbon atoms, or an alkenyl group having 2 to 5 carbon atoms.)

Although the number of compounds that can be combined with each other is not particularly limited, a plurality of the compounds represented by the general formula (I-1-2) can be suitably used in combination in accordance with the required characteristics such as solubility at low temperature, transition temperature, electrical reliability, and double refractive index. For example, the number of the compounds used is one in one embodiment of the present invention. The number of the compounds is two in another embodiment of the present invention. The number of the compounds is three in still another embodiment of the present invention.

In the liquid crystal composition of the present invention, the content of the compounds represented by the general formula (I-1-2) needs to be appropriately adjusted in accordance with the required characteristics such as solubility at low temperature, transition temperature, electrical reliability, double refractive index, process compatibility, drop marks, image sticking, and dielectric anisotropy.

For example, the content of the compounds is 7 to 60 mass % relative to the total mass of the liquid crystal composition of the present invention in one embodiment of the present invention. The content is 15 to 60 mass % in another embodiment of the present invention. The content is 18 to 60 mass % in still another embodiment of the present invention. The content is 21 to 60 mass % in still yet another embodiment of the present invention. The content is 24 to 60 mass % in still yet another embodiment of the present invention. The content is 27 to 60 mass % in still yet another embodiment of the present invention. The content is 30 to 60 mass % in still yet another embodiment of the present invention. The content is 34 to 60 mass % in still yet another embodiment of the present invention. The content is 37 to 60 mass % in still yet another embodiment of the present invention. The content is 41 to 60 mass % in still yet another embodiment of the present invention. The content is 47 to 60 mass % in still yet another embodiment of the present invention. The content is 50 to 60 mass % in still yet another embodiment of the present invention.

Furthermore, for example, the content of the compounds is 7 to 60 mass % relative to the total mass of the liquid crystal composition of the present invention in one embodiment of the present invention. The content is 7 to 55 mass % in another embodiment of the present invention. The content is 7 to 45 mass % in still another embodiment of the present invention. The content is 7 to 40 mass % in still yet another embodiment of the present invention. The content is 7 to 35 mass % in still yet another embodiment of the present invention. The content is 7 to 30 mass % in still yet another embodiment of the present invention. The content is 7 to 25 mass % in still yet another embodiment of the present invention. The content is 7 to 20 mass % in still yet another embodiment of the present invention.

Furthermore, the compounds represented by the general formula (I-1-2) are preferably compounds selected from the group of compounds represented by formula (2.1) to formula (2.4) and more preferably compounds represented by formula (2.2) to formula (2.4). In particular, the compound represented by the formula (2.2) is preferably used because the response speed of the liquid crystal composition of the present invention is considerably improved. When high Tni is required rather than the response speed, the compound represented by the formula (2.3) or the compound represented by the formula (2.4) is preferably used. The content of the compound represented by the formula (2.3) or the compound represented by the formula (2.4) is preferably less than 30% to increase the solubility at low temperature.

[Chem. 19]

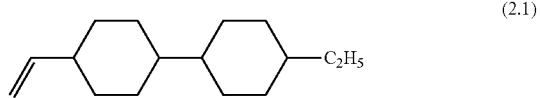

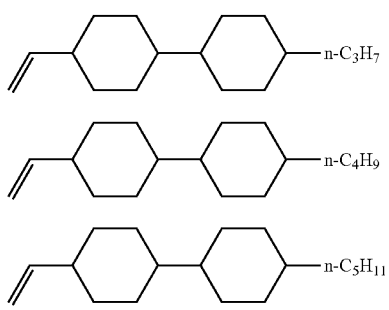

(2.2)

(2.3)

(2.4)

In the liquid crystal composition of the present invention, the content of the compound represented by the formula (2.2) is preferably 5 mass % or more and 55 mass % or less relative to the total mass of the liquid crystal composition of the present invention. Preferred examples of the content include 10 mass % and 50 mass % or less, 20 mass % or more and 50 mass % or less, 30 mass % or more and 50 mass % or less, 35 mass % or more and 50 mass % or less, and 38 mass % or more and 44 mass % or less.

Among the above ranges, 38 mass % or more and 44 mass % or less is particularly preferred. Examples of the content in the particularly preferable range include 38 mass % or more and 42 mass % or less, 38 mass % or more and 40 mass % or less, 38 mass % or more and 39 mass % or less, 39 mass % or more and 44 mass % or less, 40 mass % or more and 44 mass % or less, and 42 mass % or more and 44 mass % or less.

In the liquid crystal composition of the present invention, the content of the compound represented by the formula (2.3) is preferably 5 mass % or more and 55 mass % or less, more preferably 5 mass % and 45 mass % or less, more preferably 5 mass % or more and 35 mass % or less, more preferably 5 mass % or more and 25 mass % or less, more preferably 10 mass % or more and 25 mass % or less, and particularly preferably 15 mass % or more and 25 mass % or less relative to the total mass of the liquid crystal composition of the present invention.

Examples of the content in the particularly preferable range include 15 mass % or more and 22 mass % or less, 15 mass % or more and 20 mass % or less, 15 mass % or more and 17 mass % or less, 17 mass % or more and 25 mass % or less, 20 mass % or more and 25 mass % or less, and 22 mass % or more and 25 mass % or less.

In the liquid crystal composition of the present invention, the content of the compound represented by the formula (2.4) is preferably 1 mass % or more and 55 mass % or less, more preferably 2 mass % and 40 mass % or less, more preferably 3 mass % or more and 25 mass % or less, more preferably 4 mass % or more and 15 mass % or less, particularly preferably 5 mass % or more and 10 mass % or less, and most preferably 5 mass % or more and 7 mass % or less relative to the total mass of the liquid crystal composition of the present invention.

In the most preferable range, the content may be 5 mass % or more and 6 mass % or less or may be 6 mass % or more and 7 mass % or less.

The liquid crystal composition of the present invention may further contain a compound represented by formula (2.5), the compound having a structure similar to the structure of the compounds represented by the general formula (I-1-2).

[Chem. 20]

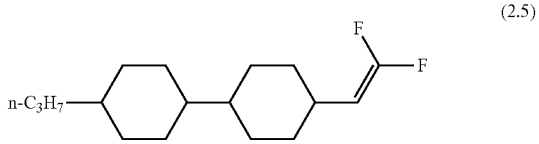

(2.5)

The content of the compound represented by the formula (2.5) is preferably adjusted in accordance with the required characteristics such as solubility at low temperature, transition temperature, electrical reliability, and double refractive index. The content of the compound is preferably 11 mass % or more, more preferably 15 mass % or more, more preferably 23 mass % or more, more preferably 26 mass % or more, and particularly preferably 28 mass % or more relative to the total mass of the liquid crystal composition of the present invention.

Furthermore, the compounds represented by the general formula (I) are preferably compounds selected from the group of compounds represented by general formula (I-2).

[Chem. 21]

$$R^{13}\!-\!\!\bigcirc\!\!-\!\!\bigcirc\!\!-\!R^{14}$$

(I-2)

(In the formula, $R^{13}$ and $R^{14}$ each independently represent an alkyl group having 1 to 5 carbon atoms.)

Although the number of compounds that can be combined with each other is not particularly limited, a plurality of the compounds represented by the general formula (I-2) can be used in combination in accordance with the required characteristics such as solubility at low temperature, transition temperature, electrical reliability, and double refractive index. For example, the number of the compounds used is one in one embodiment of the present invention. The number of the compounds is two in another embodiment of the present invention. The number of the compounds is three in still another embodiment of the present invention.

In the liquid crystal composition of the present invention, the content of the compounds represented by the general formula (I-2) needs to be appropriately adjusted in accordance with the required characteristics such as solubility at low temperature, transition temperature, electrical reliability, double refractive index, process compatibility, drop marks, image sticking, and dielectric anisotropy.

For example, the content of the compounds is 3 to 60 mass % relative to the total mass of the liquid crystal composition of the present invention in one embodiment of the present invention. The content is 4 to 60 mass % in another embodiment of the present invention. The content is 15 to 60 mass % in still another embodiment of the present invention. The content is 25 to 60 mass % in still yet another embodiment of the present invention. The content is 30 to 60 mass % in still yet another embodiment of the present invention. The content is 35 to 60 mass % in still yet another embodiment of the present invention. The content is 38 to 60 mass % in still yet another embodiment of the present invention. The content is 40 to 60 mass % in still yet another embodiment of the present invention. The content is 42 to 60 mass % in still yet another embodiment of the present invention.

The content is 45 to 60 mass % in still yet another embodiment of the present invention. The content is 47 to 60 mass % in still yet another embodiment of the present invention. The content is 50 to 60 mass % in still yet another embodiment of the present invention.

Furthermore, for example, the content of the compounds is 3 to 60 mass % relative to the total mass of the liquid crystal composition of the present invention in one embodiment of the present invention. The content is 3 to 55 mass % in another embodiment of the present invention. The content is 3 to 45 mass % in still another embodiment of the present invention. The content is 3 to 40 mass % in still yet another embodiment of the present invention. The content is 3 to 30 mass % in still yet another embodiment of the present invention. The content is 3 to 20 mass % in still yet another embodiment of the present invention. The content is 3 to 15 mass % in still yet another embodiment of the present invention. The content is 3 to 5 mass % in still yet another embodiment of the present invention.

Furthermore, the compounds represented by the general formula (I-2) are preferably compounds selected from the group of compounds represented by formula (3.1) to formula (3.4) and more preferably a compound represented by formula (3.1), formula (3.3), or formula (3.4). In particular, the compound represented by the formula (3.2) is preferably used because the response speed of the liquid crystal composition of the present invention is considerably improved. When high Tni is required rather than the response speed, the compound represented by the formula (3.3) or the compound represented by the formula (3.4) is preferably used. The content of the compound represented by the formula (3.3) or the compound represented by the formula (3.4) is preferably less than 20% to increase the solubility at low temperature.

Furthermore, the compounds represented by the general formula (I-2) are preferably compounds selected from the group of compounds represented by formula (3.1) to formula (3.4) and more preferably a compound represented by formula (3.1), a compound represented by formula (3.3), and/or a compound represented by formula (3.4).

[Chem. 22]

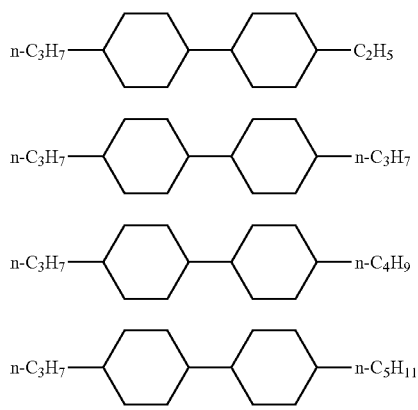

In the liquid crystal composition of the present invention, the content of the compound represented by the formula (3.3) is preferably 2 mass % or more and 40 mass % or less relative to the total mass of the liquid crystal composition of the present invention.

Furthermore, the compounds represented by the general formula (I) are preferably compounds selected from the group of compounds represented by general formula (I-3).

[Chem. 23]

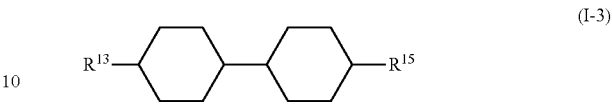

(In the formula, $R^{13}$ represents an alkyl group having 1 to 5 carbon atoms and $R^{15}$ represents an alkoxy group having 1 to 4 carbon atoms.)

Although the number of compounds that can be combined with each other is not particularly limited, a plurality of the compounds represented by the general formula (I-3) can be used in combination in accordance with the required characteristics such as solubility at low temperature, transition temperature, electrical reliability, and double refractive index. For example, the number of the compounds used is one in one embodiment of the present invention. The number of the compounds is two in another embodiment of the present invention. The number of the compounds is three in still another embodiment of the present invention.

In the liquid crystal composition of the present invention, the content of the compounds represented by the general formula (I-3) needs to be appropriately adjusted in accordance with the required characteristics such as solubility at low temperature, transition temperature, electrical reliability, double refractive index, process compatibility, drop marks, image sticking, and dielectric anisotropy.

For example, the content of the compounds is 3 mass % relative to the total mass of the liquid crystal composition of the present invention in one embodiment of the present invention. The content is 4 to 60 mass % in another embodiment of the present invention. The content is 15 to 60 mass % in still another embodiment of the present invention. The content is 25 to 60 mass % in still yet another embodiment of the present invention. The content is 30 to 60 mass % in still yet another embodiment of the present invention. The content is 35 to 60 mass % in still yet another embodiment of the present invention. The content is 38 to 60 mass % in still yet another embodiment of the present invention. The content is 40 to 60 mass % in still yet another embodiment of the present invention. The content is 42 to 60 mass % in still yet another embodiment of the present invention. The content is 45 to 60 mass % in still yet another embodiment of the present invention. The content is 47 to 60 mass % in still yet another embodiment of the present invention. The content is 50 to 60 mass % in still yet another embodiment of the present invention.

Furthermore, for example, the content of the compounds is 3 to 60 mass % relative to the total mass of the liquid crystal composition of the present invention in one embodiment of the present invention. The content is 3 to 55 mass % in another embodiment of the present invention. The content is 3 to 45 mass % in still another embodiment of the present invention. The content is 3 to 40 mass % in still yet another embodiment of the present invention. The content is 3 to 30 mass % in still yet another embodiment of the present invention. The content is 3 to 20 mass % in still yet another embodiment of the present invention. The content is 3 to 15 mass % in still yet another embodiment of the present invention. The content is 3 to 5 mass % in still yet another embodiment of the present invention.

When an importance is given to the solubility at low temperature, a higher effect is produced by increasing the content. On the other hand, when an importance is given to the response speed, a higher effect is produced by decreasing the content. In order to suppress drop marks and image sticking, the content is preferably set to be middle.

Furthermore, the compounds represented by the general formula (I-3) are preferably compounds selected from the group of compounds represented by formula (4.1) to formula (4.3) and more preferably a compound represented by formula (4.3).

[Chem. 24]

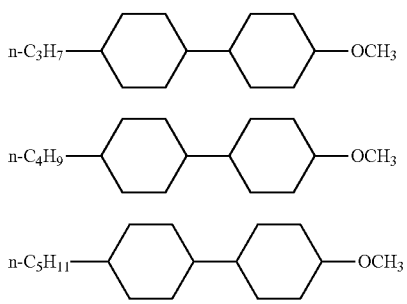

The content of the compound represented by the formula (4.3) is preferably 2 mass % or more and 30 mass % or less relative to the total amount of the liquid crystal composition of the present invention.

Furthermore, the compounds represented by the general formula (I) are preferably compounds selected from the group of compounds represented by general formula (I-4).

[Chem. 25]

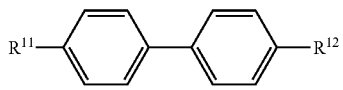

(In the formula, $R^{11}$ and $R^{12}$ each independently represent an alkyl group having 1 to 5 carbon atoms, an alkenyl group having 4 or 5 carbon atoms, or an alkoxy group having 1 to 4 carbon atoms.)

Although the number of compounds that can be combined with each other is not particularly limited, a plurality of the compounds represented by the general formula (I-4) can be used in combination in accordance with the required characteristics such as solubility at low temperature, transition temperature, electrical reliability, and double refractive index. For example, the number of the compounds used is one in one embodiment of the present invention. The number of the compounds is two in another embodiment of the present invention.

In the liquid crystal composition of the present invention, the content of the compounds represented by the general formula (I-4) needs to be appropriately adjusted in accordance with the required characteristics such as solubility at low temperature, transition temperature, electrical reliability, double refractive index, process compatibility, drop marks, image sticking, and dielectric anisotropy.

For example, the content of the compounds is 3 to 50 mass % relative to the total mass of the liquid crystal composition of the present invention in one embodiment of the present invention. The content is 5 to 50 mass % in another embodiment of the present invention. The content is 6 to 50 mass % in still another embodiment of the present invention. The content is 8 to 50 mass % in still yet another embodiment of the present invention. The content is 10 to 50 mass % in still yet another embodiment of the present invention. The content is 12 to 50 mass % in still yet another embodiment of the present invention. The content is 15 to 50 mass % in still yet another embodiment of the present invention. The content is 20 to 50 mass % in still yet another embodiment of the present invention. The content is 25 to 50 mass % in still yet another embodiment of the present invention. The content is 30 to 50 mass % in still yet another embodiment of the present invention. The content is 35 to 50 mass % in still yet another embodiment of the present invention. The content is 40 to 50 mass % in still yet another embodiment of the present invention.

Furthermore, for example, the content of the compounds is 3 to 50 mass % relative to the total mass of the liquid crystal composition of the present invention in one embodiment of the present invention. The content is 3 to 40 mass % in another embodiment of the present invention. The content is 3 to 35 mass % in still another embodiment of the present invention. The content is 3 to 30 mass % in still yet another embodiment of the present invention. The content is 3 to 20 mass % in still yet another embodiment of the present invention. The content is 3 to 15 mass % in still yet another embodiment of the present invention. The content is 3 to 10 mass % in still yet another embodiment of the present invention. The content is 3 to 5 mass % in still yet another embodiment of the present invention.

When an importance is given to a high double refractive index, a higher effect is produced by increasing the content. On the other hand, when an importance is given to high Tni, a higher effect is produced by decreasing the content. In order to suppress drop marks and image sticking, the content is preferably set to be middle.

Furthermore, the compounds represented by the general formula (I-4) are preferably compounds selected from the group of compounds represented by formula (5.1) to formula (5.4) and more preferably compounds represented by formula (5.2) to formula (5.4).

[Chem. 26]

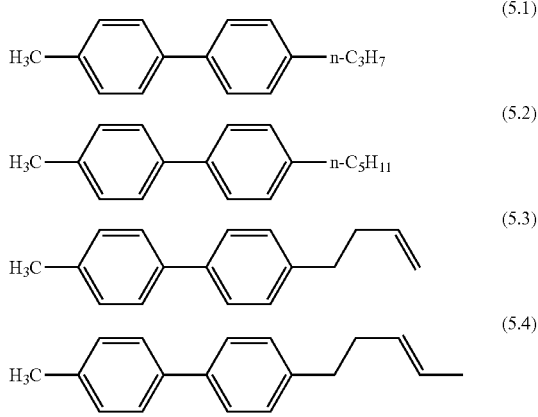

The content of the compound represented by the formula (5.3) is preferably 1 mass % or more and 30 mass % or less, more preferably 2 mass % or more and 20 mass % or less, and more preferably 2 mass % or more and 10 mass % or less relative to the total mass of the liquid crystal composition of the present invention.

The content of the compound represented by the formula (5.4) is preferably 2 mass % or more and 30 mass % or less relative to the total mass of the liquid crystal composition of the present invention.

Furthermore, the compounds represented by the general formula (I) are preferably compounds selected from the group of compounds represented by general formula (I-5).

[Chem. 27]

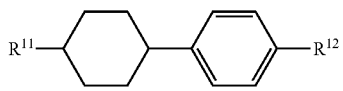
(I-5)

(In the formula, $R^{11}$ represents an alkyl group having 1 to 5 carbon atoms, an alkenyl group having 2 to 5 carbon atoms, or an alkoxy group having 1 to 4 carbon atoms; and $R^{12}$ represents an alkyl group having 1 to 5 carbon atoms, an alkenyl group having 4 or 5 carbon atoms, or an alkoxy group having 1 to 4 carbon atoms.)

Although the number of compounds that can be combined with each other is not particularly limited, a plurality of the compounds represented by the general formula (I-5) can be used in combination in accordance with the required characteristics such as solubility at low temperature, transition temperature, electrical reliability, and double refractive index. For example, the number of the compounds used is one in one embodiment of the present invention. The number of the compounds is two in another embodiment of the present invention.

In the liquid crystal composition of the present invention, the content of the compounds represented by the general formula (I-5) needs to be appropriately adjusted in accordance with the required characteristics such as solubility at low temperature, transition temperature, electrical reliability, double refractive index, process compatibility, drop marks, image sticking, and dielectric anisotropy.

For example, the content of the compounds is 1 to 50 mass % relative to the total mass of the liquid crystal composition of the present invention in one embodiment of the present invention. The content is 5 to 50 mass % in another embodiment of the present invention. The content is 8 to 50 mass % in still another embodiment of the present invention. The content is 11 to 50 mass % in still yet another embodiment of the present invention. The content is 13 to 50 mass % in still yet another embodiment of the present invention. The content is 15 to 50 mass % in still yet another embodiment of the present invention. The content is 17 to 50 mass % in still yet another embodiment of the present invention. The content is 20 to 50 mass % in still yet another embodiment of the present invention. The content is 25 to 50 mass % in still yet another embodiment of the present invention. The content is 30 to 50 mass % in still yet another embodiment of the present invention. The content is 35 to 50 mass % in still yet another embodiment of the present invention. The content is 40 to 50 mass % in still yet another embodiment of the present invention.

Furthermore, for example, the content of the compounds is 1 to 50% relative to the total mass of the liquid crystal composition of the present invention in one embodiment of the present invention. The content is 1 to 40% in another embodiment of the present invention. The content is 1 to 35% in still another embodiment of the present invention. The content is 1 to 30% in still yet another embodiment of the present invention. The content is 1 to 20% in still yet another embodiment of the present invention. The content is 1 to 15% in still yet another embodiment of the present invention. The content is 1 to 10% in still yet another embodiment of the present invention. The content is 1 to 5% in still yet another embodiment of the present invention.

When an importance is given to the solubility at low temperature, a higher effect is produced by increasing the content. On the other hand, when an importance is given to the response speed, a higher effect is produced by decreasing the content. In order to suppress drop marks and image sticking, the content is preferably set to be middle.

Furthermore, the compounds represented by the general formula (I-5) are preferably compounds selected from the group of compounds represented by formula (6.1) to formula (6.6) and more preferably compounds represented by formula (6.3), formula (6.4), and formula (6.6).

[Chem. 28]

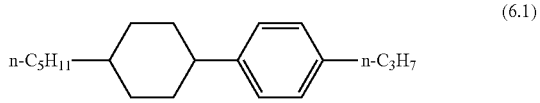
(6.1)

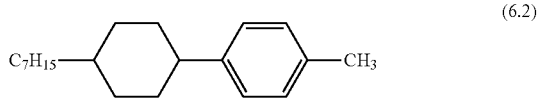
(6.2)

(6.3)

(6.4)

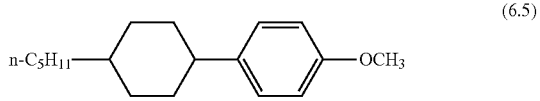
(6.5)

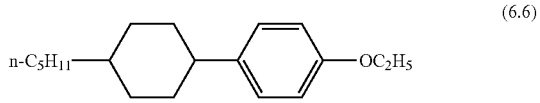
(6.6)

The content of the compound represented by the formula (6.3) is preferably 2 mass % or more and 30 mass % or less, more preferably 4 mass % or more and 25 mass % or less, and more preferably 6 mass % or more and 20 mass % or less relative to the total mass of the liquid crystal composition of the present invention.

The liquid crystal composition of the present invention may further contain compounds represented by formula (6.7) and formula (6.8) as the compounds represented by the general formula (I-5).

[Chem. 29]

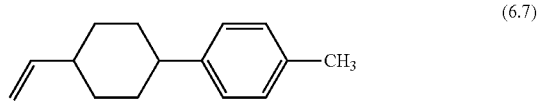
(6.7)

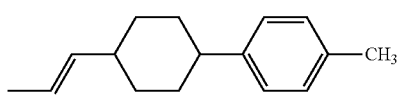

(6.8)

The content of the compound represented by the formula (6.7) is preferably adjusted in accordance with the required characteristics such as solubility at low temperature, transition temperature, electrical reliability, and double refractive index. The content of the compound is preferably 2 mass % or more, more preferably 3 mass % or more, more preferably 5 mass % or more, and particularly preferably 7 mass % or more relative to the total mass of the liquid crystal composition of the present invention.

Furthermore, the compounds represented by the general formula (I) are preferably compounds selected from the group of compounds represented by general formula (I-6).

[Chem. 30]

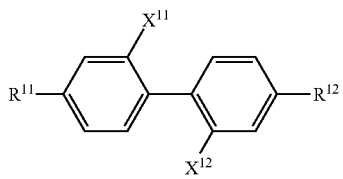

(I-6)

(In the formula, $R^{11}$ and $R^{12}$ each independently represent an alkyl group having 1 to 5 carbon atoms, an alkenyl group having 4 or 5 carbon atoms, or an alkoxy group having 1 to 4 carbon atoms; and $X^{11}$ and $X^{12}$ each independently represent a fluorine atom or a hydrogen atom, and one of $X^{11}$ and $X^{12}$ represents a fluorine atom.)

The content of the compounds represented by the general formula (I-6) is preferably 2 mass % or more and 30 mass % or less, more preferably 4 mass % or more and 30 mass % or less, more preferably 5 mass % or more and 30 mass % or less, more preferably 6 mass % or more and 30 mass % or less, more preferably 9 mass % or more and 30 mass % or less, more preferably 12 mass % or more and 30 mass % or less, more preferably 14 mass % or more and 30 mass % or less, more preferably 16 mass % or more and 30 mass % or less, more preferably 18 mass % or more and 25 mass % or less, more preferably 20 mass % or more and 24 mass % or less, and particularly preferably 22 mass % or more and 23 mass % or less relative to the total mass of the liquid crystal composition of the present invention.

Furthermore, the compounds represented by the general formula (I-6) are preferably a compound represented by formula (7.1).

[Chem. 31]

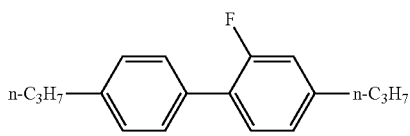

(7.1)

Furthermore, the compounds represented by the general formula (I) are preferably compounds selected from the group of compounds represented by general formula (I-7).

[Chem. 32]

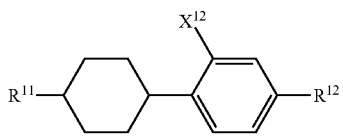

(I-7)

(In the formula, $R^{11}$ and $R^{12}$ each independently represent an alkyl group having 1 to 5 carbon atoms, an alkenyl group having 2 to 5 carbon atoms, or an alkoxy group having 1 to 4 carbon atoms; and $X^{12}$ represents a fluorine atom or a chlorine atom.)

The content of the compounds represented by the general formula (I-7) is preferably 1 mass % or more and 30 mass % or less, more preferably 2 mass % or more and 30 mass % or less, more preferably 3 mass % or more and 30 mass % or less, more preferably 4 mass % or more and 30 mass % or less, more preferably 6 mass % or more and 30 mass % or less, more preferably 8 mass % or more and 30 mass % or less, more preferably 10 mass % or more and 30 mass % or less, more preferably 12 mass % or more and 30 mass % or less, more preferably 15 mass % or more and 25 mass % or less, more preferably 18 mass % or more and 24 mass % or less, and particularly preferably 21 mass % or more and 22 mass % or less relative to the total mass of the liquid crystal composition of the present invention.

The compounds represented by the general formula (I-7) are preferably a compound represented by formula (8.1).

[Chem. 33]

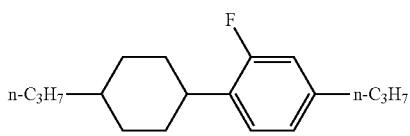

(8.1)

Furthermore, the compounds represented by the general formula (I) are preferably compounds selected from the group of compounds represented by general formula (I-8).

[Chem. 34]

(I-8)

(In the formula, $R^{16}$ and $R^{17}$ each independently represent an alkenyl group having 2 to 5 carbon atoms.)

Although the number of compounds that can be combined with each other is not particularly limited, one to three of the plurality of compounds represented by the general formula (I-8) can be used in combination in accordance with the required characteristics such as solubility at low temperature, transition temperature, electrical reliability, and double refractive index. The content of the compounds represented by the general formula (I-8) is appropriately adjusted in accordance with the required characteristics such as solubility at low temperature, transition temperature, electrical reliability, double refractive index, process compatibility, drop marks, image sticking, and dielectric anisotropy. The content of the compounds is preferably 5 mass % or more and 65 mass % or less, more preferably 10 mass % or more and 65 mass % or less, more preferably 15 mass % or more and 65 mass % or less, more preferably 20 mass % or more and 65 mass % or less, more preferably 25 mass % or more and 65 mass % or less, more preferably 30 mass % or more and 65 mass % or less, more preferably 35 mass % or more and 65 mass % or less, more preferably 40 mass % or more and 65 mass % or less, more preferably 45 mass % or more and 60 mass % or less, more preferably 50 mass % or more and 58 mass % or less, and particularly preferably 55 mass % or more and 56 mass % or less relative to the total mass of the liquid crystal composition of the present invention.

Furthermore, the compounds represented by the general formula (I-8) are preferably compounds selected from the group of compounds represented by formula (9.1) to formula (9.10) and more preferably compounds represented by formula (9.2), formula (9.4), and formula (9.7).

[Chem. 35]

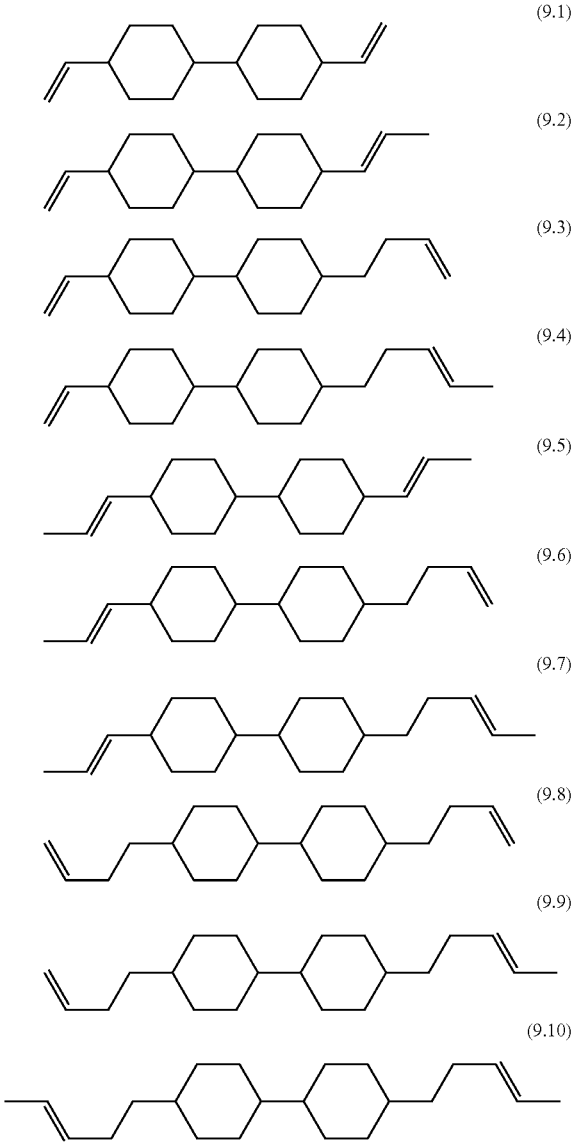

Furthermore, the compounds represented by the general formula (L) are, for example, preferably compounds selected from compounds represented by general formula (II).

[Chem. 36]

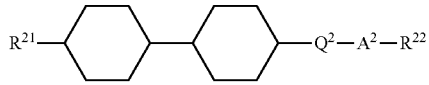

($R^{21}$ and $R^{22}$ each independently represent an alkenyl group having 2 to 5 carbon atoms, an alkyl group having 1 to 5 carbon atoms, or an alkoxy group having 1 to 4 carbon atoms; $A^2$ represents a 1,4-cyclohexylene group or a 1,4-phenylene group; and $Q^2$ represents a single bond, —COO—, —$CH_2$—$CH_2$—, or —$CF_2O$—.)

Although the number of compounds that can be combined with each other is not particularly limited, a plurality of the compounds represented by the general formula (II) can be used in combination in accordance with the required characteristics such as solubility at low temperature, transition temperature, electrical reliability, and double refractive index. For example, the number of the compounds used is one in one embodiment of the present invention. The number of the compounds is two in another embodiment of the present invention. The number of the compounds is three in still another embodiment of the present invention. The number of the compounds is four or more in still yet another embodiment of the present invention.

In the liquid crystal composition of the present invention, the content of the compounds represented by the general formula (II) needs to be appropriately adjusted in accordance with the required characteristics such as solubility at low temperature, transition temperature, electrical reliability, double refractive index, process compatibility, drop marks, image sticking, and dielectric anisotropy.

For example, the content of the compounds is 3 to 50 mass % relative to the total mass of the liquid crystal composition of the present invention in one embodiment of the present invention. The content is 5 to 50 mass % in another embodiment of the present invention. The content is 7 to 50 mass % in still another embodiment of the present invention. The content is 10 to 50 mass % in still yet another embodiment of the present invention. The content is 14 to 50 mass % in still yet another embodiment of the present invention. The content is 16 to 50 mass % in still yet another embodiment of the present invention. The content is 20 to 50 mass % in still yet another embodiment of the present invention. The content is 23 to 50 mass % in still yet another embodiment of the present invention. The content is 26 to 50 mass % in still yet another embodiment of the present invention. The content is 30 to 50 mass % in still yet another embodiment of the present invention. The content is 35 to 50 mass % in still yet another embodiment of the present invention. The content is 40 to 50 mass % in still yet another embodiment of the present invention.

Furthermore, for example, the content of the compounds is 3 to 50 mass % relative to the total mass of the liquid crystal composition of the present invention in one embodiment of the present invention. The content is 3 to 40 mass % in another embodiment of the present invention. The content is 3 to 35 mass % in still another embodiment of the present invention. The content is 3 to 30 mass % in still yet another embodiment of the present invention. The content is 3 to 20 mass % in still yet another embodiment of the present invention. The content is 3 to 15 mass % in still yet another embodiment of the present invention. The content is 3 to 10 mass % in still yet another embodiment of the present invention. The content is 3 to 5 mass % in still yet another embodiment of the present invention.

The compounds represented by the general formula (II) are, for example, preferably compounds selected from the group of compounds represented by general formula (II-1).

[Chem. 37]

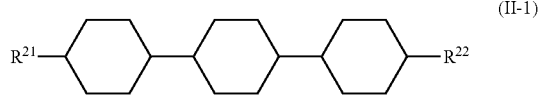

(II-1)

($R^{21}$ and $R^{22}$ each independently represent an alkenyl group having 2 to 5 carbon atoms, an alkyl group having 1 to 5 carbon atoms, or an alkoxy group having 1 to 4 carbon atoms.)

The content of the compounds represented by the general formula (II-1) is preferably adjusted in accordance with the required characteristics such as solubility at low temperature, transition temperature, electrical reliability, and double refractive index. The content of the compounds is preferably 4 mass % or more and 24 mass % or less, more preferably 8 mass % or more and 18 mass % or less, and more preferably 12 mass % or more and 14 mass % or less.

Furthermore, the compounds represented by the general formula (II-1) are, for example, preferably compounds represented by formula (10.1) and formula (10.2).

[Chem. 38]

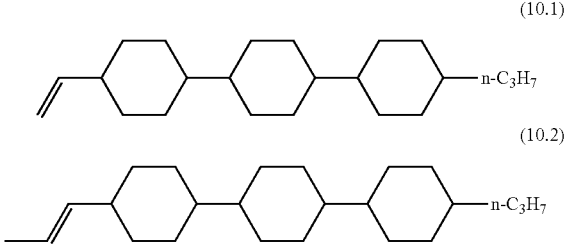

(10.1)

(10.2)

Furthermore, the compounds represented by the general formula (II) are, for example, preferably compounds selected from the group of compounds represented by general formula (II-2).

[Chem. 39]

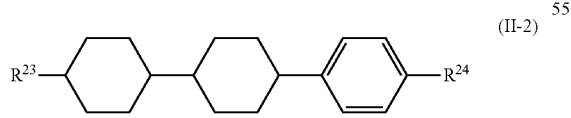

(II-2)

($R^{23}$ represents an alkenyl group having 2 to 5 carbon atoms, and $R^{24}$ represents an alkyl group having 1 to 5 carbon atoms or an alkoxy group having 1 to 4 carbon atoms.)

Although the number of compounds that can be combined with each other is not particularly limited, a plurality of the compounds represented by the general formula (II-2) can be used in combination in accordance with the required characteristics such as solubility at low temperature, transition temperature, electrical reliability, and double refractive index. For example, the number of the compounds used is one in one embodiment of the present invention. The number of the compounds is two or more in another embodiment of the present invention.

In the liquid crystal composition of the present invention, the content of the compounds represented by the general formula (II-2) needs to be appropriately adjusted in accordance with the required characteristics such as solubility at low temperature, transition temperature, electrical reliability, double refractive index, process compatibility, drop marks, image sticking, and dielectric anisotropy.

For example, the content of the compounds is 3 to 50 mass % relative to the total mass of the liquid crystal composition of the present invention in one embodiment of the present invention. The content is 5 to 50 mass % in another embodiment of the present invention. The content is 7 to 50 mass % in still another embodiment of the present invention. The content is 10 to 50 mass % in still yet another embodiment of the present invention. The content is 14 to 50 mass % in still yet another embodiment of the present invention. The content is 16 to 50 mass % in still yet another embodiment of the present invention. The content is 20 to 50 mass % in still yet another embodiment of the present invention. The content is 23 to 50 mass % in still yet another embodiment of the present invention. The content is 26 to 50 mass % in still yet another embodiment of the present invention. The content is 30 to 50 mass % in still yet another embodiment of the present invention. The content is 35 to 50 mass % in still yet another embodiment of the present invention. The content is 40 to 50 mass % in still yet another embodiment of the present invention.

Furthermore, for example, the content of the compounds is 3 to 50 mass % relative to the total mass of the liquid crystal composition of the present invention in one embodiment of the present invention. The content is 3 to 40 mass % in another embodiment of the present invention. The content is 3 to 35 mass % in still another embodiment of the present invention. The content is 3 to 30 mass % in still yet another embodiment of the present invention. The content is 3 to 20 mass % in still yet another embodiment of the present invention. The content is 3 to 15 mass % in still yet another embodiment of the present invention. The content is 3 to 10 mass % in still yet another embodiment of the present invention. The content is 3 to 5 mass % in still yet another embodiment of the present invention.

Furthermore, the compounds represented by the general formula (II-2) are, for example, preferably compounds represented by formula (11.1) to formula (11.3).

[Chem. 40]

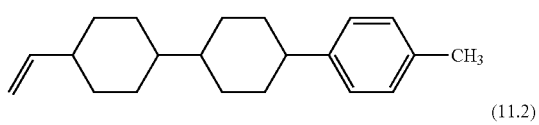

(11.1)

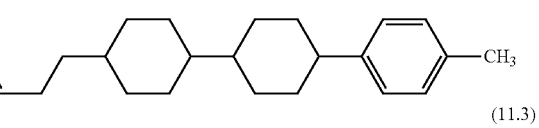

(11.2)

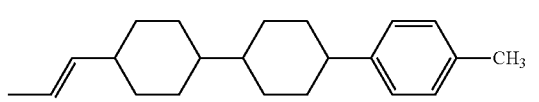

(11.3)

The liquid crystal composition may contain the compound represented by the formula (11.1), the compound represented by the formula (11.2), both the compounds represented by the formula (11.1) and the formula (11.2), or all the compounds represented by the formula (11.1) to the formula (11.3) in accordance with the required characteristics such as solubility at low temperature, transition temperature, electrical reliability, and double refractive index. The content of the compound represented by the formula (11.1) or the formula (11.2) is preferably 3 mass % or more and 40 mass % or less, more preferably 5 mass % or more and 35 mass % or less, more preferably 5 mass % or more and 30 mass % or less, particularly preferably 5 mass % or more and 25 mass % or less, and most preferably 5 mass % or more and 20 mass % or less relative to the total mass of the liquid crystal composition of the present invention.

The content of the compound represented by the formula (11.1) is preferably 1 mass % or more and 40 mass % or less, more preferably 1 mass % or more and 25 mass % or less, more preferably 1 mass % or more and 20 mass % or less, more preferably 1 mass % or more and 15 mass % or less, and particularly preferably 3 mass % or more and 10 mass % or less relative to the total mass of the liquid crystal composition of the present invention.

Examples of the content in the particularly preferable range include 3 mass % or more and 8 mass % or less, 3 mass % or more and 5 mass % or less, 3 mass % or more and 4 mass % or less, 4 mass % or more and 10 mass % or less, 5 mass % or more and 10 mass % or less, 8 mass % or more and 10 mass % or less, and 9 mass % or more and 10 mass % or less.

The content of the compound represented by the formula (11.2) is preferably 3 mass % or more and 40 mass % or less, more preferably 3 mass % or more and 35 mass % or less, more preferably 3 mass % or more and 30 mass % or less, more preferably 3 mass % or more and 25 mass % or less, and particularly preferably 3 mass % or more and 20 mass % or less relative to the total mass of the liquid crystal composition of the present invention.

When both the compound represented by the formula (11.1) and the compound represented by the formula (11.2) are contained, the ratio of the total mass of both the compounds to the total mass of the liquid crystal composition of the present invention is preferably 10 mass % or more and 45 mass % or less.

Furthermore, the compounds represented by the general formula (II) are, for example, preferably compounds selected from the group of compounds represented by general formula (II-3).

[Chem. 41]

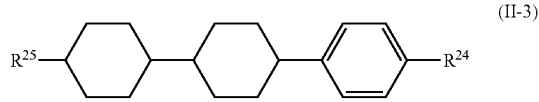
(II-3)

($R^{25}$ represents an alkyl group having 1 to 5 carbon atoms and $R^{24}$ represents an alkyl group having 1 to 5 carbon atoms or an alkoxy group having 1 to 4 carbon atoms.)

Although the number of compounds that can be combined with each other is not particularly limited, one to three of the plurality of compounds represented by the general formula (II-3) are preferably contained in accordance with the required characteristics such as solubility at low temperature, transition temperature, electrical reliability, and double refractive index.

The content of the compounds represented by the general formula (II-3) needs to be appropriately adjusted in accordance with the required characteristics such as solubility at low temperature, transition temperature, electrical reliability, double refractive index, process compatibility, drop marks, image sticking, and dielectric anisotropy. An example of the preferable content of the compounds is 2 to 45 mass % relative to the total mass of the liquid crystal composition of the present invention. Examples of the more preferable content of the compounds include 5 to 45 mass %, 8 to 45 mass %, 11 to 45 mass %, 14 to 45 mass %, 17 to 45 mass %, 20 to 45 mass %, 23 to 45 mass %, 26 to 45 mass %, and 29 to 45 mass %; and 2 to 45 mass %, 2 to 40 mass %, 2 to 35 mass %, 2 to 30 mass %, 2 to 25 mass %, 2 to 20 mass %, 2 to 15 mass %, and 2 to 10 mass %.

Furthermore, the compounds represented by the general formula (II-3) are, for example, preferably compounds represented by formula (12.1) to formula (12.3).

[Chem. 42]

(12.1)

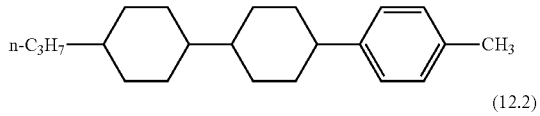
(12.2)

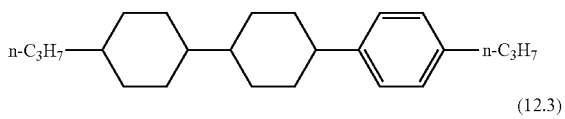
(12.3)

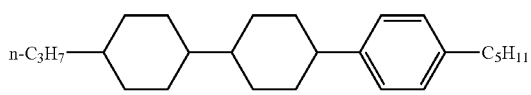

The liquid crystal composition may contain the compound represented by the formula (12.1), the compound represented by the formula (12.2), or both the compounds represented by the formula (12.1) and the formula (12.2) in accordance with the required characteristics such as solubility at low temperature, transition temperature, electrical reliability, and double refractive index. The content of the compound represented by the formula (12.1) or the formula (12.2) is preferably 3 mass % or more and 40 mass % or less relative to the total mass of the liquid crystal composition of the present invention. The content of the compound represented by the formula (12.2) is preferably 3 mass % or more and 40 mass % or less relative to the total mass of the liquid crystal composition of the present invention. When both the compound represented by the formula (12.1) and the compound represented by the formula (12.2) are contained, the ratio of the total mass of both the compounds to the total mass of the liquid crystal composition of the present invention is preferably 15 mass % or more and 45 mass % or less.

The content of the compound represented by the formula (12.3) is preferably 0.05 mass % or more and 2 mass % or less relative to the total mass of the liquid crystal composition of the present invention. The compound represented by the formula (12.3) may be an optically active compound.

Furthermore, the compounds represented by the general formula (II-3) are, for example, preferably compounds selected from the group of compounds represented by general formula (II-3-1).

[Chem. 43]

(II-3-1)

($R^{25}$ represents an alkyl group having 1 to 5 carbon atoms and $R^{26}$ represents an alkoxy group having 1 to 4 carbon atoms.)

Although the number of compounds that can be combined with each other is not particularly limited, one to three of the plurality of compounds represented by the general formula (II-3-1) are preferably contained in accordance with the required characteristics such as solubility at low temperature, transition temperature, electrical reliability, and double refractive index.

The content of the compounds represented by the general formula (II-3-1) is preferably adjusted in accordance with the required characteristics such as solubility at low temperature, transition temperature, electrical reliability, and double refractive index. The content of the compounds is preferably 1 mass % or more and 24 mass % or less, more preferably 4 mass % or more and 18 mass % or less, and more preferably 8 mass % or more and 14 mass % or less.

Furthermore, the compounds represented by the general formula (II-3-1) are, for example, preferably compounds represented by formula (13.1) to formula (13.4) and particularly preferably a compound represented by formula (13.3).

[Chem. 44]

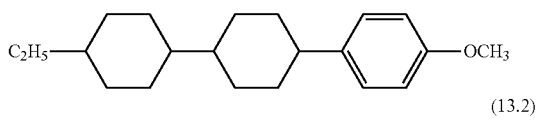

(13.1)

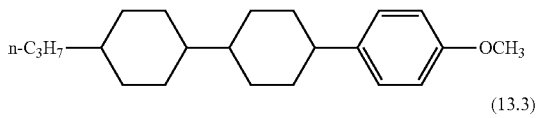

(13.2)

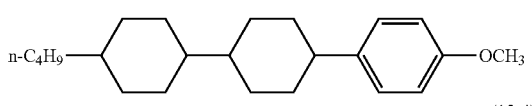

(13.3)

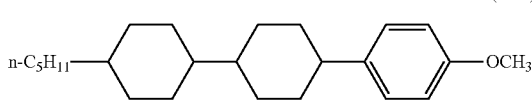

(13.4)

Furthermore, the compounds represented by the general formula (II) are, for example, preferably compounds selected from the group of compounds represented by general formula (II-4).

[Chem. 45]

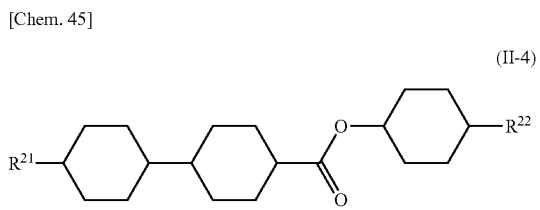

(II-4)

($R^{21}$ and $R^{22}$ each independently represent an alkenyl group having 2 to 5 carbon atoms, an alkyl group having 1 to 5 carbon atoms, or an alkoxy group having 1 to 4 carbon atoms.)

One or more of the compounds may be contained and are preferably suitably combined with each other in accordance with the required characteristics. Although the number of compounds that can be combined with each other is not particularly limited, one or two of the plurality of compounds represented by the general formula (II-4) are preferably contained and one to three of the plurality of compounds represented by the general formula (II-4) are particularly preferably contained in accordance with the required characteristics such as solubility at low temperature, transition temperature, electrical reliability, and double refractive index.

The content of the compounds represented by the general formula (II-4) is preferably 1 mass % or more and 15 mass % or less, more preferably 2 mass % or more and 15 mass % or less, more preferably 3 mass % or more and 15 mass % or less, more preferably 4 mass % or more and 12 mass % or less, and particularly preferably 5 mass % or more and 7 mass % or less relative to the total mass of the liquid crystal composition of the present invention.

Furthermore, the compounds represented by the general formula (II-4) are, for example, preferably compounds represented by formula (14.1) to formula (14.5) and particularly preferably a compound represented by formula (14.2) or formula (14.5).

[Chem. 46]

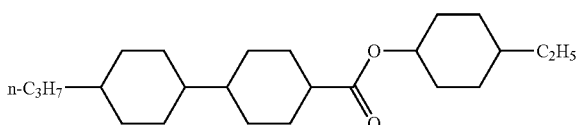

(14.1)

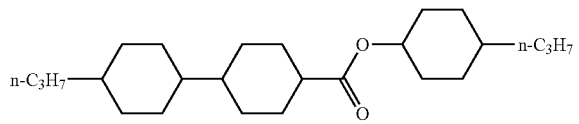

(14.2)

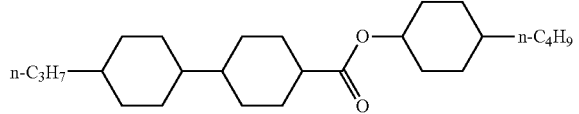

(14.3)

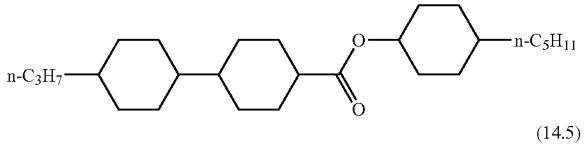

(14.4)

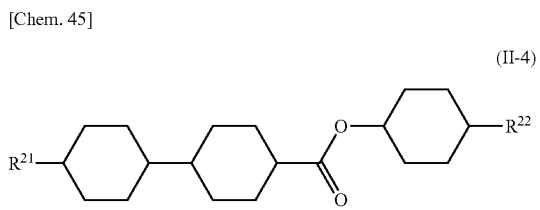

(14.5)

Furthermore, the compounds represented by the general formula (L) are preferably compounds selected from the group of compounds represented by general formula (III).

[Chem. 47]

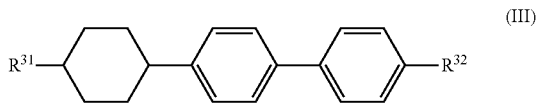
(III)

($R^{31}$ and $R^{32}$ each independently represent an alkenyl group having 2 to 5 carbon atoms, an alkyl group having 1 to 5 carbon atoms, or an alkoxy group having 1 to 4 carbon atoms.)

The content of the compounds represented by the general formula (III) is preferably 3 mass % or more and 25 mass % or less, more preferably 6 mass % or more and 20 mass % or less, and more preferably 8 mass % or more and 15 mass % or less relative to the total mass of the liquid crystal composition of the present invention in consideration of the required solubility and double refractive index and the like.

Furthermore, the compounds represented by the general formula (III) are, for example, preferably a compound represented by formula (15.1) or formula (15.2) and particularly preferably a compound represented by formula (15.1).

[Chem. 48]

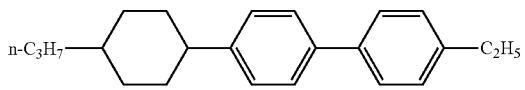
(15.1)

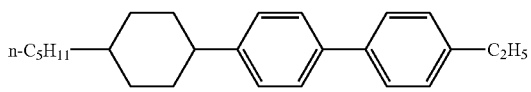
(15.2)

Furthermore, the compounds represented by the general formula (III) are preferably compounds selected from the group of compounds represented by general formula (III-1).

[Chem. 49]

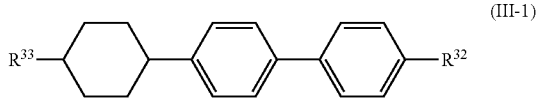
(III-1)

($R^{33}$ represents an alkenyl group having 2 to 5 carbon atoms and $R^{32}$ represents an alkyl group having 1 to 5 carbon atoms or an alkoxy group having 1 to 4 carbon atoms.)

The content of the compounds represented by the general formula (III-1) is preferably adjusted in accordance with the required characteristics such as solubility at low temperature, transition temperature, electrical reliability, and double refractive index. The content of the compounds is preferably 4 mass % or more and 23 mass % or less, more preferably 6 mass % or more and 18 mass % or less, and more preferably 10 mass % or more and 13 mass % or less.

The compounds represented by the general formula (III-1) are, for example, preferably a compound represented by formula (16.1) or formula (16.2).

[Chem. 50]

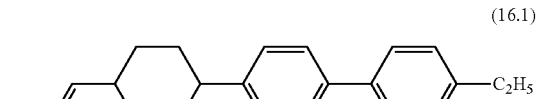
(16.1)

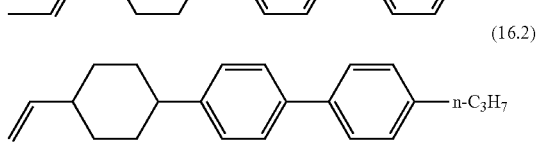
(16.2)

Furthermore, the compounds represented by the general formula (III) are preferably compounds selected from the group of compounds represented by general formula (III-2).

[Chem. 51]

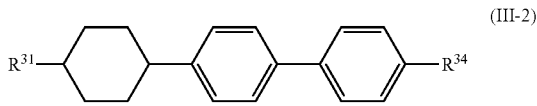
(III-2)

($R^{31}$ represents an alkyl group having 1 to 5 carbon atoms and $R^{34}$ represents an alkoxy group having 1 to 4 carbon atoms.)

The content of the compounds represented by the general formula (III-2) is preferably adjusted in accordance with the required characteristics such as solubility at low temperature, transition temperature, electrical reliability, and double refractive index. The content of the compounds is preferably 4 mass % or more and 23 mass % or less, more preferably 6 mass % or more and 18 mass % or less, and more preferably 10 mass % or more and 13 mass % or less.

Furthermore, the compounds represented by the general formula (III-2) are, for example, preferably compounds selected from the group of compounds represented by formula (17.1) to formula (17.3) and particularly preferably a compound represented by formula (17.3).

[Chem. 52]

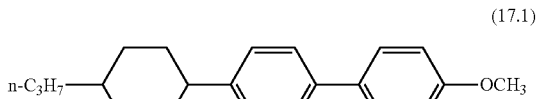
(17.1)

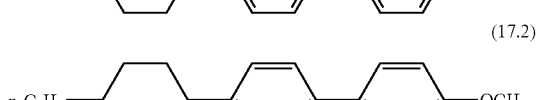
(17.2)

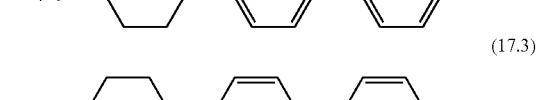
(17.3)

Furthermore, the compounds represented by the general formula (L) are preferably compounds selected from the group of compounds represented by general formula (IV).

[Chem. 53]

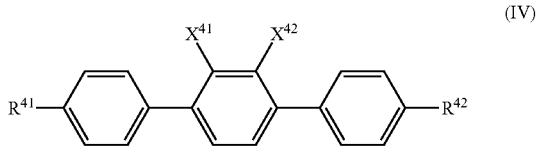
(IV)

(In the formula, $R^{41}$ and $R^{42}$ each independently represent an alkyl group having 1 to 5 carbon atoms or an alkenyl group having 2 to 5 carbon atoms, and $X^{41}$ and $X^{42}$ each independently represent a hydrogen atom or a fluorine atom.)

Although the number of compounds that can be combined with each other is not particularly limited, a plurality of the compounds represented by the general formula (IV) can be used in combination in accordance with the required characteristics such as solubility at low temperature, transition temperature, electrical reliability, and double refractive index. For example, the number of the compounds used is one in one embodiment of the present invention. The number of the compounds is two in another embodiment of the present invention. The number of the compounds is three in still another embodiment of the present invention. The number of the compounds is four in still yet another embodiment of the present invention. The number of the compounds is five in still yet another embodiment of the present invention. The number of the compounds is six or more in still yet another embodiment of the present invention.

Furthermore, the compounds represented by the general formula (IV) are preferably compounds selected from the group of compounds represented by general formula (IV-1).

[Chem. 54]

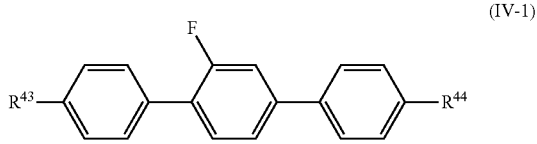

(IV-1)

(In the formula, $R^{43}$ and $R^{44}$ each independently represent an alkyl group having 1 to 5 carbon atoms.)

The content of the compounds represented by the general formula (IV-1) needs to be appropriately adjusted in accordance with the required characteristics such as solubility at low temperature, transition temperature, electrical reliability, double refractive index, process compatibility, drop marks, image sticking, and dielectric anisotropy.

For example, the content of the compounds is 1 to 40 mass % relative to the total mass of the liquid crystal composition of the present invention in one embodiment of the present invention. The content is 2 to 40 mass % in another embodiment of the present invention. The content is 4 to 40 mass % in still another embodiment of the present invention. The content is 6 to 40 mass % in still yet another embodiment of the present invention. The content is 8 to 40 mass % in still yet another embodiment of the present invention. The content is 10 to 40 mass % in still yet another embodiment of the present invention. The content is 12 to 40 mass % in still yet another embodiment of the present invention. The content is 15 to 40 mass % in still yet another embodiment of the present invention. The content is 18 to 40 mass % in still yet another embodiment of the present invention. The content is 21 to 40 mass % in still yet another embodiment of the present invention.

Furthermore, for example, the content of the compounds is 1 to 40 mass % relative to the total mass of the liquid crystal composition of the present invention in one embodiment of the present invention. The content is 1 to 30 mass % in another embodiment of the present invention. The content is 1 to 25 mass % in still another embodiment of the present invention. The content is 1 to 20 mass % in still yet another embodiment of the present invention. The content is 1 to 15 mass % in still yet another embodiment of the present invention. The content is 1 to 10 mass % in still yet another embodiment of the present invention. The content is 1 to 5 mass % in still yet another embodiment of the present invention. The content is 1 to 4 mass % in still yet another embodiment of the present invention.

Furthermore, the compounds represented by the general formula (IV-1) are, for example, preferably compounds represented by formula (18.1) to formula (18.9).

[Chem. 55]

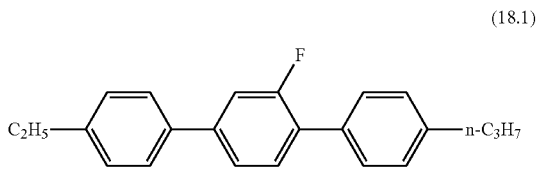

(18.1)

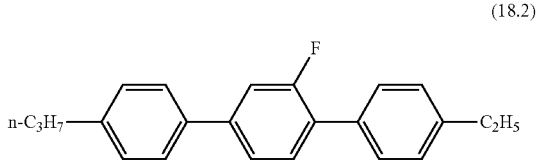

(18.2)

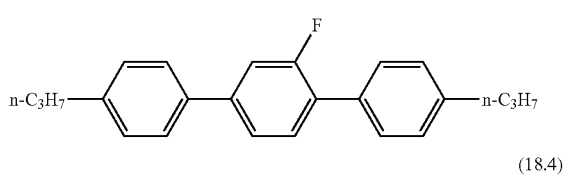

(18.3)

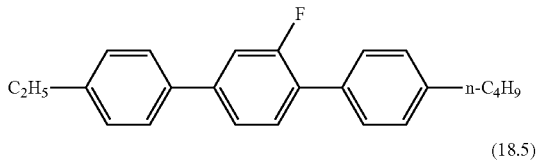

(18.4)

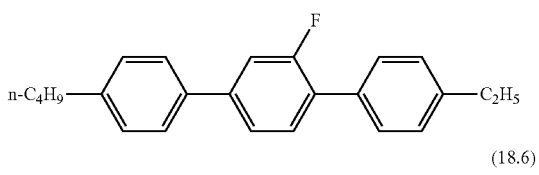

(18.5)

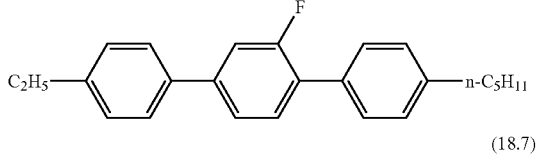

(18.6)

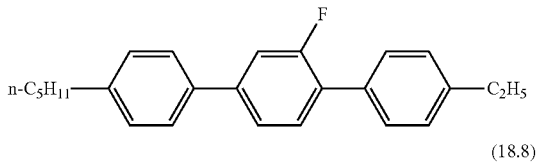

(18.7)

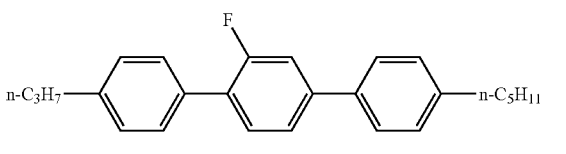

(18.8)

-continued (18.9)
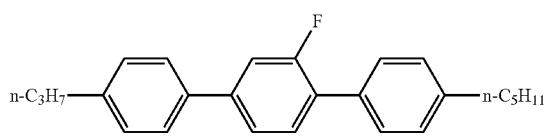

Although the number of compounds that can be combined with each other is not particularly limited, one to three of the compounds are preferably contained and one to four of the compounds are more preferably contained. A wide molecular-weight distribution of the compounds selected is also effective for the solubility. Therefore, for example, it is preferable to select one compound from the compounds represented by the formula (18.1) and the formula (18.2), one compound from the compounds represented by the formula (18.4) and the formula (18.5), one compound from the compounds represented by the formula (18.6) and the formula (18.7), and one compound from the compounds represented by the formula (18.8) and the formula (18.9) and to appropriately combine these compounds with each other. Among the compounds, the compounds represented by the formula (18.1), the formula (18.3), the formula (18.4), the formula (18.6), and the formula (18.9) are preferably contained.

Furthermore, the compounds represented by the general formula (IV) are, for example, preferably compounds selected from the group of compounds represented by general formula (IV-2).

[Chem. 56]

(IV-2)
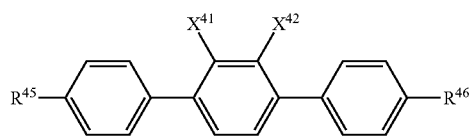

(In the formula, $R^{45}$ and $R^{46}$ each independently represent an alkyl group having 1 to 5 carbon atoms or an alkenyl group having 2 to 5 carbon atoms, but at least one of $R^{45}$ and $R^{46}$ represents an alkenyl group having 2 to 5 carbon atoms; and $X^{41}$ and $X^{42}$ each independently represent a hydrogen atom or a fluorine atom.)

Although the number of compounds that can be combined with each other is not particularly limited, a plurality of the compounds represented by the general formula (IV-2) can be used in combination in accordance with the required characteristics such as solubility at low temperature, transition temperature, electrical reliability, and double refractive index.

The content of the compounds represented by the general formula (IV-2) needs to be appropriately adjusted in accordance with the required characteristics such as solubility at low temperature, transition temperature, electrical reliability, double refractive index, process compatibility, drop marks, image sticking, and dielectric anisotropy. An example of the preferable content of the compounds is 0.5 to 40 mass % relative to the total mass of the liquid crystal composition of the present invention. Examples of the more preferable content of the compounds include 1 to 40 mass %, 2 to 40 mass %, 3 to 40 mass %, 5 to 40 mass %, 7 to 40 mass %, 9 to 40 mass %, 12 to 40 mass %, 15 to 40 mass %, and 20 to 40 mass %; and 1 to 40 mass %, 1 to 30 mass %, 1 to 25 mass %, 1 to 20 mass %, 1 to 15 mass %, 1 to 10 mass %, 1 to 5 mass %, and 1 to 4 mass %.

Furthermore, the compounds represented by the general formula (IV-2) are, for example, preferably compounds represented by formula (19.1) to formula (19.8) and particularly preferably a compound represented by formula (19.2).

[Chem. 57]

(19.1)
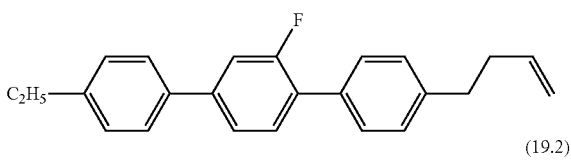

(19.2)
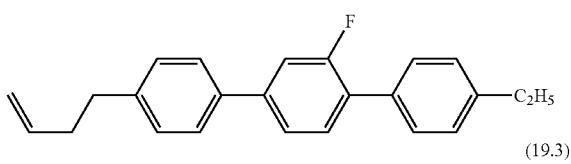

(19.3)
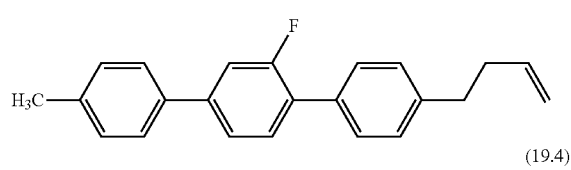

(19.4)
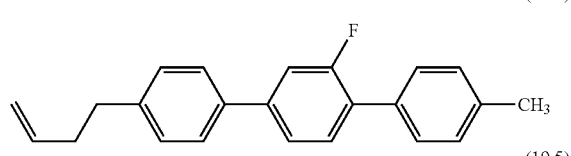

(19.5)
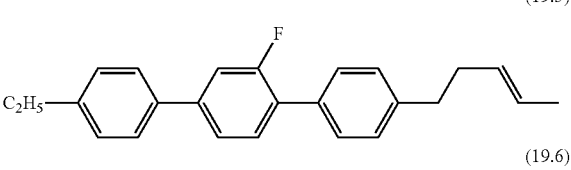

(19.6)
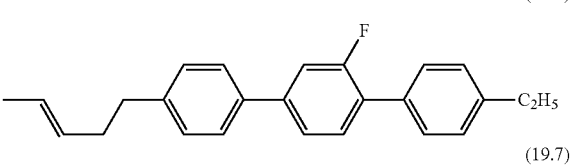

(19.7)
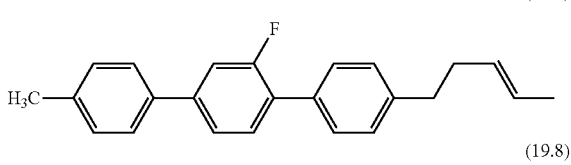

(19.8)
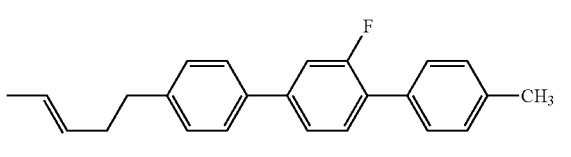

A wide molecular-weight distribution of the compounds selected as components of the liquid crystal composition is also effective for the solubility. Therefore, for example, it is preferable to select one compound from the compounds represented by the formula (19.1) and the formula (19.2), one compound from the compounds represented by the formula (19.3) and the formula (19.4), one compound from the compounds represented by the formula (19.5) and the formula (19.6), and one compound from the compounds represented by the formula (19.7) and the formula (19.8) and to appropriately combine these compounds with each other.

In the liquid crystal composition of the present invention, the content of the compound represented by the formula (19.2) is preferably 0.5 mass % or more and 15 mass % or less relative to the total mass of the liquid crystal composition of the present invention in consideration of solubility at low temperature, transition temperature, electrical reliability, and the like.

In the liquid crystal composition of the present invention, the content of the compound represented by the formula (19.4) is preferably 3 mass % or more and 25 mass % or less relative to the total mass of the liquid crystal composition of the present invention in consideration of solubility at low temperature, transition temperature, electrical reliability, and the like.

Furthermore, the compounds represented by the general formula (L) are preferably compounds selected from the group of compounds represented by general formula (V).

[Chem. 58]

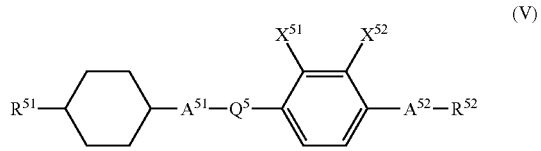

(V)

(In the formula, $R^{51}$ and $R^{52}$ each independently represent an alkyl group having 1 to 5 carbon atoms, an alkenyl group having 2 to 5 carbon atoms, or an alkoxy group having 1 to 4 carbon atoms; $A^{51}$ and $A^{52}$ each independently represent a 1,4-cyclohexylene group or a 1,4-phenylene group; $Q^5$ represents a single bond or —COO—; and $X^{51}$ and $X^{52}$ each independently represent a fluorine atom or a hydrogen atom.)

Although the number of compounds that can be combined with each other is not particularly limited, a plurality of the compounds represented by the general formula (V) can be used in combination in accordance with the required characteristics such as solubility at low temperature, transition temperature, electrical reliability, and double refractive index. For example, the number of the compounds used is one in one embodiment of the present invention. The number of the compounds is two in another embodiment of the present invention. The number of the compounds is three in still another embodiment of the present invention. The number of the compounds is four in still yet another embodiment of the present invention.

For example, the content of the compounds is 2 to 40 mass % relative to the total mass of the liquid crystal composition of the present invention in one embodiment of the present invention. The content is 4 to 40 mass % in another embodiment of the present invention. The content is 7 to 40 mass % in still another embodiment of the present invention. The content is 10 to 40 mass % in still yet another embodiment of the present invention. The content is 12 to 40 mass % in still yet another embodiment of the present invention. The content is 15 to 40 mass % in still yet another embodiment of the present invention. The content is 17 to 40 mass % in still yet another embodiment of the present invention. The content is 18 to 40 mass % in still yet another embodiment of the present invention. The content is 20 to 40 mass % in still yet another embodiment of the present invention. The content is 22 to 40 mass % in still yet another embodiment of the present invention.

Furthermore, for example, the content of the compounds is 2 to 40 mass % relative to the total mass of the liquid crystal composition of the present invention in one embodiment of the present invention. The content is 2 to 30 mass % in another embodiment of the present invention. The content is 2 to 25 mass % in still another embodiment of the present invention. The content is 2 to 20 mass % in still yet another embodiment of the present invention. The content is 2 to 15 mass % in still yet another embodiment of the present invention. The content is 2 to 10 mass % in still yet another embodiment of the present invention. The content is 2 to 5 mass % in still yet another embodiment of the present invention. The content is 2 to 4 mass % in still yet another embodiment of the present invention.

Furthermore, the compounds represented by the general formula (V) are preferably compounds represented by general formula (V-1).

[Chem. 59]

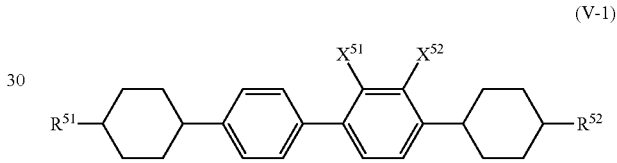

(V-1)

(In the formula, $R^{51}$ and $R^{52}$ each independently represent an alkyl group having 1 to 5 carbon atoms, an alkenyl group having 2 to 5 carbon atoms, or an alkoxy group having 1 to 4 carbon atoms; and $X^{51}$ and $X^{52}$ each independently represent a fluorine atom or a hydrogen atom.)

Furthermore, the compounds represented by the general formula (V-1) are preferably compounds represented by general formula (V-1-1).

[Chem. 60]

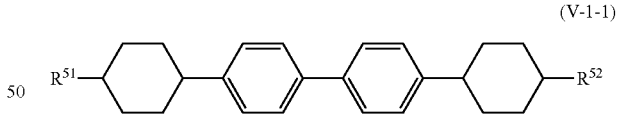

(V-1-1)

(In the formula, $R^{51}$ and $R^{52}$ each independently represent an alkyl group having 1 to 5 carbon atoms, an alkenyl group having 2 to 5 carbon atoms, or an alkoxy group having 1 to 4 carbon atoms.)

The content of the compounds represented by the general formula (V-1-1) is preferably 1 mass % or more and 15 mass % or less, more preferably 2 mass % or more and 15 mass % or less, more preferably 3 mass % or more and 10 mass % or less, and particularly preferably 4 mass % or more and 8 mass % or less relative to the total mass of the liquid crystal composition of the present invention.

Furthermore, the compounds represented by the general formula (V-1-1) are preferably compounds represented by formula (20.1) to formula (20.4) and particularly preferably a compound represented by formula (20.2).

[Chem. 61]

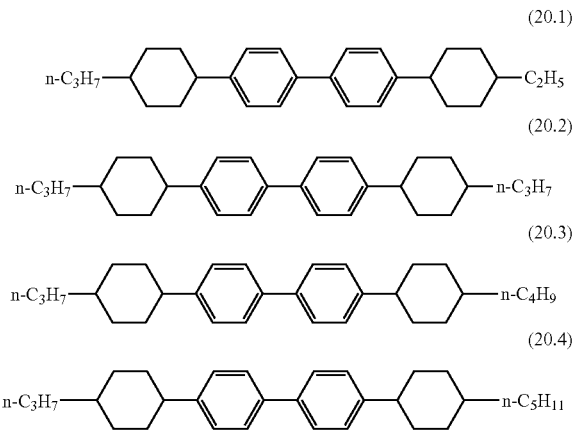

(20.1)
(20.2)
(20.3)
(20.4)

Furthermore, the compounds represented by the general formula (V-1) are preferably compounds represented by general formula (V-1-2).

[Chem. 62]

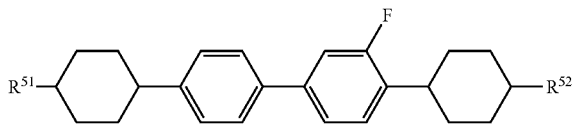

(V-1-2)

(In the formula, $R^{51}$ and $R^{52}$ each independently represent an alkyl group having 1 to 5 carbon atoms, an alkenyl group having 2 to 5 carbon atoms, or an alkoxy group having 1 to 4 carbon atoms.)

The content of the compounds represented by the general formula (V-1-2) is preferably 1 mass % or more and 15 mass % or less, more preferably 2 mass % or more and 15 mass % or less, more preferably 3 mass % or more and 10 mass % or less, and particularly preferably 4 mass % or more and 8 mass % or less relative to the total mass of the liquid crystal composition of the present invention.

Furthermore, the compounds represented by the general formula (V-1-2) are preferably compounds represented by formula (21.1) to formula (21.3) and particularly preferably a compound represented by formula (21.1).

[Chem. 63]

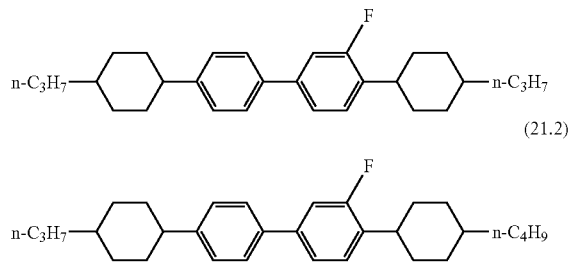

(21.1)
(21.2)
(21.3)

Furthermore, the compounds represented by the general formula (V-1) are preferably compounds represented by general formula (V-1-3).

[Chem. 64]

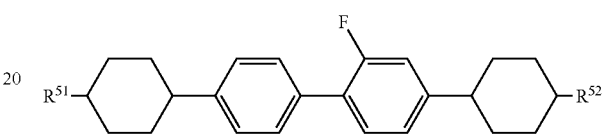

(V-1-3)

(In the formula, $R^{51}$ and $R^{52}$ each independently represent an alkyl group having 1 to 5 carbon atoms, an alkenyl group having 2 to 5 carbon atoms, or an alkoxy group having 1 to 4 carbon atoms.)

The content of the compounds represented by the general formula (V-1-3) is preferably 1 mass % or more and 15 mass % or less, more preferably 2 mass % or more and 15 mass % or less, more preferably 3 mass % or more and 10 mass % or less, and particularly preferably 4 mass % or more and 8 mass % or less relative to the total mass of the liquid crystal composition of the present invention.

Furthermore, the compounds represented by the general formula (V-1-3) are compounds represented by formula (22.1) to formula (22.3) and preferably a compound represented by formula (22.1).

[Chem. 65]

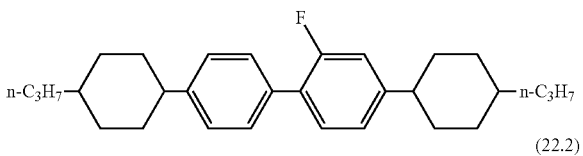
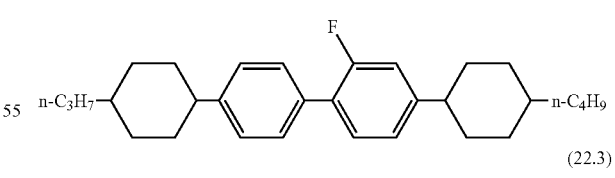

(22.1)
(22.2)
(22.3)

Furthermore, the compounds represented by the general formula (V) are preferably compounds represented by general formula (V-2).

[Chem. 66]

(V-2)

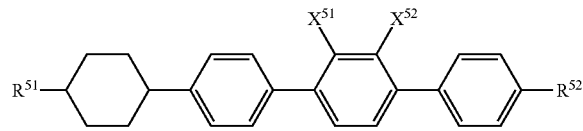

(In the formula, $R^{51}$ and $R^{52}$ each independently represent an alkyl group having 1 to 5 carbon atoms, an alkenyl group having 2 to 5 carbon atoms, or an alkoxy group having 1 to 4 carbon atoms; and $X^{51}$ and $X^{52}$ each independently represent a fluorine atom or a hydrogen atom.)

Although the number of compounds that can be combined with each other is not particularly limited, a plurality of the compounds represented by the general formula (V-2) can be used in combination in accordance with the required characteristics such as solubility at low temperature, transition temperature, electrical reliability, and double refractive index. For example, the number of the compounds used is one in one embodiment of the present invention. The number of the compounds is two or more in another embodiment of the present invention.

For example, the content of the compounds is 2 to 40 mass % relative to the total mass of the liquid crystal composition of the present invention in one embodiment of the present invention. The content is 4 to 40 mass % in another embodiment of the present invention. The content is 7 to 40 mass % in still another embodiment of the present invention. The content is 10 to 40 mass % in still yet another embodiment of the present invention. The content is 12 to 40 mass % in still yet another embodiment of the present invention. The content is 15 to 40 mass % in still yet another embodiment of the present invention. The content is 17 to 40 mass % in still yet another embodiment of the present invention. The content is 18 to 40 mass % in still yet another embodiment of the present invention. The content is 20 to 40 mass % in still yet another embodiment of the present invention. The content is 22 to 40 mass % in still yet another embodiment of the present invention.

Furthermore, for example, the content of the compounds is 2 to 40 mass % relative to the total mass of the liquid crystal composition of the present invention in one embodiment of the present invention. The content is 2 to 30 mass % in another embodiment of the present invention. The content is 2 to 25 mass % in still another embodiment of the present invention. The content is 2 to 20 mass % in still yet another embodiment of the present invention. The content is 2 to 15 mass % in still yet another embodiment of the present invention. The content is 2 to 10 mass % in still yet another embodiment of the present invention. The content is 2 to 5 mass % in still yet another embodiment of the present invention. The content is 2 to 4 mass % in still yet another embodiment of the present invention.

When an embodiment in which the liquid crystal composition of the present invention has high Tni is desired, the content of the compounds represented by the general formula (V-2) is preferably increased. When an embodiment in which the liquid crystal composition has low viscosity is desired, the content is preferably decreased.

Furthermore, the compounds represented by the general formula (V-2) are preferably compounds represented by general formula (V-2-1).

[Chem. 67]

(V-2-1)

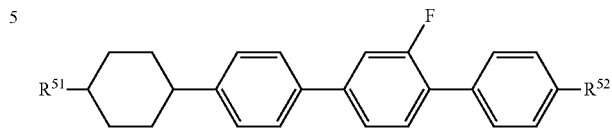

(In the formula, $R^{51}$ and $R^{52}$ each independently represent an alkyl group having 1 to 5 carbon atoms, an alkenyl group having 2 to 5 carbon atoms, or an alkoxy group having 1 to 4 carbon atoms.)

Furthermore, the compounds represented by the general formula (V-2-1) are preferably compounds represented by formula (23.1) to formula (23.4) and particularly preferably a compound represented by formula (23.1) or formula (23.2).

[Chem. 68]

(23.1)

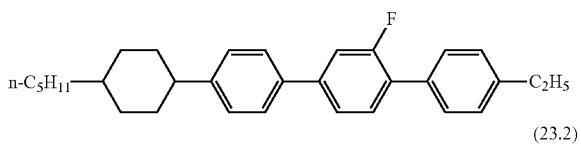

(23.2)

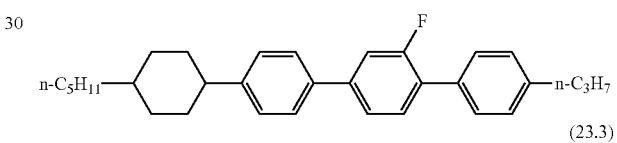

(23.3)

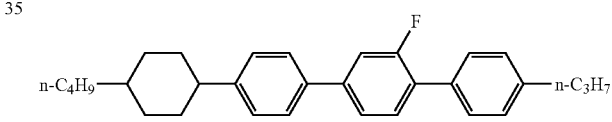

(23.4)

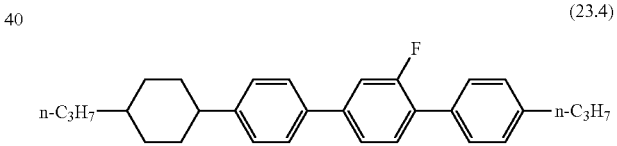

In the liquid crystal composition of the present invention, the content of the compound represented by the formula (23.1) is preferably 1 mass % or more and 25 mass % or less relative to the total mass of the liquid crystal composition of the present invention in consideration of solubility at low temperature, transition temperature, electrical reliability, and the like.

In the liquid crystal composition of the present invention, the content of the compound represented by the formula (23.2) is preferably 1 mass % or more and 25 mass % or less relative to the total mass of the liquid crystal composition of the present invention in consideration of solubility at low temperature, transition temperature, electrical reliability, and the like.

In the liquid crystal composition of the present invention, the total content of the compound represented by the formula (23.1) and the compound represented by the formula (23.2) is preferably 1 mass % or more and 25 mass % or less relative to the total mass of the liquid crystal composition of the present invention in consideration of solubility at low temperature, transition temperature, electrical reliability, and the like.

Furthermore, the compounds represented by the general formula (V-2) are preferably compounds represented by general formula (V-2-2).

[Chem. 69]

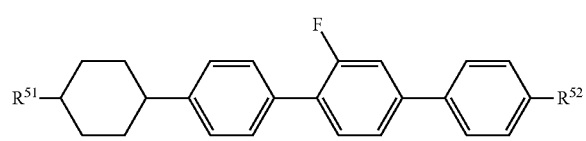

(V-2-2)

(In the formula, $R^{51}$ and $R^{52}$ each independently represent an alkyl group having 1 to 5 carbon atoms, an alkenyl group having 2 to 5 carbon atoms, or an alkoxy group having 1 to 4 carbon atoms.)

Furthermore, the compounds represented by the general formula (V-2-2) are preferably compounds represented by formula (24.1) to formula (24.4) and more preferably a compound represented by formula (24.1) or formula (24.2).

[Chem. 70]

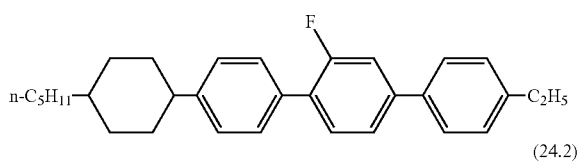

(24.1)

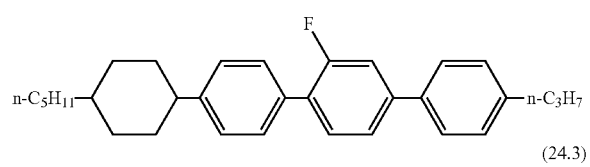

(24.2)

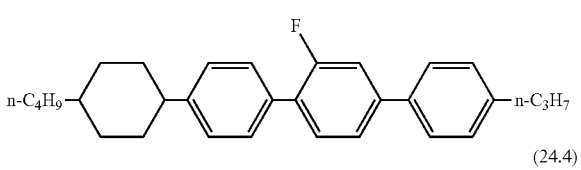

(24.3)

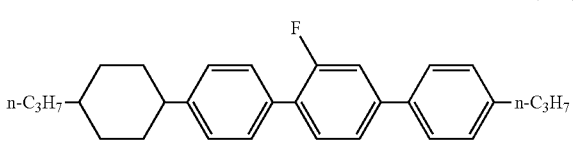

(24.4)

Furthermore, the compounds represented by the general formula (V) are preferably compounds represented by general formula (V-3).

[Chem. 71]

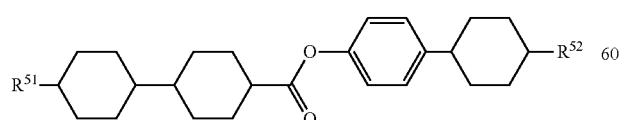

(V-3)

(In the formula, $R^{51}$ and $R^{52}$ each independently represent an alkyl group having 1 to 5 carbon atoms, an alkenyl group having 2 to 5 carbon atoms, or an alkoxy group having 1 to 4 carbon atoms.)

Although the number of compounds that can be combined with each other is not particularly limited, a plurality of the compounds represented by the general formula (V-3) can be used in combination in accordance with the required characteristics such as solubility at low temperature, transition temperature, electrical reliability, and double refractive index. For example, the number of the compounds used is one in one embodiment of the present invention. The number of the compounds is two in another embodiment of the present invention. The number of the compounds is three or more in still another embodiment of the present invention.

The content of the compounds represented by the general formula (V-3) is preferably 2 mass % or more and 16 mass % or less, more preferably 4 mass % or more and 16 mass % or less, more preferably 7 mass % or more and 13 mass % or less, and particularly preferably 8 mass % or more and 11 mass % or less relative to the total mass of the liquid crystal composition of the present invention.

Furthermore, the compounds represented by the general formula (V-3) are preferably compounds represented by formula (25.1) to formula (25.3).

[Chem. 72]

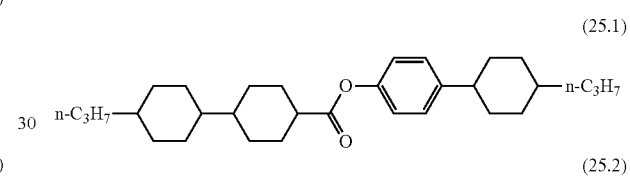

(25.1)

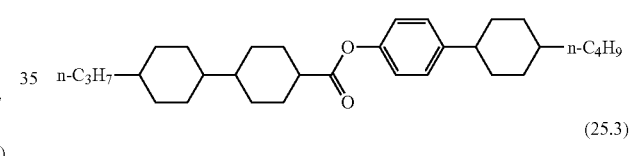

(25.2)

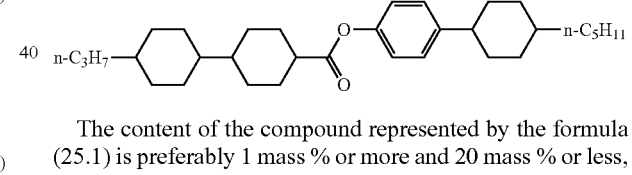

(25.3)

The content of the compound represented by the formula (25.1) is preferably 1 mass % or more and 20 mass % or less, more preferably 1 mass % or more and 15 mass % or less, more preferably 1 mass % or more and 10 mass % or less, more preferably 1 mass % or more and 8 mass % or less, and particularly preferably 3 mass % or more and 5 mass % or less relative to the total mass of the liquid crystal composition of the present invention.

In the particularly preferable range, the content may be 3 mass % or more and 4 mass % or less or 4 mass % or more and 5 mass % or less.

The liquid crystal composition of the present invention may further contain one or more of compounds represented by general formula (VI).

[Chem. 73]

(VI)

(In the formula, $R^{61}$ and $R^{62}$ each independently represent a linear alkyl group having 1 to 10 carbon atoms, a linear alkoxy group having 1 to 10 carbon atoms, or a linear alkenyl group having 2 to 10 carbon atoms.)

Although the number of compounds that can be combined with each other is not particularly limited, one to three of the plurality of compounds represented by the general formula (VI) are preferably contained, one to four of the compounds are more preferably contained, and one to five or more of the compounds are particularly preferably contained in accordance with the required characteristics such as solubility at low temperature, transition temperature, electrical reliability, and double refractive index. The maximum content is preferably 35 mass % or less, more preferably 25 mass % or less, and more preferably 15 mass % or less.

Specifically, the following compounds can be suitably used as the compounds represented by the general formula (VI).

[Chem. 74]

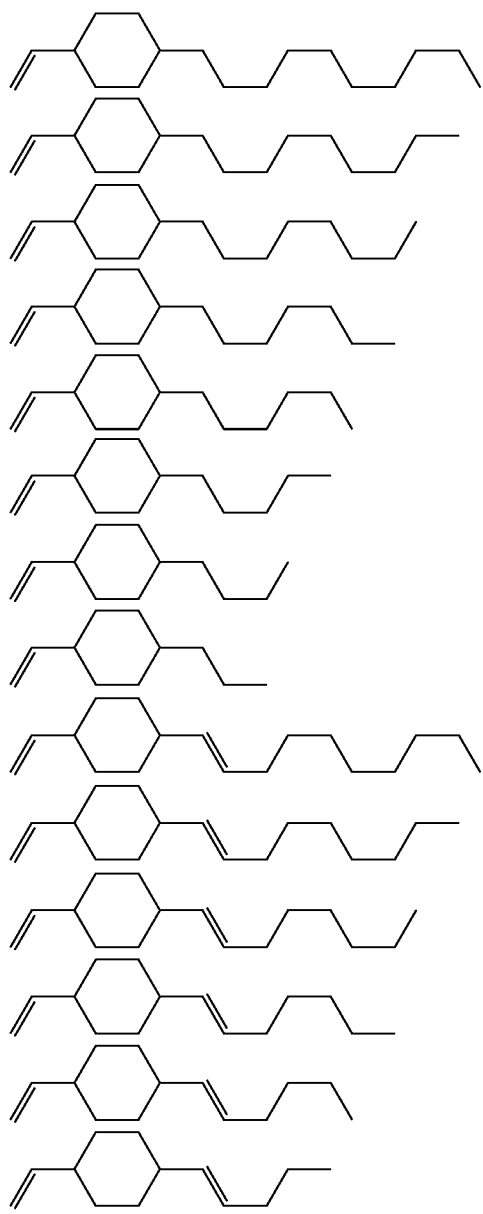

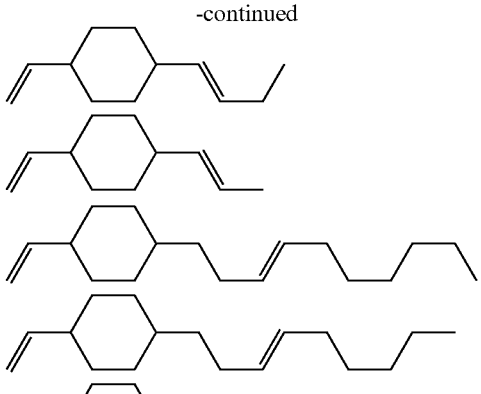

[Chem. 75]

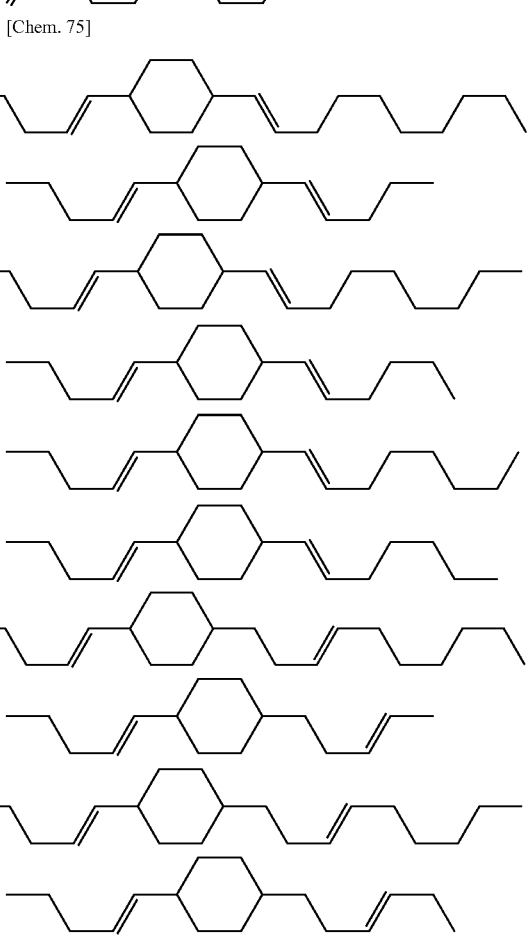

-continued
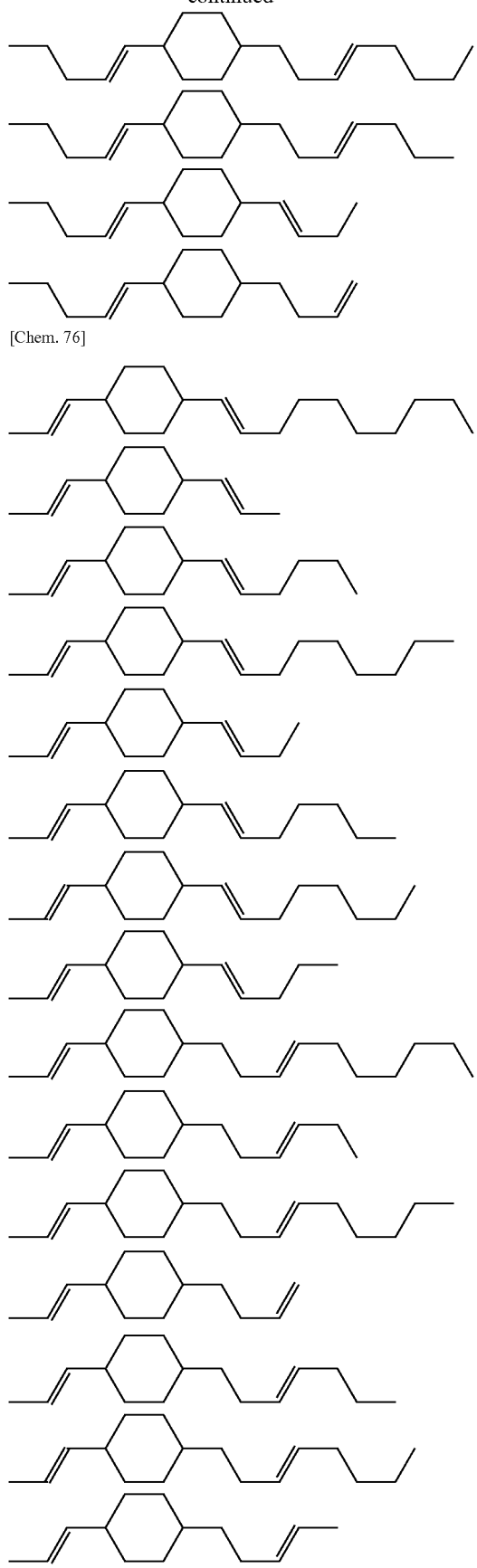
[Chem. 76]
-continued
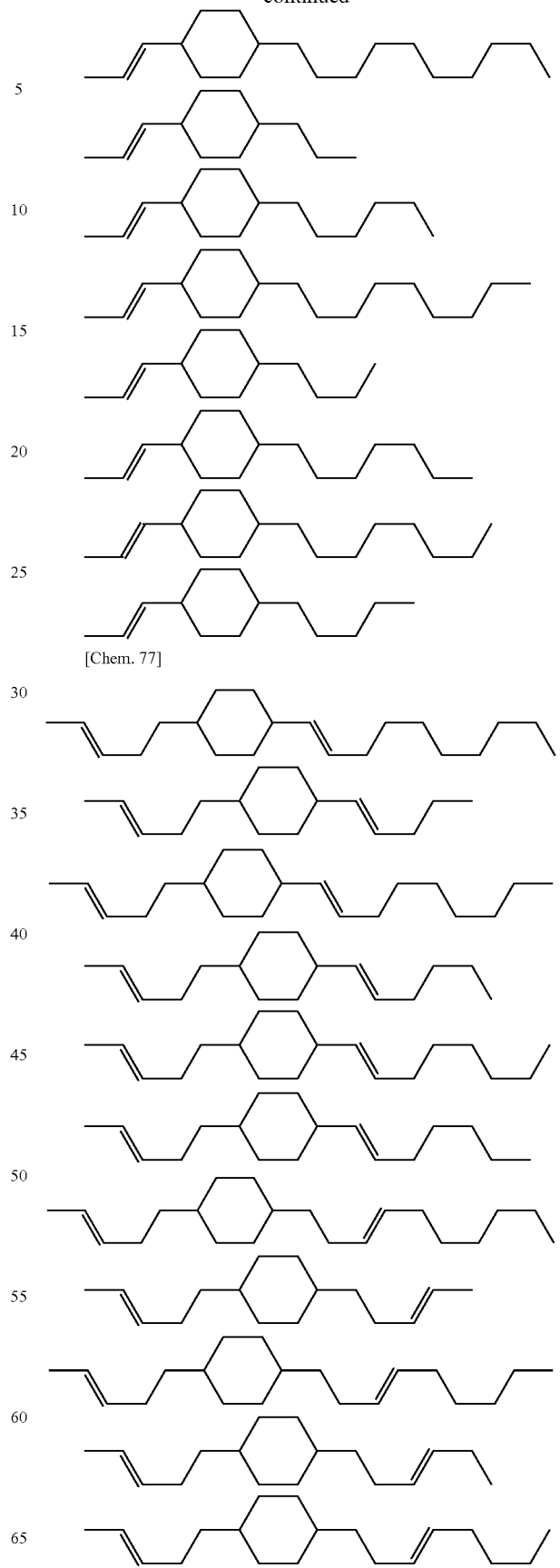
[Chem. 77]

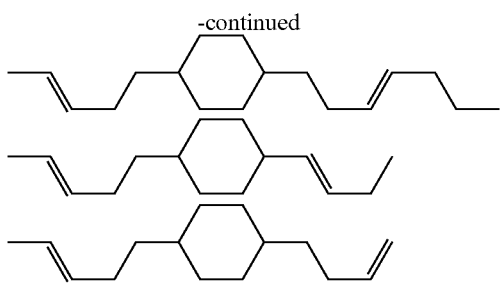

The liquid crystal composition of the present invention may further contain one or more of compounds represented by general formula (VII).

[Chem. 78]

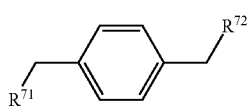

(VII)

(In the formula, $R^{71}$ and $R^{72}$ each independently represent a linear alkyl group having 1 to 10 carbon atoms, a linear alkoxy group having 1 to 10 carbon atoms, or a linear alkenyl group having 4 to 10 carbon atoms.)

Although the number of compounds that can be combined with each other is not particularly limited, one to three of the plurality of compounds represented by the general formula (VII) are preferably contained, one to four of the compounds are more preferably contained, and one to five or more of the compounds are particularly preferably contained in accordance with the required characteristics such as solubility at low temperature, transition temperature, electrical reliability, and double refractive index. The maximum content is preferably 35 mass % or less, more preferably 25 mass % or less, and more preferably 15 mass % or less.

Specifically, the following compounds can be suitably used as the compounds represented by the general formula (VII).

[Chem. 79]

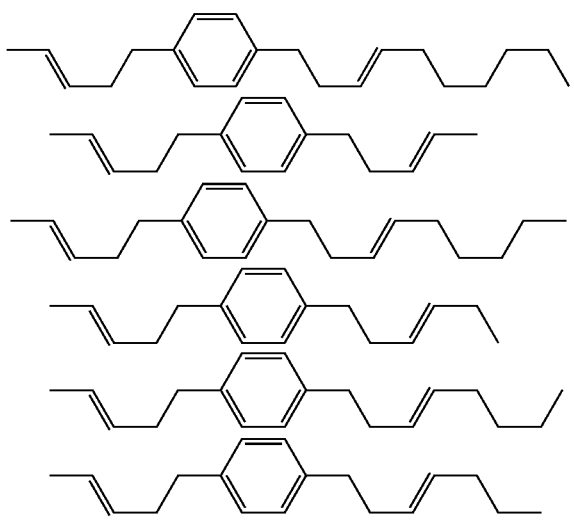

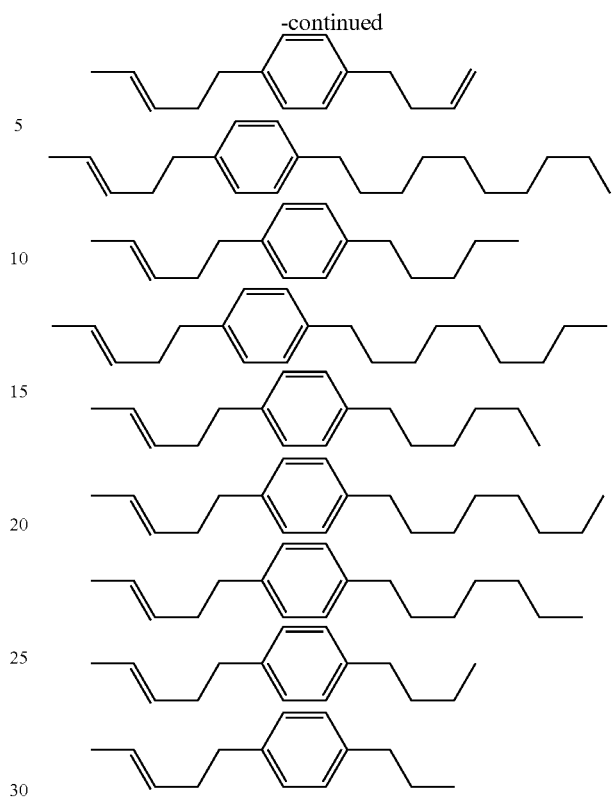

The liquid crystal composition of the present invention preferably contains one or more of compounds represented by general formula (M) below.

[Chem. 80]

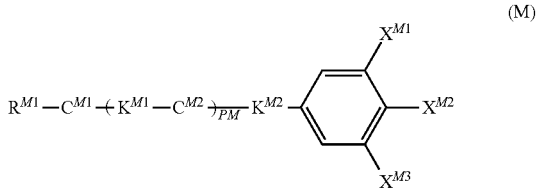

(M)

(In the formula, $R^{M1}$ represents an alkyl group having 1 to 8 carbon atoms where one —$CH_2$— or two or more non-adjacent —$CH_2$— in the alkyl group may each independently be substituted with —CH=CH—, —C≡C—, —O—, —CO—, —COO—, or —OCO—;

PM represents 0, 1, 2, 3, or 4;

$C^{M1}$ and $C^{M2}$ each independently represent a group selected from the group consisting of:

(d) a 1,4-cyclohexylene group (one —$CH_2$— or two or more non-adjacent —$CH_2$— present in the group may be substituted with —O— or —S—) and (e) a 1,4-phenylene group (one —CH= or two or more non-adjacent —CH= present in the group may be substituted with —N=), where the group (d) and the group (e) may each independently be substituted with a cyano group, a fluorine atom, or a chlorine atom;

$K^{M1}$ and $K^{M2}$ each independently represent a single bond, —$CH_2CH_2$—, —$(CH_2)_4$—, —$OCH_2$—, —$CH_2O$—, —$OCF_2$—, —$CF_2O$—, —COO—, —OCO—, or —C≡C—;

when PM represents 2, 3, or 4 and thus a plurality of $K^{M1}$ are present, the plurality of $K^{M1}$ may be the same or different and when PM represents 2, 3, or 4 and thus a plurality of $C^{M2}$ are present, the plurality of $C^{M2}$ may be the same or different;

$X^{M1}$ and $X^{M3}$ each independently represent a hydrogen atom, a chlorine atom, or a fluorine atom; and $X^{M2}$ represents a hydrogen atom, a fluorine atom, a chlorine atom, a cyano group, a trifluoromethyl group, a fluoromethoxy group, a difluoromethoxy group, a trifluoromethoxy group, or a 2,2,2-trifluoroethyl group, the compounds represented by the general formula (M) excluding the compounds represented by the general formula (i) and the compounds represented by the general formula (ii).)

Although the number of compounds that can be combined with each other is not particularly limited, a plurality of the compounds represented by the general formula (M) can be used in combination in accordance with desired characteristics such as solubility at low temperature, transition temperature, electrical reliability, and double refractive index. For example, the number of the compounds used is one in one embodiment of the present invention. The number of the compounds is two in another embodiment of the present invention. The number of the compounds is three in still another embodiment of the present invention. The number of the compounds is four in still yet another embodiment of the present invention. The number of the compounds is five in still yet another embodiment of the present invention. The number of the compounds is six in still yet another embodiment of the present invention. The number of the compounds is seven or more in still yet another embodiment of the present invention.

In the liquid crystal composition of the present invention, the content of the compounds represented by the general formula (M) needs to be appropriately adjusted in accordance with the required characteristics such as solubility at low temperature, transition temperature, electrical reliability, double refractive index, process compatibility, drop marks, image sticking, and dielectric anisotropy.

For example, the content of the compounds is 1 to 95 mass % relative to the total mass of the liquid crystal composition of the present invention in one embodiment of the present invention. For example, the content of the compounds is 10 to 95 mass % in another embodiment of the present invention. For example, the content of the compounds is 20 to 95 mass % in still another embodiment of the present invention. For example, the content of the compounds is 30 to 95 mass % in still yet another embodiment of the present invention. For example, the content of the compounds is 40 to 95 mass % in still yet another embodiment of the present invention. For example, the content of the compounds is 45 to 95 mass % in still yet another embodiment of the present invention. For example, the content of the compounds is 50 to 95 mass % in still yet another embodiment of the present invention. For example, the content of the compounds is 55 to 95 mass % in still yet another embodiment of the present invention. For example, the content of the compounds is 60 to 95 mass % in still yet another embodiment of the present invention. For example, the content of the compounds is 65 to 95 mass % in still yet another embodiment of the present invention. For example, the content of the compounds is 70 to 95 mass % in still yet another embodiment of the present invention. For example, the content of the compounds is 75 to 95 mass % in still yet another embodiment of the present invention. For example, the content of the compounds is 80 to 95 mass % in still yet another embodiment of the present invention.

Furthermore, for example, the content of the compounds is 1 to 95 mass % relative to the total mass of the liquid crystal composition of the present invention in one embodiment of the present invention. The content of the compounds is 1 to 85 mass % in another embodiment of the present invention. The content of the compounds is 1 to 75 mass % in still another embodiment of the present invention. The content of the compounds is 1 to 65 mass % in still yet another embodiment of the present invention. The content of the compounds is 1 to 55 mass % in still yet another embodiment of the present invention. The content of the compounds is 1 to 45 mass % in still yet another embodiment of the present invention. The content of the compounds is 1 to 35 mass % in still yet another embodiment of the present invention. The content of the compounds is 1 to 25 mass % in still yet another embodiment of the present invention.

When the liquid crystal composition of the present invention needs to have low viscosity to achieve high response speed, the lower limit and the upper limit are preferably set to be low. When the liquid crystal composition of the present invention needs to have high Tni to achieve good temperature stability, the lower limit and the upper limit are preferably set to be low. When the dielectric anisotropy is increased to maintain low drive voltage, the lower limit and the upper limit are preferably set to be high.

In the case where a ring structure to which $R^{M1}$ is bonded is a phenyl group (aromatic group), $R^{M1}$ preferably represents a linear alkyl group having 1 to 5 carbon atoms, a linear alkoxy group having 1 to 4 carbon atoms, or an alkenyl group having 4 or 5 carbon atoms. In the case where a ring structure to which $R^{M1}$ is bonded is a saturated ring structure such as cyclohexane, pyran, or dioxane, $R^{M1}$ preferably represents a linear alkyl group having 1 to 5 carbon atoms, a linear alkoxy group having 1 to 4 carbon atoms, or a linear alkenyl group having 2 to 5 carbon atoms.

In the case where the chemical stability of the liquid crystal composition is required, the compounds represented by the general formula (M) preferably do not include chlorine atoms in their molecules. Furthermore, the content of a compound having a chlorine atom in the liquid crystal composition is preferably 5% or less, more preferably 3% or less, more preferably 1% or less, and more preferably 0.5% or less. More preferably, the liquid crystal composition substantially does not contain the compound having a chlorine atom. The phrase "substantially does not contain" means that only a compound unintentionally having a chlorine atom, such as a compound produced as an impurity during the compound production, is mixed in the liquid crystal composition.

The compounds represented by the general formula (M) are, for example, preferably compounds selected from the group of compounds represented by general formula (VIII).

[Chem. 81]

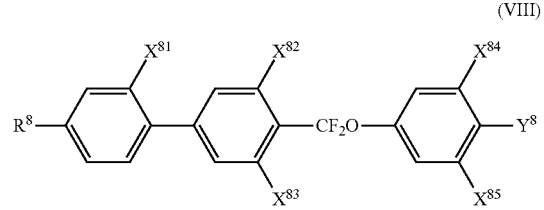

(VIII)

(In the formula, $R^8$ represents an alkyl group having 1 to 5 carbon atoms, an alkenyl group having 2 to 5 carbon atoms, or an alkoxy group having 1 to 4 carbon atoms; $X^{81}$ to $X^{85}$ each independently represent a hydrogen atom or a fluorine atom; and $Y^8$ represents a fluorine atom or —$OCF_3$.)

Although the number of compounds that can be combined with each other is not particularly limited, a plurality of the compounds represented by the general formula (VIII) can be used in combination in accordance with desired characteristics such as solubility at low temperature, transition temperature, electrical reliability, and double refractive index. For example, the number of the compounds used is one in one embodiment of the present invention. The number of the compounds is two in another embodiment of the present invention. The number of the compounds is three or more in still another embodiment of the present invention.

In the liquid crystal composition of the present invention, the content of the compounds represented by the general formula (VIII) needs to be appropriately adjusted in accordance with the required characteristics such as solubility at low temperature, transition temperature, electrical reliability, double refractive index, process compatibility, drop marks, image sticking, and dielectric anisotropy.

For example, the content of the compounds is 2 to 40 mass % relative to the total mass of the liquid crystal composition of the present invention in one embodiment of the present invention. For example, the content of the compounds is 4 to 40 mass % in another embodiment of the present invention. For example, the content of the compounds is 5 to 40 mass % in still another embodiment of the present invention. For example, the content of the compounds is 6 to 40 mass % in still yet another embodiment of the present invention. For example, the content of the compounds is 7 to 40 mass % in still yet another embodiment of the present invention. For example, the content of the compounds is 8 to 40 mass % in still yet another embodiment of the present invention. For example, the content of the compounds is 9 to 40 mass % in still yet another embodiment of the present invention. For example, the content of the compounds is 10 to 40 mass % in still yet another embodiment of the present invention. For example, the content of the compounds is 11 to 40 mass % in still yet another embodiment of the present invention. For example, the content of the compounds is 12 to 40 mass % in still yet another embodiment of the present invention. For example, the content of the compounds is 14 to 40 mass % in still yet another embodiment of the present invention. For example, the content of the compounds is 15 to 40 mass % in still yet another embodiment of the present invention. For example, the content of the compounds is 21 to 40 mass % in still yet another embodiment of the present invention. For example, the content of the compounds is 23 to 40 mass % in still yet another embodiment of the present invention.

Furthermore, for example, the content of the compounds is 2 to 40 mass % relative to the total mass of the liquid crystal composition of the present invention in one embodiment of the present invention. The content of the compounds is 2 to 30 mass % in another embodiment of the present invention. The content of the compounds is 2 to 25 mass % in still another embodiment of the present invention. The content of the compounds is 2 to 21 mass % in still yet another embodiment of the present invention. The content of the compounds is 2 to 16 mass % in still yet another embodiment of the present invention. The content of the compounds is 2 to 12 mass % in still yet another embodiment of the present invention. The content of the compounds is 2 to 8 mass % in still yet another embodiment of the present invention. The content of the compounds is 2 to 5 mass % in still yet another embodiment of the present invention.

When the liquid crystal composition of the present invention needs to have low viscosity to achieve high response speed, the lower limit and the upper limit are preferably set to be low. When the liquid crystal composition of the present invention needs to have high Tni to achieve good temperature stability, the lower limit and the upper limit are preferably set to be low. When the dielectric anisotropy is increased to maintain low drive voltage, the lower limit and the upper limit are preferably set to be high.

Furthermore, the compounds represented by the general formula (VIII) are preferably compounds represented by general formula (VIII-1).

[Chem. 82]

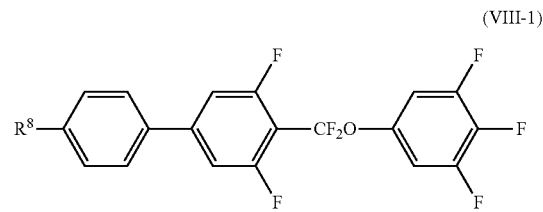

(VIII-1)

(In the formula, $R^8$ represents an alkyl group having 1 to 5 carbon atoms, an alkenyl group having 2 to 5 carbon atoms, or an alkoxy group having 1 to 4 carbon atoms.)

Although the number of compounds that can be combined with each other is not particularly limited, a plurality of the compounds represented by the general formula (VIII-1) can be used in combination in accordance with desired characteristics such as solubility at low temperature, transition temperature, electrical reliability, and double refractive index. For example, the number of the compounds used is one in one embodiment of the present invention. The number of the compounds is two or more in another embodiment of the present invention.

More specifically, the compounds represented by the general formula (VIII-1) are preferably compounds represented by formula (26.1) to formula (26.4), more preferably a compound represented by formula (26.1) or formula (26.2), and more preferably a compound represented by formula (26.2).

[Chem. 83]

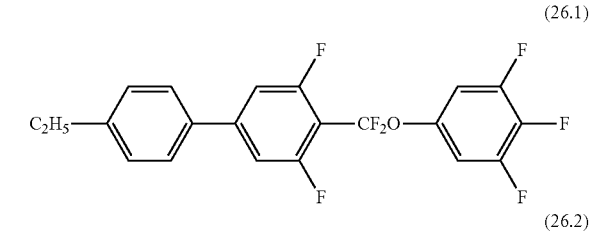

(26.1)

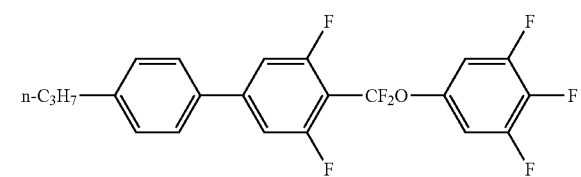

(26.2)

-continued

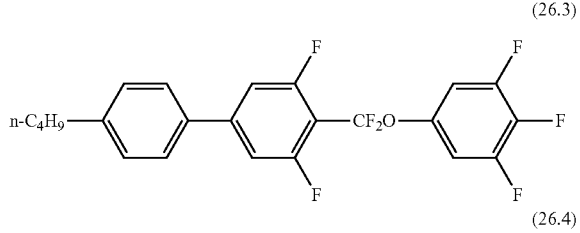
(26.3)

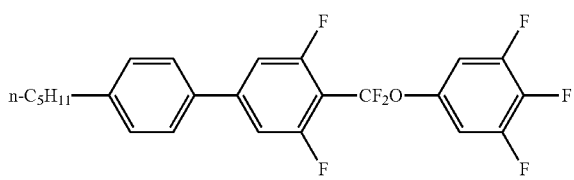
(26.4)

The content of the compound represented by the formula (26.1) is preferably 1 mass % or more and 40 mass % or less, more preferably 1 mass % or more and 30 mass % or less, and more preferably 1 mass % or more and 20 mass % or less relative to the total mass of the liquid crystal composition of the present invention in consideration of solubility at low temperature, transition temperature, electrical reliability, double refractive index, and the like.

The content of the compound represented by the formula (26.2) is preferably 2 mass % or more and 40 mass % or less, more preferably 3 mass % or more and 30 mass % or less, more preferably 4 mass % or more and 20 mass % or less, and particularly preferably 5 mass % or more and 15 mass % or less relative to the total mass of the liquid crystal composition of the present invention in consideration of solubility at low temperature, transition temperature, electrical reliability, double refractive index, and the like.

Examples of the content in the particularly preferable range include 5 mass % or more and 12 mass % or less, 5 mass % or more and 10 mass % or less, 5 mass % or more and 8 mass % or less, 5 mass % or more and 7 mass % or less, 5 mass % or more and 6 mass % or less, 6 mass % or more and 15 mass % or less, 7 mass % or more and 15 mass % or less, 8 mass % or more and 15 mass % or less, 10 mass % or more and 15 mass % or less, and 12 mass % or more and 15 mass % or less.

The total content of the compound represented by the formula (26.1) and the compound represented by the formula (26.2) is preferably 5 to 40 mass % relative to the total mass of the liquid crystal composition of the present invention.

Furthermore, the compounds represented by the general formula (VIII) are preferably compounds represented by general formula (VIII-2).

[Chem. 84]

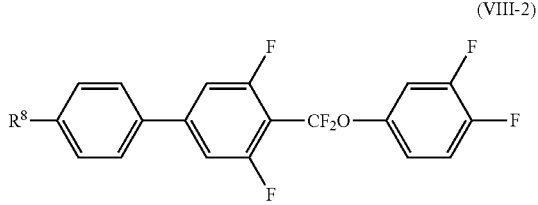
(VIII-2)

(In the formula, $R^8$ represents an alkyl group having 1 to 5 carbon atoms, an alkenyl group having 2 to 5 carbon atoms, or an alkoxy group having 1 to 4 carbon atoms.)

Although the number of compounds that can be combined with each other is not particularly limited, a plurality of the compounds represented by the general formula (VIII-2) can be used in combination in accordance with desired characteristics such as solubility at low temperature, transition temperature, electrical reliability, and double refractive index. For example, the number of the compounds used is one in one embodiment of the present invention. The number of the compounds is two in another embodiment of the present invention. The number of the compounds is three or more in still another embodiment of the present invention.

The content of the compounds represented by the general formula (VIII-2) is preferably 2.5 mass % or more and 25 mass % or less, more preferably 8 mass % or more and 25 mass % or less, more preferably 10 mass % and 20 mass % or less, and more preferably 12 mass % or more and 15 mass % or less in consideration of solubility at low temperature, transition temperature, electrical reliability, double refractive index, and the like.

Furthermore, the compounds represented by the general formula (VIII-2) are preferably compounds represented by formula (27.1) to formula (27.4) and more preferably a compound represented by formula (27.2).

[Chem. 85]

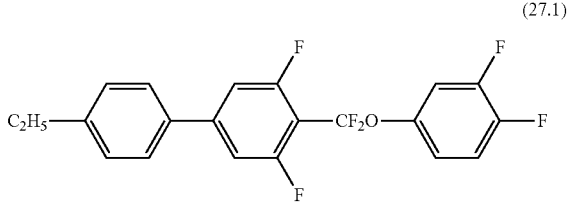
(27.1)

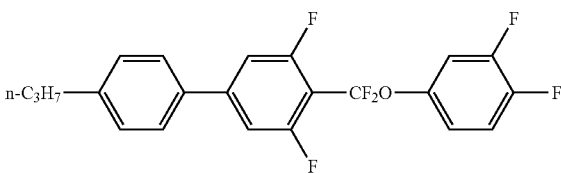
(27.2)

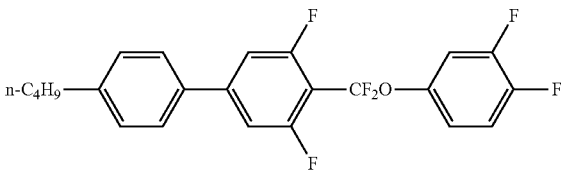
(27.3)

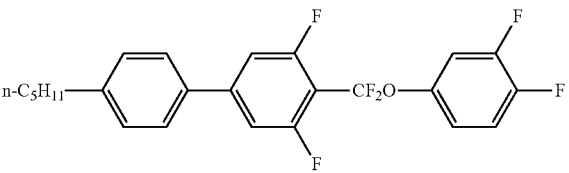
(27.4)

Furthermore, the compounds represented by the general formula (VIII) are preferably compounds represented by general formula (VIII-3).

[Chem. 86]

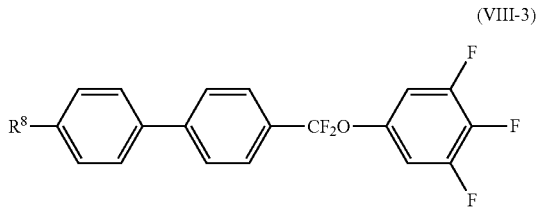

(VIII-3)

(In the formula, $R^8$ represents an alkyl group having 1 to 5 carbon atoms, an alkenyl group having 2 to 5 carbon atoms, or an alkoxy group having 1 to 4 carbon atoms.)

Although the number of compounds that can be combined with each other is not particularly limited, a plurality of the compounds represented by the general formula (VIII-3) can be used in combination in accordance with desired characteristics such as solubility at low temperature, transition temperature, electrical reliability, and double refractive index. For example, the number of the compounds used is one in one embodiment of the present invention. The number of the compounds is two or more in another embodiment of the present invention.

More specifically, the compounds represented by the general formula (VIII-3) are preferably compounds represented by formula (26.11) to formula (26.14), more preferably a compound represented by formula (26.11) or formula (26.12), and more preferably a compound represented by formula (26.12).

[Chem. 87]

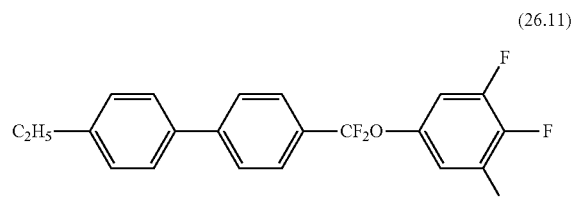

(26.11)

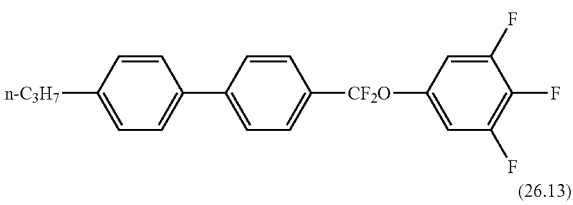

(26.12)

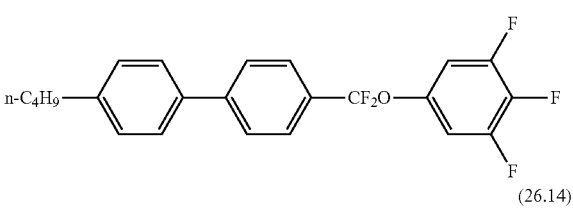

(26.13)

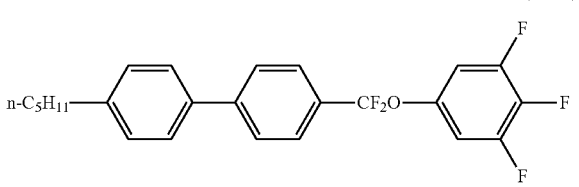

(26.14)

Furthermore, the compounds represented by the general formula (M) are, for example, preferably compounds selected from the group of compounds represented by general formula (IX). Note that the compounds represented by the general formula (M) exclude the compounds represented by the general formula (i).

[Chem. 88]

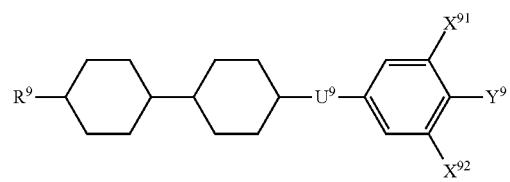

(IX)

(In the formula, $R^9$ represents an alkyl group having 1 to 5 carbon atoms, an alkenyl group having 2 to 5 carbon atoms, or an alkoxy group having 1 to 4 carbon atoms; $X^{91}$ and $X^{92}$ each independently represent a hydrogen atom or a fluorine atom; $Y^9$ represents a fluorine atom, a chlorine atom, or —$OCF_3$; and $U^9$ represents a single bond, —COO—, or —$CF_2O$—.)

Although the number of compounds that can be combined with each other is not particularly limited, a plurality of the compounds represented by the general formula (Ix) can be used in combination in accordance with the desired characteristics such as solubility at low temperature, transition temperature, electrical reliability, and double refractive index. For example, the number of the compounds used is one in one embodiment of the present invention. The number of the compounds is two in another embodiment of the present invention. The number of the compounds is three in still another embodiment of the present invention. The number of the compounds is four in still yet another embodiment of the present invention. The number of the compounds is five in still yet another embodiment of the present invention. The number of the compounds is six or more in still yet another embodiment of the present invention.

In the liquid crystal composition of the present invention, the content of the compounds represented by the general formula (IX) needs to be appropriately adjusted in accordance with the required characteristics such as solubility at low temperature, transition temperature, electrical reliability, double refractive index, process compatibility, drop marks, image sticking, and dielectric anisotropy.

For example, the content of the compounds is 3 to 70 mass % relative to the total mass of the liquid crystal composition of the present invention in one embodiment of the present invention. For example, the content of the compounds is 5 to 70 mass % in another embodiment of the present invention. For example, the content of the compounds is 8 to 70 mass % in still another embodiment of the present invention. For example, the content of the compounds is 10 to 70 mass % in still yet another embodiment of the present invention. For example, the content of the compounds is 12 to 70 mass % in still yet another embodiment of the present invention. For example, the content of the compounds is 15 to 70 mass % in still yet another embodiment of the present invention. For example, the content of the compounds is 17 to 70 mass % in still yet another embodiment of the present invention. For example, the content of the compounds is 20 to 70 mass % in still yet another embodiment of the present invention. For example, the content of the compounds is 24 to 70 mass % in still yet another embodiment of the present invention. For example, the content of the compounds is 28 to 70 mass % in still yet another embodiment of the present invention.

For example, the content of the compounds is 30 to 70 mass % in still yet another embodiment of the present invention. For example, the content of the compounds is 34 to 70 mass % in still yet another embodiment of the present invention. For example, the content of the compounds is 39 to 70 mass % in still yet another embodiment of the present invention. For example, the content of the compounds is 40 to 70 mass % in still yet another embodiment of the present invention. For example, the content of the compounds is 42 to 70 mass % in still yet another embodiment of the present invention. For example, the content of the compounds is 45 to 70 mass % in still yet another embodiment of the present invention.

Furthermore, for example, the content of the compounds is 3 to 70 mass % relative to the total mass of the liquid crystal composition of the present invention in one embodiment of the present invention. The content of the compounds is 3 to 60 mass % in another embodiment of the present invention. The content of the compounds is 3 to 55 mass % in still another embodiment of the present invention. The content of the compounds is 3 to 50 mass % in still yet another embodiment of the present invention. The content of the compounds is 3 to 45 mass % in still yet another embodiment of the present invention. The content of the compounds is 3 to 40 mass % in still yet another embodiment of the present invention. The content of the compounds is 3 to 35 mass % in still yet another embodiment of the present invention. The content of the compounds is 3 to 30 mass % in still yet another embodiment of the present invention. The content of the compounds is 25 mass % in still yet another embodiment of the present invention. The content of the compounds is 3 to 20 mass % in still yet another embodiment of the present invention. The content of the compounds is 3 to 15 mass % in still yet another embodiment of the present invention. The content of the compounds is 3 to 10 mass % in still yet another embodiment of the present invention.

When the liquid crystal composition of the present invention needs to have low viscosity to achieve high response speed, the lower limit and the upper limit are preferably set to be low. When the liquid crystal composition of the present invention needs to have high Tni to suppress the generation of image sticking, the lower limit and the upper limit are preferably set to be low. When the dielectric anisotropy is increased to maintain low drive voltage, the lower limit and the upper limit are preferably set to be high.

Furthermore, the compounds represented by the general formula (IX) are preferably compounds represented by general formula (IX-1).

[Chem. 89]

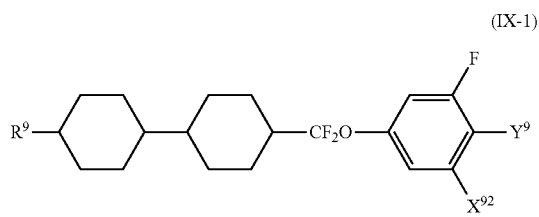

(IX-1)

(In the formula, $R^9$ represents an alkyl group having 1 to 5 carbon atoms, an alkenyl group having 2 to 5 carbon atoms, or an alkoxy group having 1 to 4 carbon atoms; $X^{92}$ represents a hydrogen atom or a fluorine atom; and $Y^9$ represents a fluorine atom or —$OCF_3$.)

Although the number of compounds that can be combined with each other is not particularly limited, a plurality of the compounds represented by the general formula (IX-1) can be used in combination in accordance with the desired characteristics such as solubility at low temperature, transition temperature, electrical reliability, and double refractive index. For example, the number of the compounds used is one in one embodiment of the present invention. The number of the compounds is two in another embodiment of the present invention. The number of the compounds is three in still another embodiment of the present invention. The number of the compounds is four or more in still yet another embodiment of the present invention.

Furthermore, the compounds represented by the general formula (IX-1) are preferably compounds represented by general formula (IX-1-1).

[Chem. 90]

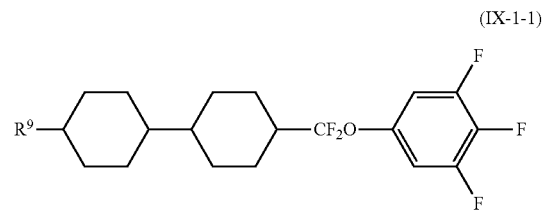

(IX-1-1)

(In the formula, $R^9$ represents an alkyl group having 1 to 5 carbon atoms, an alkenyl group having 2 to 5 carbon atoms, or an alkoxy group having 1 to 4 carbon atoms.)

Although the number of compounds that can be combined with each other is not particularly limited, a plurality of the compounds represented by the general formula (IX-1-1) can be used in combination in accordance with the desired characteristics such as solubility at low temperature, transition temperature, electrical reliability, and double refractive index. For example, the number of the compounds used is one in one embodiment of the present invention. The number of the compounds is two in another embodiment of the present invention.

The content of the compounds represented by the general formula (IX-1-1) relative to the total mass of the liquid crystal composition of the present invention has a preferred upper limit and a preferred lower limit for each embodiment in consideration of solubility at low temperature, transition temperature, electrical reliability, double refractive index, and the like.

The content of the compounds relative to the total mass is 1 to 40 mass % in one embodiment, 1 to 35 mass % in another embodiment, 1 to 30 mass % in still another embodiment, 1 to 25 mass % in still yet another embodiment, 1 to 10 mass % in still yet another embodiment, 1 to 7 mass % in still yet another embodiment, and 1 to 5 mass % in still yet another embodiment.

Furthermore, the compounds represented by the general formula (IX-1-1) are preferably compounds represented by formula (28.1) to formula (28.5). The liquid crystal composition preferably contains one or two of the compounds represented by the formula (28.3) and the formula (28.5).

[Chem. 91]

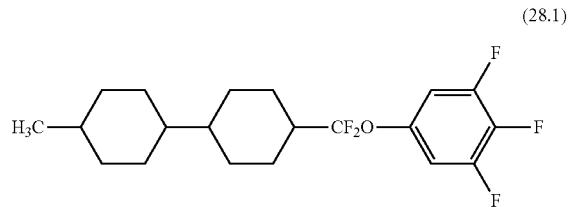

(28.1)

(28.2)

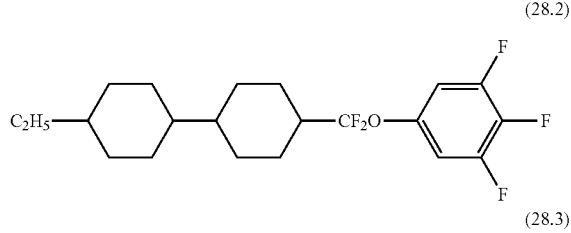

(28.3)

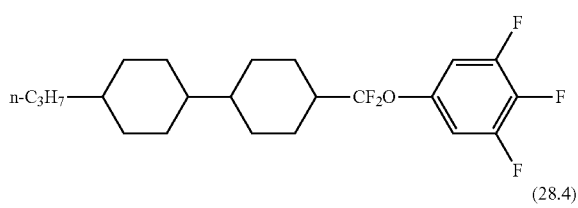

(28.4)

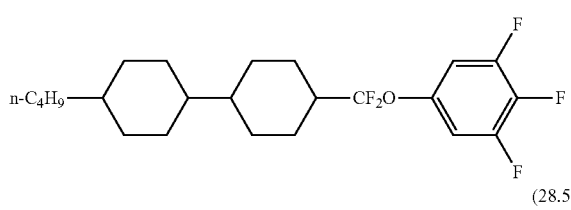

(28.5)

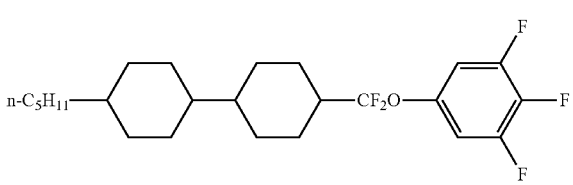

In the liquid crystal composition of the present invention, the content of the compound represented by the formula (28.3) is preferably 1 mass % or more and 30 mass % or less, more preferably 2 mass % or more and 20 mass % or less, more preferably 2 mass % or more and 15 mass % or less, particularly preferably 2 mass % or more and 10 mass % or less, and most preferably 2 mass % or more and 7 mass % or less relative to the total mass of the liquid crystal composition in consideration of solubility at low temperature, transition temperature, electrical reliability, and the like.

Examples of the content in the most preferable range include 2 mass % or more and 5 mass % or less, 2 mass % or more and 4 mass % or less, 2 mass % or more and 3 mass % or less, 3 mass % or more and 7 mass % or less, 4 mass % or more and 7 mass % or less, 5 mass % or more and 7 mass % or less, and 6 mass % or more and 7 mass % or less.

In the liquid crystal composition of the present invention, the content of the compound represented by the formula (28.5) is preferably 3 mass % or more and 25 mass % or less, more preferably 5 mass % or more and 20 mass % or less, more preferably 5 mass % or more and 15 mass % or less, more preferably 5 mass % or more and 10 mass % or less, and most preferably 5 mass % or more and 8 mass % or less relative to the total mass of the liquid crystal composition in consideration of solubility at low temperature, transition temperature, electrical reliability, and the like.

Examples of the content in the most preferable range include 5 mass % or more and 7 mass % or less, 5 mass % or more and 6 mass % or less, 6 mass % or more and 8 mass % or less, and 7 mass % or more and 8 mass % or less.

In the liquid crystal composition of the present invention, the total content of the compound represented by the formula (28.3) and the compound represented by the formula (28.5) is preferably 5 mass % or more and 30 mass % or less, more preferably 7 mass % or more and 20 mass % or less, and more preferably 10 mass % or more and 15 mass % or less relative to the total mass of the liquid crystal composition.

Examples of the content in the more preferable range include 10 mass % or more and 14 mass % or less, 10 mass % or more and 12 mass % or less, 12 mass % or more and 15 mass % or less, and 14 mass % or more and 15 mass % or less.

When the liquid crystal composition contains the compound represented by the formula (28.3) and the compound represented by the formula (28.5), the content of the compound represented by the formula (28.3) may be higher than that of the compound represented by the formula (28.5) or the content of the compound represented by the formula (28.5) may be higher than that of the compound represented by the formula (28.3). However, the content of the compound represented by the formula (28.5) is preferably higher than that of the compound represented by the formula (28.3) in terms of increase in Tni of the liquid crystal composition.

Furthermore, the compounds represented by the general formula (IX-1) are preferably compounds represented by general formula (IX-1-2).

[Chem. 92]

(IX-1-2)

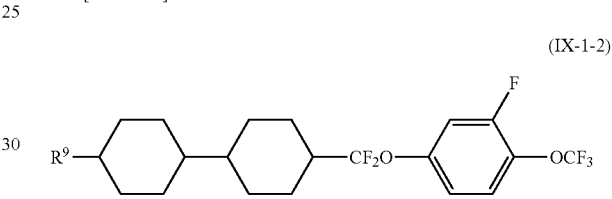

(In the formula, $R^9$ represents an alkyl group having 1 to 5 carbon atoms, an alkenyl group having 2 to 5 carbon atoms, or an alkoxy group having 1 to 4 carbon atoms.)

Although the number of compounds that can be combined with each other is not particularly limited, one to three of the plurality of compounds represented by the general formula (IX-1-2) are preferably combined and one to four of the compounds are more preferably combined in consideration of solubility at low temperature, transition temperature, electrical reliability, double refractive index, and the like.

The content of the compounds represented by the general formula (IX-1-2) is preferably 1 mass % or more and 30 mass % or less, more preferably 5 mass % or more and 30 mass % or less, more preferably 8 mass % or more and 30 mass % or less, more preferably 10 mass % or more and 25 mass % or less, more preferably 14 mass % or more and 22 mass % or less, and particularly preferably 16 mass % or more and 20 mass % or less relative to the total mass of the liquid crystal composition of the present invention in consideration of solubility at low temperature, transition temperature, electrical reliability, and the like.

Furthermore, the compounds represented by the general formula (IX-1-2) are preferably compounds represented by formula (29.1) to formula (29.4) and more preferably a compound represented by formula (29.2) or a compound represented by formula (29.4).

[Chem. 93]

(29.1)

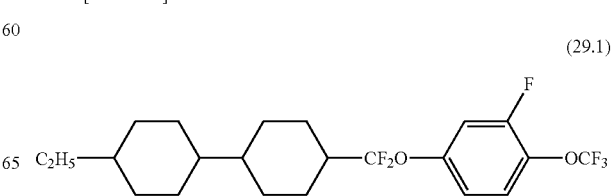

-continued (29.2)
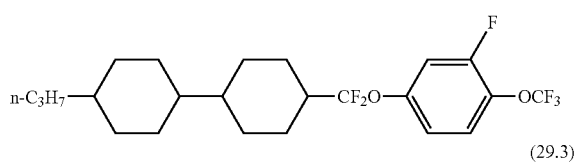

(29.3)
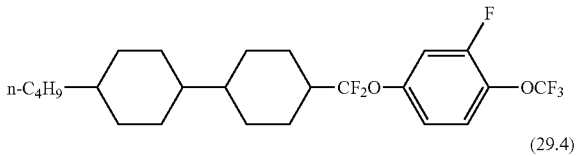

(29.4)
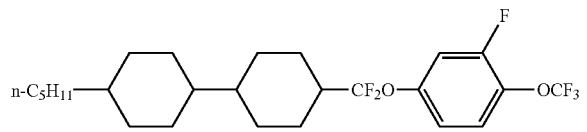

Furthermore, the compounds represented by the general formula (IX) are preferably compounds represented by general formula (IX-2).

[Chem. 94]

(IX-2)
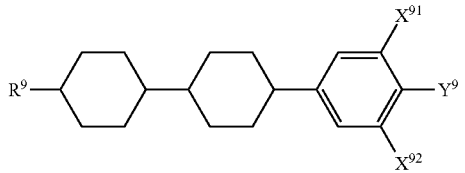

(In the formula, $R^9$ represents an alkyl group having 1 to 5 carbon atoms, an alkenyl group having 2 to 5 carbon atoms, or an alkoxy group having 1 to 4 carbon atoms; $X^{91}$ and $X^{92}$ each independently represent a hydrogen atom or a fluorine atom; and $Y^9$ represents a fluorine atom, a chlorine atom, or —$OCF_3$.)

Although the number of compounds that can be combined with each other is not particularly limited, the plurality of compounds represented by the general formula (IX-2) can be used in combination for each embodiment in consideration of solubility at low temperature, transition temperature, electrical reliability, double refractive index, and the like. For example, the number of the compounds is one in one embodiment of the present invention. The number of the compounds is two in another embodiment. The number of the compounds is three in still another embodiment. The number of the compounds is four in still yet another embodiment. The number of the compounds is five in still yet another embodiment. The number of the compounds is six or more in still yet another embodiment.

Furthermore, the compounds represented by the general formula (IX-2) are preferably compounds represented by general formula (IX-2-1).

[Chem. 95]

(IX-2-1)

(In the formula, $R^9$ represents an alkyl group having 1 to 5 carbon atoms, an alkenyl group having 2 to 5 carbon atoms, or an alkoxy group having 1 to 4 carbon atoms.)

Although the number of compounds that can be combined with each other is not particularly limited, one to three of the plurality of compounds represented by the general formula (IX-2-1) are preferably combined in consideration of solubility at low temperature, transition temperature, electrical reliability, double refractive index, and the like.

The content of the compounds represented by the general formula (IX-2-1) has a preferred upper limit and a preferred lower limit for each embodiment in consideration of characteristics such as solubility at low temperature, transition temperature, electrical reliability, and double refractive index.

For example, the content of the compounds is 1 to 40 mass % relative to the total mass of the liquid crystal composition of the present invention in one embodiment of the present invention, 2 to 40 mass % in another embodiment, 4 to 40 mass % in still another embodiment, 10 to 40 mass % in still yet another embodiment, 14 to 40 mass % in still yet another embodiment, 16 to 40 mass % in still yet another embodiment, and 21 to 40 mass % in still yet another embodiment.

Furthermore, for example, the content of the compounds is 1 to 40 mass % relative to the total mass in one embodiment of the present invention, 1 to 35 mass % in another embodiment, 1 to 30 mass % in still another embodiment, 1 to 25 mass % in still yet another embodiment, 1 to 22 mass % in still yet another embodiment, 1 to 20 mass % in still yet another embodiment, 1 to 10 mass % in still yet another embodiment, 1 to 7 mass % in still yet another embodiment, and 1 to 5 mass % in still yet another embodiment.

Furthermore, the compounds represented by the general formula (IX-2-1) are preferably compounds represented by formula (30.1) to formula (30.4) and more preferably compounds represented by formula (30.1) and formula (30.2).

[Chem. 96]

(30.1)
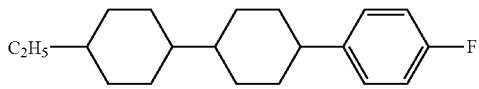

(30.2)
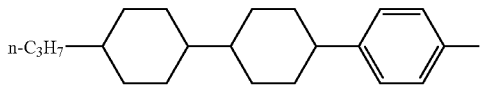

(30.3)
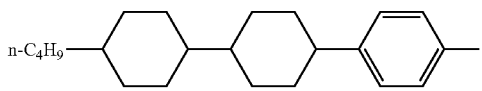

(30.4)
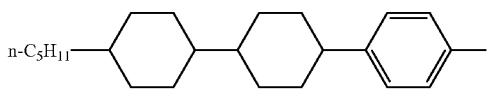

Furthermore, the compounds represented by the general formula (IX-2) are preferably compounds represented by general formula (IX-2-2).

[Chem. 97]

(IX-2-2)

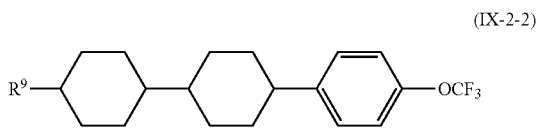

(In the formula, $R^9$ represents an alkyl group having 1 to 5 carbon atoms, an alkenyl group having 2 to 5 carbon atoms, or an alkoxy group having 1 to 4 carbon atoms.)

Although the number of compounds that can be combined with each other is not particularly limited, one to three of the plurality of compounds represented by the general formula (IX-2-2) are preferably combined and one to four of the compounds are more preferably combined in consideration of solubility at low temperature, transition temperature, electrical reliability, double refractive index, and the like.

The content of the compounds represented by the general formula (IX-2-2) has an upper limit and a lower limit for each embodiment in consideration of characteristics such as solubility at low temperature, transition temperature, electrical reliability, and double refractive index. For example, the content of the compounds is 1 to 40 mass % relative to the total mass of the liquid crystal composition of the present invention in one embodiment of the present invention, 2 to 40 mass % in another embodiment, 4 to 40 mass % in still another embodiment, 10 to 40 mass % in still yet another embodiment, 14 to 40 mass % in still yet another embodiment, 16 to 40 mass % in still yet another embodiment, and 21 to 40 mass % in still yet another embodiment.

Furthermore, for example, the content of the compounds is 1 to 40 mass % relative to the total mass in one embodiment of the present invention, 1 to 35 mass % in another embodiment, 1 to 30 mass % in still another embodiment, 1 to 25 mass % in still yet another embodiment, 1 to 22 mass % in still yet another embodiment, 1 to 15 mass % in still yet another embodiment, 1 to 12 mass % in still yet another embodiment, 1 to 8 mass % in still yet another embodiment, and 1 to 4 mass % in still yet another embodiment.

Furthermore, the compounds represented by the general formula (IX-2-2) are preferably compounds represented by formula (31.1) to formula (31.4), more preferably compounds represented by formula (31.2) to formula (31.4), and more preferably a compound represented by formula (31.2).

[Chem. 98]

(31.1)

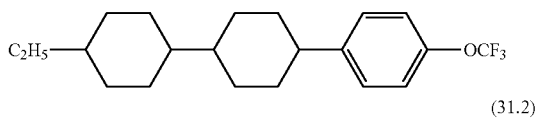

(31.2)

(31.3)

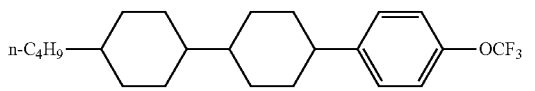

(31.4)

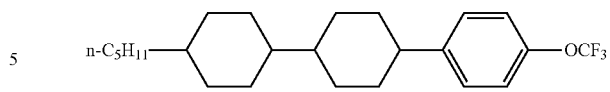

In the liquid crystal composition of the present invention, the content of the compound represented by the formula (31.2) is preferably 1 mass % or more and 35 mass % or less, more preferably 2 mass % or more and 25 mass % or less, more preferably 3 mass % or more and 15 mass % or less, particularly preferably 4 mass % or more and 10 mass % or less, and most preferably 5 mass % or more and 6 mass % or less relative to the total mass of the liquid crystal composition of the present invention.

In the liquid crystal composition of the present invention, the content of the compound represented by the formula (31.4) is preferably 1 mass % or more and 35 mass % or less, more preferably 1 mass % or more and 25 mass % or less, and more preferably 1 mass % or more and 15 mass % or less relative to the total mass of the liquid crystal composition of the present invention.

Furthermore, the compounds represented by the general formula (IX-2) are preferably compounds represented by general formula (IX-2-3).

[Chem. 99]

(IX-2-3)

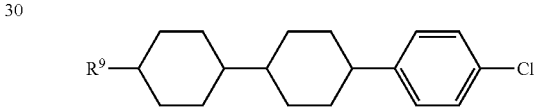

(In the formula, $R^9$ represents an alkyl group having 1 to 5 carbon atoms, an alkenyl group having 2 to 5 carbon atoms, or an alkoxy group having 1 to 4 carbon atoms.)

Although the number of compounds that can be combined with each other is not particularly limited, one or two compounds among the plurality of compounds represented by the general formula (IX-2-3) are preferably combined in consideration of solubility at low temperature, transition temperature, electrical reliability, double refractive index, and the like.

The content of the compounds represented by the general formula (IX-2-3) is preferably 1 mass % or more and 30 mass % or less, 3 mass % or more and 20 mass % or less, more preferably 6 mass % or more and 15 mass % or less, and more preferably 8 mass % or more and 10 mass % or less relative to the total mass of the liquid crystal composition of the present invention in consideration of solubility at low temperature, transition temperature, electrical reliability, and the like.

Furthermore, the compounds represented by the general formula (IX-2-3) are preferably compounds represented by formula (32.1) to formula (32.4) and more preferably a compound represented by formula (32.2) and/or a compound represented by formula (32.4).

[Chem. 100]

(32.1)

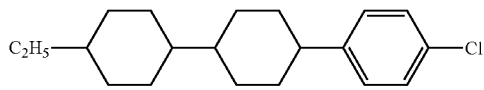

-continued (32.2)
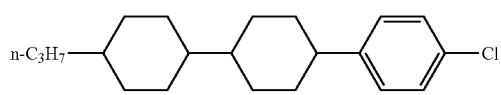

(32.3)
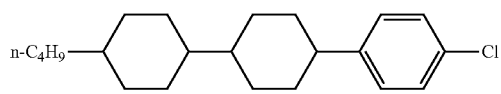

(32.4)
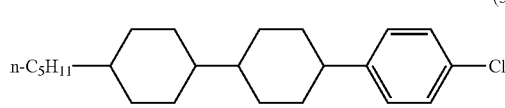

Furthermore, the compounds represented by the general formula (IX-2) are preferably compounds represented by general formula (IX-2-4).

[Chem. 101]

(IX-2-4)
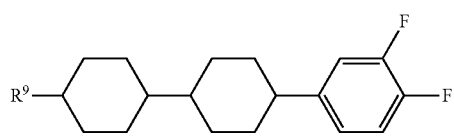

(In the formula, $R^9$ represents an alkyl group having 1 to 5 carbon atoms, an alkenyl group having 2 to 5 carbon atoms, or an alkoxy group having 1 to 4 carbon atoms.)

The content of the compounds represented by the general formula (IX-2-4) is preferably 1 mass % or more and 30 mass % or less, 3 mass % or more and 20 mass % or less, more preferably 6 mass % or more and 15 mass % or less, and particularly preferably 8 mass % or more and 10 mass % or less relative to the total mass of the liquid crystal composition of the present invention in consideration of solubility at low temperature, transition temperature, electrical reliability, and the like.

Furthermore, the compounds represented by the general formula (IX-2-4) are preferably compounds represented by formula (33.1) to formula (33.5) and more preferably a compound represented by formula (33.1) and/or a compound represented by formula (33.3).

[Chem. 102]

(33.1)
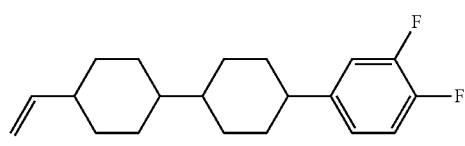

(33.2)
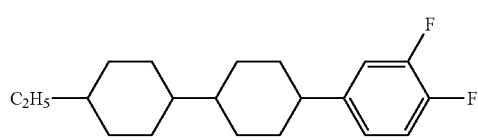

(33.3)
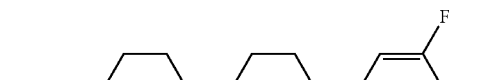

(33.4)
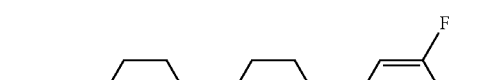

(33.5)
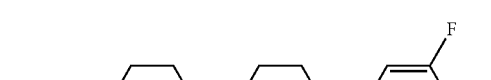

(33.6)
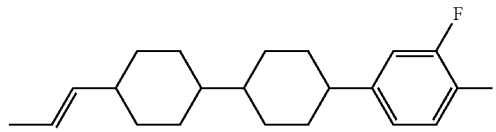

Furthermore, the compounds represented by the general formula (IX-2) are preferably compounds represented by general formula (IX-2-5).

[Chem. 103]

(IX-2-5)
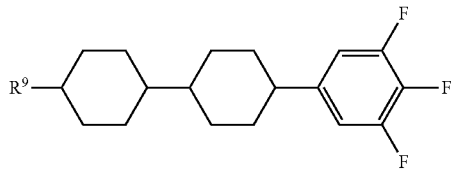

(In the formula, $R^9$ represents an alkyl group having 1 to 5 carbon atoms, an alkenyl group having 2 to 5 carbon atoms, or an alkoxy group having 1 to 4 carbon atoms.)

Although the number of compounds that can be combined with each other is not particularly limited, the plurality of compounds represented by the general formula (IX-2-5) can be suitably used in combination for each embodiment in consideration of solubility at low temperature, transition temperature, electrical reliability, double refractive index, and the like. For example, the number of the compounds is one in one embodiment of the present invention. The number of the compounds is two in another embodiment. The number of the compounds is three in still another embodiment. The number of the compounds is four or more in still yet another embodiment.

The content of the compounds represented by the general formula (IX-2-5) has an upper limit and a lower limit for each embodiment in consideration of characteristics such as solubility at low temperature, transition temperature, electrical reliability, and double refractive index. For example, the content of the compounds is 4 to 45 mass % relative to the total mass of the liquid crystal composition of the present invention in one embodiment of the present invention, 8 to 45 mass % in another embodiment, 12 to 45 mass % in still another embodiment, 21 to 45 mass % in still yet another embodiment, 30 to 45 mass % in still yet another embodiment, 31 to 45 mass % in still yet another embodiment, and 34 to 45 mass % in still yet another embodiment. Furthermore, for example, the content of the compounds is 4 to 45 mass % relative to the total mass in one embodiment of the present invention, 4 to 40 mass % in another embodiment, 4 to 35 mass % in still another embodiment, 4 to 32 mass % in still yet another embodiment, 4 to 22 mass % in still yet another embodiment, 4 to 13 mass % in still yet another embodiment, 4 to 9 mass % in still yet another embodiment, 4 to 8 mass % in still yet another embodiment, and 4 to 5 mass % in still yet another embodiment.

When the liquid crystal composition of the present invention needs to have low viscosity to achieve high response speed, the lower limit and the upper limit are preferably set to be low. When the liquid crystal composition of the present invention needs to have high Tni to suppress the generation of image sticking, the lower limit and the upper limit are preferably set to be low. When the dielectric anisotropy is increased to maintain low drive voltage, the lower limit and the upper limit are preferably set to be high.

Furthermore, the compounds represented by the general formula (IX-2-5) are preferably compounds represented by formula (34.1) to formula (34.5) and more preferably a compound represented by formula (34.1), a compound represented by formula (34.2), a compound represented by formula (34.3), and/or a compound represented by formula (34.5).

[Chem. 104]

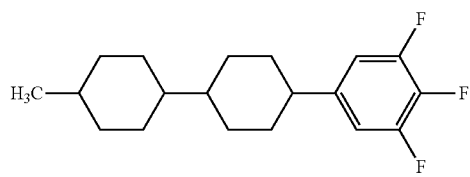
(34.1)

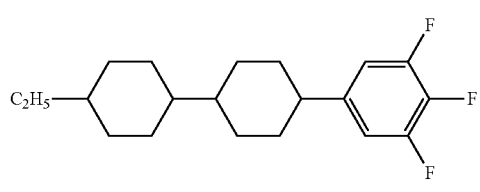
(34.2)

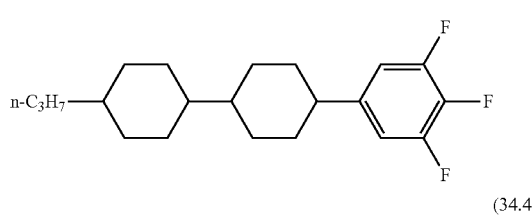
(34.3)

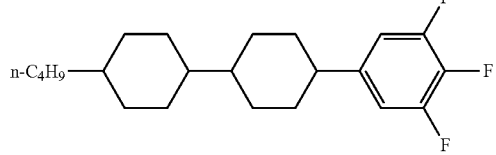
(34.4)

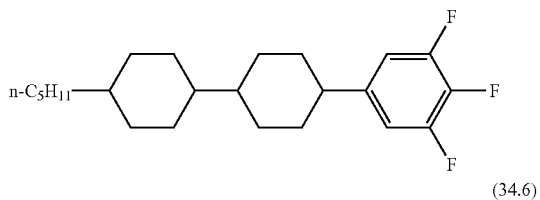
(34.5)

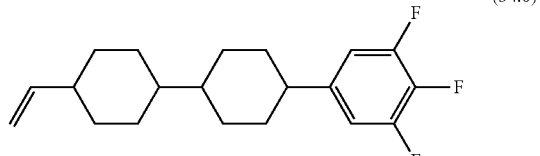
(34.6)

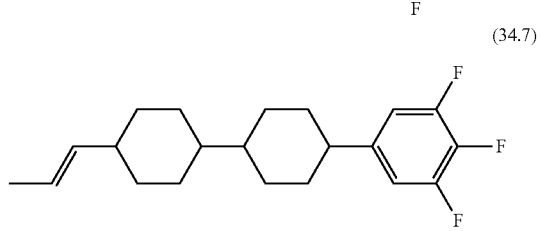
(34.7)

Furthermore, the compounds represented by the general formula (IX) are preferably compounds represented by general formula (IX-3).

[Chem. 105]

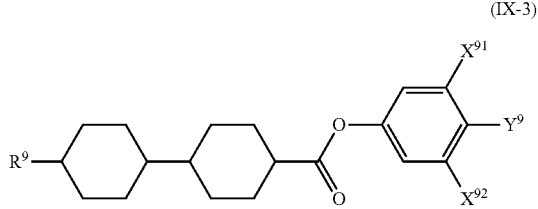
(IX-3)

(In the formula, $R^9$ represents an alkyl group having 1 to 5 carbon atoms, an alkenyl group having 2 to 5 carbon atoms, or an alkoxy group having 1 to 4 carbon atoms; $X^{91}$ and $X^{92}$ each independently represent a hydrogen atom or a fluorine atom; $Y^9$ represents a fluorine atom, a chlorine atom, or —$OCF_3$.)

Furthermore, the compounds represented by the general formula (IX-3) are preferably compounds represented by general formula (IX-3-1).

[Chem. 106]

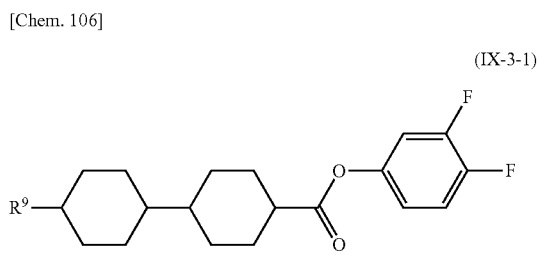
(IX-3-1)

(In the formula, $R^9$ represents an alkyl group having 1 to 5 carbon atoms, an alkenyl group having 2 to 5 carbon atoms, or an alkoxy group having 1 to 4 carbon atoms.)

Although the number of compounds that can be combined with each other is not particularly limited, one or two of the plurality of compounds represented by the general formula (IX-3-1) are preferably combined in consideration of solubility at low temperature, transition temperature, electrical reliability, double refractive index, and the like.

The content of the compounds represented by the general formula (IX-3-1) is preferably 3 mass % or more and 30 mass % or less, more preferably 7 mass % or more and 30 mass % or less, more preferably 13 mass % or more and 20 mass % or less, and particularly preferably 15 mass % or more and 18 mass % or less relative to the total mass of the liquid crystal composition of the present invention in consideration of solubility at low temperature, transition temperature, electrical reliability, and the like.

Furthermore, the compounds represented by the general formula (IX-3-1) are preferably compounds represented by formula (35.1) to formula (35.4) and more preferably a compound represented by formula (35.1) and/or a compound represented by formula (35.2).

[Chem. 107]

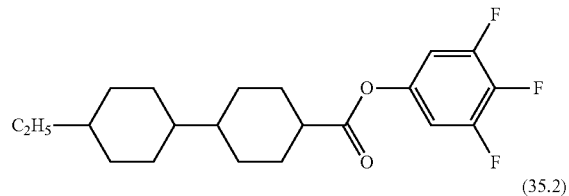

(35.1)

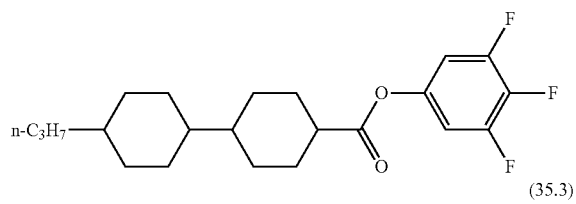

(35.2)

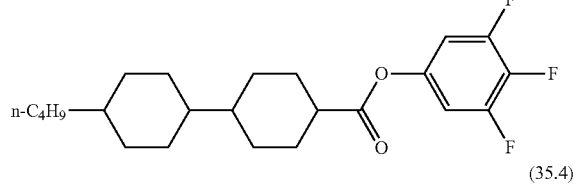

(35.3)

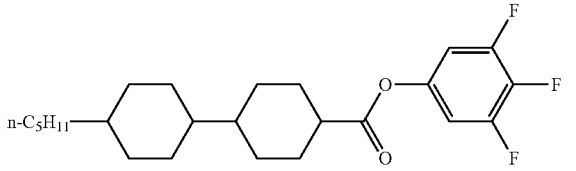

(35.4)

Furthermore, the compounds represented by the general formula (M) are preferably compounds represented by general formula (X). Note that the compounds represented by the general formula (M) exclude the compounds represented by general formula (i) and the compounds represented by the general formula (ii).

[Chem. 108]

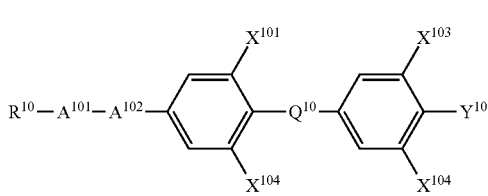

(X)

(In the formula, $X^{101}$ to $X^{104}$ each independently represent a fluorine atom or a hydrogen atom; $Y^{10}$ represents a fluorine atom, a chlorine atom, or $-OCF_3$; $Q^{10}$ represents a single bond or $-CF_2O-$; $R^{10}$ represents an alkyl group having 1 to 5 carbon atoms, an alkenyl group having 2 to 5 carbon atoms, or an alkoxy group having 1 to 4 carbon atoms; and $A^{101}$ and $A^{102}$ each independently represent a 1,4-cyclohexylene group, a 1,4-phenylene group, or

[Chem. 109]

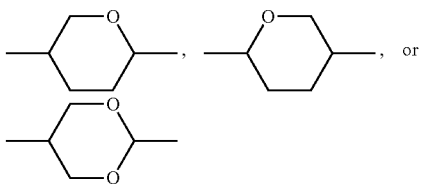

, or where hydrogen atoms on the 1,4-phenylene group may be substituted with fluorine atoms.)

Although the number of compounds that can be combined with each other is not particularly limited, the plurality of compounds represented by the general formula (X) can be suitably used in combination for each embodiment in consideration of solubility at low temperature, transition temperature, electrical reliability, double refractive index, and the like. For example, the number of the compounds is one in one embodiment of the present invention. The number of the compounds is two in another embodiment. The number of the compounds is three in still another embodiment. The number of the compounds is four in still yet another embodiment. The number of the compounds is five or more in still yet another embodiment.

The content of the compounds represented by the general formula (X) has an upper limit and a lower limit for each embodiment in consideration of characteristics such as solubility at low temperature, transition temperature, electrical reliability, and double refractive index. For example, the content of the compounds is 2 to 45 mass % relative to the total mass of the liquid crystal composition of the present invention in one embodiment of the present invention, 3 to 45 mass % in another embodiment, 6 to 45 mass % in still another embodiment, 8 to 45 mass % in still yet another embodiment, 9 to 45 mass % in still yet another embodiment, 11 to 45 mass % in still yet another embodiment, 12 to 45 mass % in still yet another embodiment, 18 to 45 mass % in still yet another embodiment, 19 to 45 mass % in still yet another embodiment, 23 to 45 mass % in still yet another embodiment, and 25 to 45 mass % in still yet another embodiment. Furthermore, for example, the content of the compounds is 2 to 45 mass % relative to the total mass in one embodiment of the present invention, 2 to 35 mass % in another embodiment, 2 to 30 mass % in still another embodiment, 2 to 25 mass % in still yet another embodiment, 2 to 20 mass % in still yet another embodiment, 2 to 13 mass % in still yet another embodiment, 2 to 9 mass % in still yet another embodiment, 2 to 6 mass % in still yet another embodiment, and 2 to 3 mass % in still yet another embodiment.

When the liquid crystal composition of the present invention needs to have low viscosity to achieve high response speed, the lower limit and the upper limit are preferably set to be low. When a liquid crystal composition which does not easily cause image sticking is required, the lower limit and the upper limit are preferably set to be low. When the dielectric anisotropy is increased to maintain low drive voltage, the lower limit and the upper limit are preferably set to be high.

The compounds represented by the general formula (X) and used for the liquid crystal composition of the present invention are preferably compounds represented by general formula (X-1).

[Chem. 110]

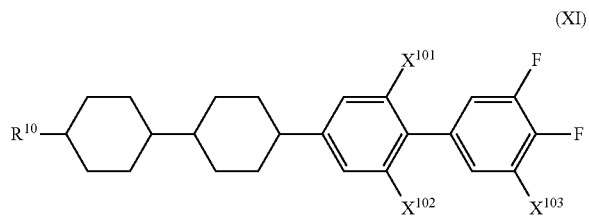

(XI)

(In the formula, $X^{101}$ to $X^{103}$ each independently represent a fluorine atom or a hydrogen atom; and $R^{10}$ represents an alkyl group having 1 to 5 carbon atoms, an alkenyl group having 2 to 5 carbon atoms, or an alkoxy group having 1 to 4 carbon atoms.)

Although the number of compounds that can be combined with each other is not particularly limited, the plurality of compounds represented by the general formula (X-1) can be suitably used in combination for each embodiment in consideration of solubility at low temperature, transition temperature, electrical reliability, double refractive index, and the like. For example, the number of the compounds is one in one embodiment of the present invention. The number of the compounds is two in another embodiment. The number of the compounds is three in still another embodiment. The number of the compounds is four in still yet another embodiment. The number of the compounds is five or more in still yet another embodiment.

The content of the compounds represented by the general formula (X-1) has an upper limit and a lower limit for each embodiment in consideration of characteristics such as solubility at low temperature, transition temperature, electrical reliability, and double refractive index. For example, the content of the compounds is 2 to 40 mass % relative to the total mass of the liquid crystal composition of the present invention in one embodiment of the present invention, 3 to 40 mass % in another embodiment, 5 to 40 mass % in still another embodiment, 6 to 40 mass % in still yet another embodiment, 7 to 40 mass % in still yet another embodiment, 8 to 40 mass % in still yet another embodiment, 9 to 40 mass % in still yet another embodiment, 13 to 40 mass % in still yet another embodiment, 18 to 40 mass % in still yet another embodiment, and 23 to 40 mass % in still yet another embodiment.

Furthermore, for example, the content of the compounds is 2 to 40 mass % relative to the total mass in one embodiment of the present invention, 2 to 30 mass % in another embodiment, 2 to 25 mass % in still another embodiment, 2 to 20 mass % in still yet another embodiment, 2 to 15 mass % in still yet another embodiment, 2 to 10 mass % in still yet another embodiment, 2 to 6 mass % in still yet another embodiment, and 2 to 4 mass % in still yet another embodiment.

Furthermore, the compounds represented by the general formula (X-1) and used for the liquid crystal composition of the present invention are preferably compounds represented by general formula (X-1-1).

[Chem. 111]

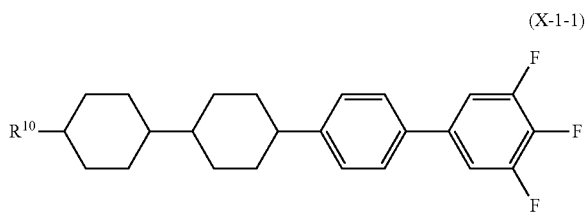

(X-1-1)

(In the formula, $R^{10}$ represents an alkyl group having 1 to 5 carbon atoms, an alkenyl group having 2 to 5 carbon atoms, or an alkoxy group having 1 to 4 carbon atoms.)

Although the number of compounds that can be combined with each other is not particularly limited, the plurality of compounds represented by the general formula (X-1-1) can be suitably used in combination for each embodiment in consideration of solubility at low temperature, transition temperature, electrical reliability, double refractive index, and the like. For example, the number of the compounds is one in one embodiment of the present invention. The number of the compounds is two in another embodiment. The number of the compounds is three in still another embodiment. The number of the compounds is four or more in still yet another embodiment.

The content of the compounds represented by the general formula (X-1-1) has an upper limit and a lower limit for each embodiment in consideration of characteristics such as solubility at low temperature, transition temperature, electrical reliability, and double refractive index. For example, the content of the compounds is 3 to 30 mass % relative to the total mass of the liquid crystal composition of the present invention in one embodiment of the present invention, 4 to 30 mass % in another embodiment, 6 to 30 mass % in still another embodiment, 9 to 30 mass % in still yet another embodiment, 12 to 30 mass % in still yet another embodiment, 15 to 30 mass % in still yet another embodiment, 18 to 30 mass % in still yet another embodiment, and 21 to 30 mass % in still yet another embodiment.

Furthermore, for example, the content of the compounds is 3 to 30 mass % relative to the total mass in one embodiment of the present invention, 3 to 20 mass % in another embodiment, 3 to 13 mass % in still another embodiment, 3 to 10 mass % in still yet another embodiment, and 3 to 7 mass % in still yet another embodiment.

More specifically, the compounds represented by the general formula (X-1-1) are preferably compounds represented by formula (36.1) to formula (36.4) and more preferably a compound represented by formula (36.1) and/or a compound represented by formula (36.2).

[Chem. 112]

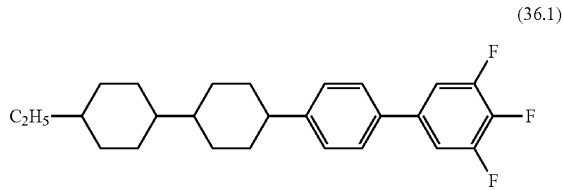

(36.1)

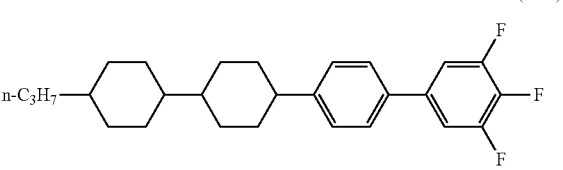

(36.2)

(36.3)

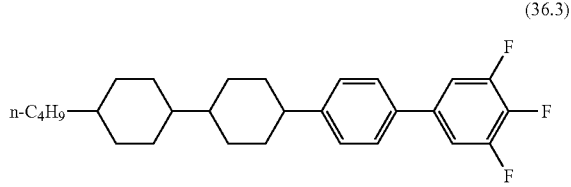

(36.4)

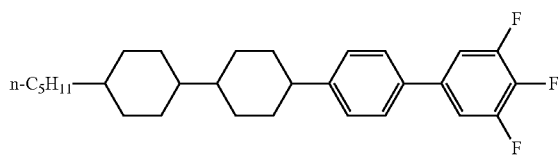

Furthermore, the compounds represented by the general formula (X-1) and used for the liquid crystal composition of the present invention are preferably compounds represented by general formula (X-1-2).

[Chem. 113]

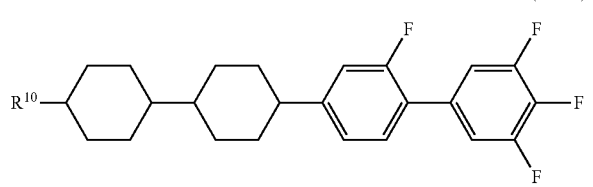

(X-1-2)

(In the formula, $R^{10}$ represents an alkyl group having 1 to 5 carbon atoms, an alkenyl group having 2 to 5 carbon atoms, or an alkoxy group having 1 to 4 carbon atoms.)

The content of the compounds represented by the general formula (X-1-2) is preferably 1 mass % or more, more preferably 2 mass % or more, and more preferably 6 mass % or more relative to the total mass of the liquid crystal composition of the present invention. The maximum content is preferably 20 mass % or less, more preferably 16 mass % or less, more preferably 12 mass % or less, and particularly preferably 10 mass % or less in consideration of solubility at low temperature, transition temperature, electrical reliability, and the like.

Specific examples of the content in the preferable range include 1 to 10 mass %, 2 to 8 mass %, 2 to 7 mass %, 2 to 5 mass %, 4 to 8 mass %, and 5 to 8 mass %.

More specifically, the compounds represented by the general formula (X-1-2) are preferably compounds represented by formula (37.1) to formula (37.4) and more preferably a compound represented by formula (37.2).

[Chem. 114]

(37.1)

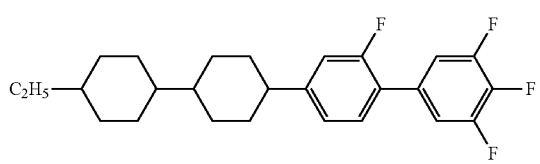

(37.2)

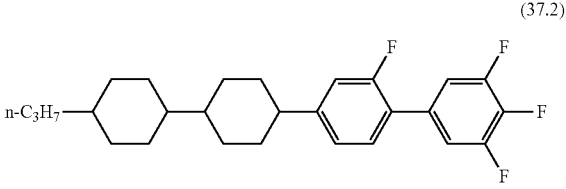

(37.3)

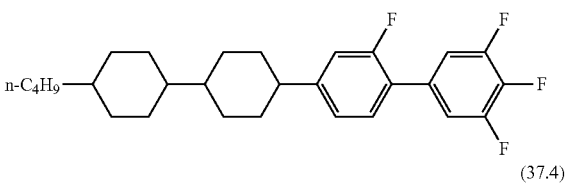

(37.4)

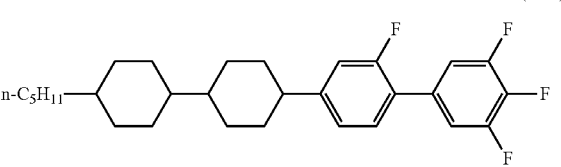

In the liquid crystal composition of the present invention, the content of the compound represented by the formula (37.2) is preferably 1 mass % or more and 20 mass % or less, more preferably 1 to 10 mass %, more preferably 2 to 8 mass %, and particularly preferably 3 to 5 mass % relative to the total mass of the liquid crystal composition of the present invention in consideration of solubility at low temperature, transition temperature, electrical reliability, and the like. In the particularly preferable range, the content may be 3 to 4 mass % or 4 to 5 mass %.

Furthermore, the compounds represented by the general formula (X-1) and used for the liquid crystal composition of the present invention are preferably compounds represented by general formula (X-1-3).

[Chem. 115]

(X-1-3)

(In the formula, $R^{10}$ represents an alkyl group having 1 to 5 carbon atoms, an alkenyl group having 2 to 5 carbon atoms, or an alkoxy group having 1 to 4 carbon atoms.)

Although the number of compounds that can be combined with each other is not particularly limited, one or more of the compounds represented by the general formula (X-1-3) are preferably combined in consideration of solubility at low temperature, transition temperature, electrical reliability, double refractive index, and the like.

The content of the compounds represented by the general formula (X-1-3) is preferably 1 mass % or more, more preferably 2 mass % or more, and more preferably 6 mass % or more relative to the total mass of the liquid crystal composition of the present invention. The maximum content is preferably 20 mass % or less, more preferably 16 mass % or less, more preferably 12 mass % or less, and particularly preferably 10 mass % or less in consideration of solubility at low temperature, transition temperature, electrical reliability, and the like.

Specific examples of the content in the preferable range include 1 to 10 mass %, 3 to 8 mass %, 2 to 6 mass %, 2 to 5 mass %, 2 to 4 mass %, 3 to 6 mass %, 4 to 6 mass %, and 5 to 6 mass %.

More specifically, the compounds represented by the general formula (X-1-3) are preferably compounds represented by formula (38.1) to formula (38.4) and more preferably a compound represented by formula (38.2).

[Chem. 116]

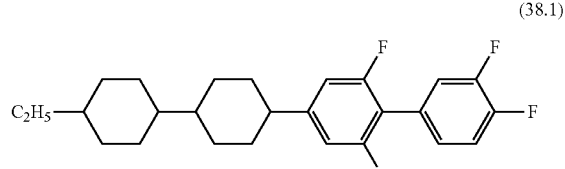
(38.1)

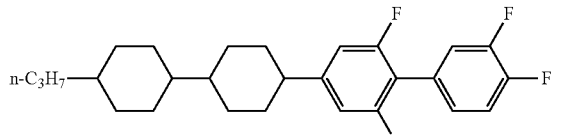
(38.2)

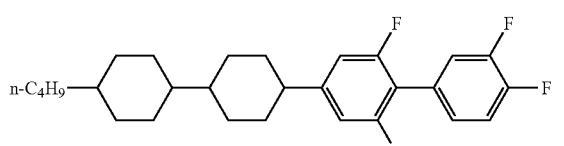
(38.3)

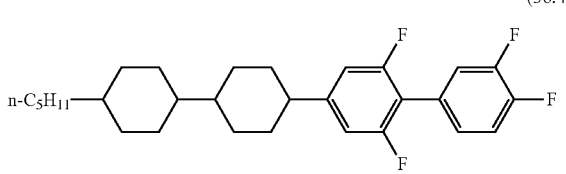
(38.4)

In the liquid crystal composition of the present invention, the content of the compound represented by the formula (38.2) is preferably 1 mass % or more and 35 mass % or less, more preferably 2 mass % or more and 25 mass % or less, more preferably 3 mass % or more and 20 mass % or less, more preferably 3 mass % or more and 15 mass % or less, more preferably 3 mass % or more and 10 mass % or less, more preferably 3 mass % or more and 8 mass % or less, and particularly preferably 4 mass % or more and 6 mass % or less relative to the total mass of the liquid crystal composition of the present invention.

The compounds represented by the general formula (X) and used for the liquid crystal composition of the present invention are preferably compounds represented by general formula (X-2).

[Chem. 117]

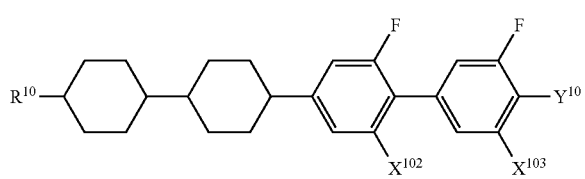
(X-2)

(In the formula, $X^{102}$ and $X^{103}$ each independently represent a fluorine atom or a hydrogen atom; $Y^{10}$ represents a fluorine atom, a chlorine atom, or $-OCF_3$; and $R^{10}$ represents an alkyl group having 1 to 5 carbon atoms, an alkenyl group having 2 to 5 carbon atoms, or an alkoxy group having 1 to 4 carbon atoms.)

Although the number of compounds that can be combined with each other is not particularly limited, one or more of the plurality of compounds represented by the general formula (X-2) are preferably combined in consideration of solubility at low temperature, transition temperature, electrical reliability, double refractive index, and the like.

Furthermore, the compounds represented by the general formula (X) are preferably compounds represented by general formula (X-3).

[Chem. 118]

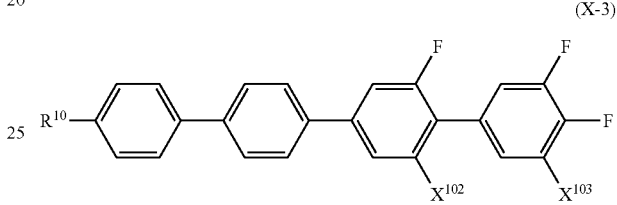
(X-3)

(In the formula, $X^{102}$ and $X^{103}$ each independently represent a fluorine atom or a hydrogen atom; and $R^{10}$ represents an alkyl group having 1 to 5 carbon atoms, an alkenyl group having 2 to 5 carbon atoms, or an alkoxy group having 1 to 4 carbon atoms.)

Although the number of compounds that can be combined with each other is not particularly limited, one or more of the plurality of compounds represented by the general formula (X-3) are preferably combined in consideration of solubility at low temperature, transition temperature, electrical reliability, double refractive index, and the like.

Furthermore, the compounds represented by the general formula (X-3) and used for the liquid crystal composition of the present invention are preferably compounds represented by general formula (X-3-1).

[Chem. 119]

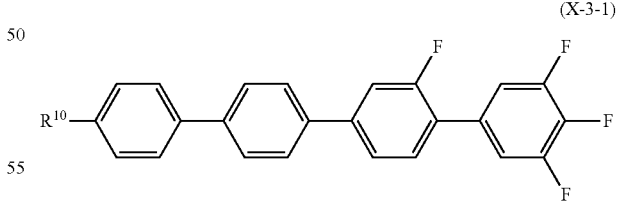
(X-3-1)

(In the formula, $R^{10}$ represents an alkyl group having 1 to 5 carbon atoms, an alkenyl group having 2 to 5 carbon atoms, or an alkoxy group having 1 to 4 carbon atoms.)

Although the number of compounds that can be combined with each other is not particularly limited, one or more of the plurality of compounds represented by the general formula (X-3-1) are preferably combined in consideration of solubility at low temperature, transition temperature, electrical reliability, double refractive index, and the like.

The content of the compounds represented by the general formula (X-3-1) is preferably 1 mass % or more, more preferably 2 mass % or more, and more preferably 3 mass % or more relative to the total mass of the liquid crystal composition of the present invention. The maximum content is preferably 10 mass % or less, more preferably 8 mass % or less, more preferably 6 mass % or less, and particularly preferably 4 mass % or less in consideration of solubility at low temperature, transition temperature, electrical reliability, and the like.

More specifically, the compounds represented by the general formula (X-3-1) and used for the liquid crystal composition of the present invention are preferably compounds represented by formula (41.1) to formula (41.4) and more preferably a compound represented by formula (41.2).

[Chem. 120]

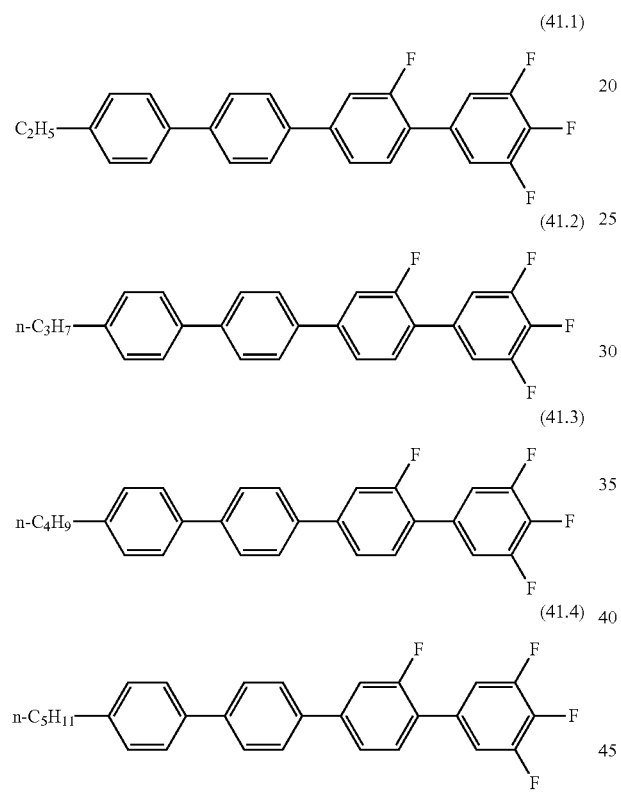

In the liquid crystal composition of the present invention, the content of the compound represented by the formula (41.2) is preferably 0.5 mass % or more and 15 mass % or less and more preferably 1 mass % or more and 10 mass % or less relative to the total mass of the liquid crystal composition of the present invention.

Furthermore, the compounds represented by the general formula (X) are preferably compounds represented by general formula (X-4).

[Chem. 121]

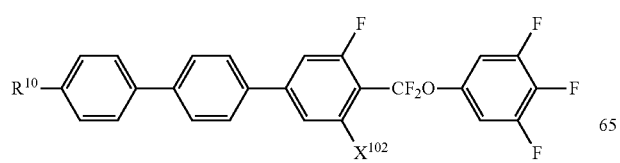

(In the formula, $X^{102}$ represents a fluorine atom or a hydrogen atom; and $R^{10}$ represents an alkyl group having 1 to 5 carbon atoms, an alkenyl group having 2 to 5 carbon atoms, or an alkoxy group having 1 to 4 carbon atoms.)

Although the number of compounds that can be combined with each other is not particularly limited, one or more of the plurality of compounds represented by the general formula (X-4) are preferably combined and one to three or more of the plurality of compounds are more preferably combined in consideration of solubility at low temperature, transition temperature, electrical reliability, double refractive index, and the like.

Furthermore, the compounds represented by the general formula (X-4) and used for the liquid crystal composition of the present invention are preferably compounds represented by general formula (X-4-1).

[Chem. 122]

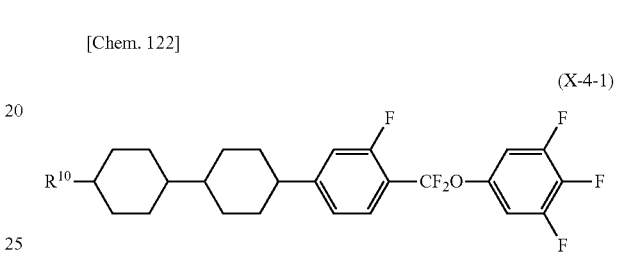

(In the formula, $R^{10}$ represents an alkyl group having 1 to 5 carbon atoms, an alkenyl group having 2 to 5 carbon atoms, or an alkoxy group having 1 to 4 carbon atoms.)

Although the number of compounds that can be combined with each other is not particularly limited, one or more of the plurality of compounds represented by the general formula (X-4-1) are preferably combined and one to three or more of the plurality of compounds are more preferably combined in consideration of solubility at low temperature, transition temperature, electrical reliability, double refractive index, and the like.

The content of the compounds represented by the general formula (X-4-1) is preferably 2 mass % or more and 20 mass % or less, more preferably 5 mass % or more and 17 mass % or less, more preferably 10 mass % or more and 15 mass % or less, and particularly preferably 10 mass % or more and 13 mass % or less relative to the total mass of the liquid crystal composition of the present invention in consideration of solubility at low temperature, transition temperature, electrical reliability, and the like.

More specifically, the compounds represented by the general formula (X-4-1) and used for the liquid crystal composition of the present invention are preferably compounds represented by formula (42.1) to formula (42.4) and more preferably a compound represented by formula (42.3).

[Chem. 123]

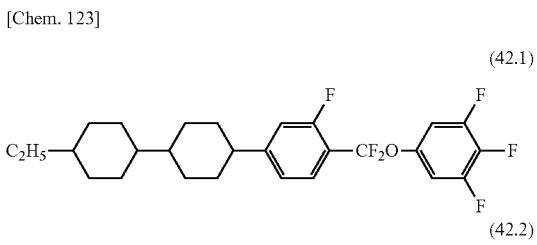

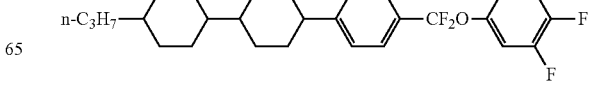

-continued (42.3)

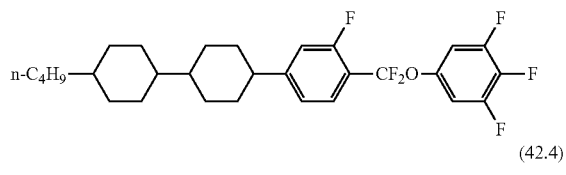

(42.4)

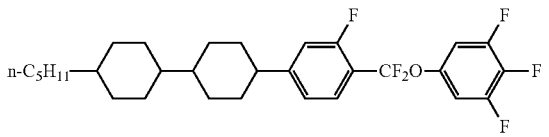

Furthermore, the compounds represented by the general formula (X) and used for the liquid crystal composition of the present invention are preferably compounds represented by general formula (X-4-2).

[Chem. 124]

(X-4-2)

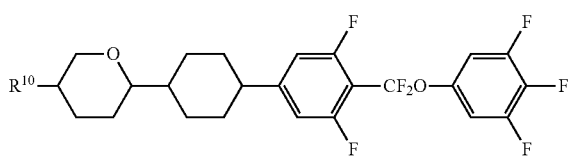

(In the formula, $R^{10}$ represents an alkyl group having 1 to 5 carbon atoms, an alkenyl group having 2 to 5 carbon atoms, or an alkoxy group having 1 to 4 carbon atoms.)

Although the number of compounds that can be combined with each other is not particularly limited, one or more of the plurality of compounds represented by the general formula (X-4-2) are preferably combined and one to three or more of the plurality of compounds are more preferably combined in consideration of solubility at low temperature, transition temperature, electrical reliability, double refractive index, and the like.

The content of the compounds represented by the general formula (X-4-2) is preferably 2 mass % or more and 20 mass % or less, more preferably 5 mass % or more and 17 mass % or less, more preferably 10 mass % or more and 15 mass % or less, and particularly preferably 10 mass % or more and 13 mass % or less relative to the total mass of the liquid crystal composition of the present invention in consideration of solubility at low temperature, transition temperature, electrical reliability, and the like.

More specifically, the compounds represented by the general formula (X-4-2) and used for the liquid crystal composition of the present invention are preferably compounds represented by formula (42.11) to formula (42.14) and more preferably a compound represented by formula (42.13) or a compound represented by formula (42.14).

[Chem. 125]

(42.11)

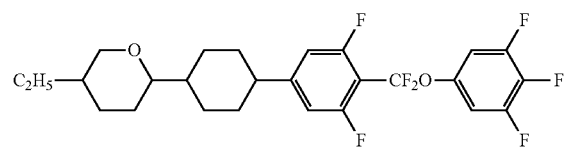

-continued (42.12)

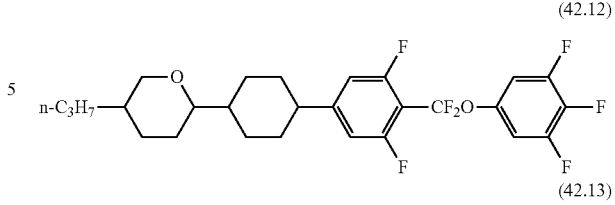

(42.13)

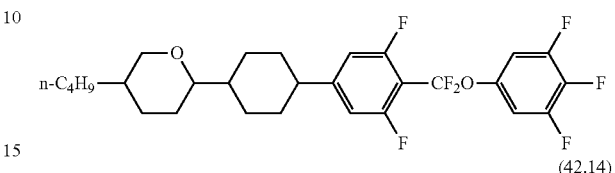

(42.14)

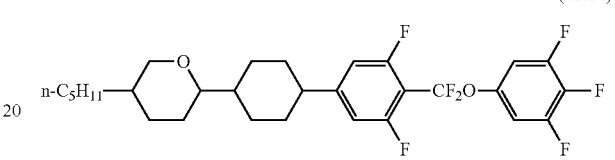

Furthermore, the compounds represented by the general formula (X) and used for the liquid crystal composition of the present invention are preferably compounds represented by general formula (X-4-3).

[Chem. 126]

(X-4-3)

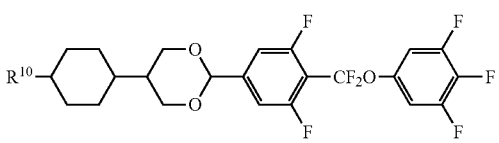

(In the formula, $R^{10}$ represents an alkyl group having 1 to 5 carbon atoms, an alkenyl group having 2 to 5 carbon atoms, or an alkoxy group having 1 to 4 carbon atoms.)

Although the number of compounds that can be combined with each other is not particularly limited, one or more of the plurality of compounds represented by the general formula (X-4-3) are preferably combined and one to three or more of the plurality of compounds are more preferably combined in consideration of solubility at low temperature, transition temperature, electrical reliability, double refractive index, and the like.

The content of the compounds represented by the general formula (X-4-3) is preferably 2 mass % or more and 20 mass % or less, more preferably 5 mass % or more and 17 mass % or less, more preferably 10 mass % or more and 15 mass % or less, and particularly preferably 10 mass % or more and 13 mass % or less relative to the total mass of the liquid crystal composition of the present invention in consideration of solubility at low temperature, transition temperature, electrical reliability, and the like.

More specifically, the compounds represented by the general formula (X-4-3) and used for the liquid crystal composition of the present invention are preferably compounds represented by formula (42.21) to formula (42.24) and more preferably a compound represented by formula (42.22).

[Chem. 127]

(42.21)
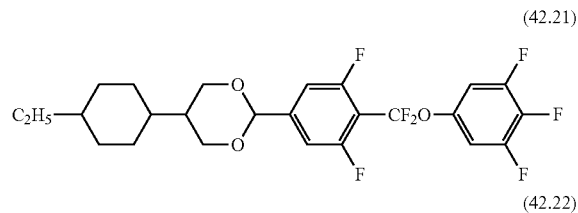
(42.22)

(42.23)
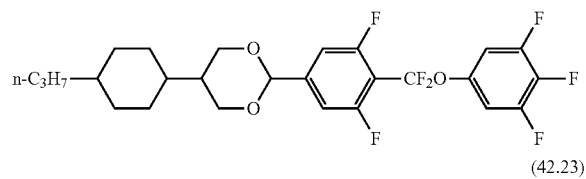

(42.24)
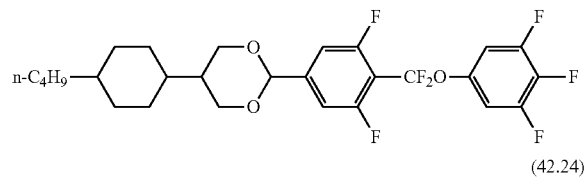

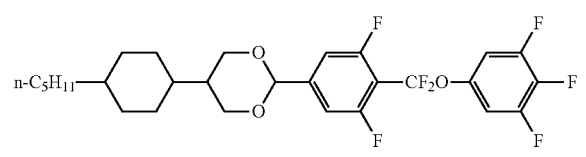

Furthermore, the compounds represented by the general formula (X) are preferably compounds represented by general formula (X-5).

[Chem. 128]

(X-5)
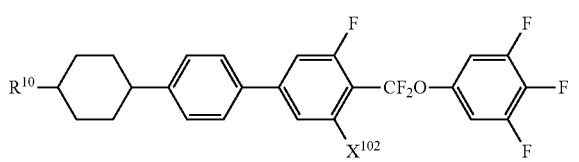

(In the formula, $X^{102}$ represents a fluorine atom or a hydrogen atom; and $R^{10}$ represents an alkyl group having 1 to 5 carbon atoms, an alkenyl group having 2 to 5 carbon atoms, or an alkoxy group having 1 to 4 carbon atoms.)

Although the number of compounds that can be combined with each other is not particularly limited, one or more of the plurality of compounds represented by the general formula (X-5) are preferably combined and one to three or more of the plurality of compounds are more preferably combined in consideration of solubility at low temperature, transition temperature, electrical reliability, double refractive index, and the like.

Furthermore, the compounds represented by the general formula (X-5) and used for the liquid crystal composition of the present invention are preferably compounds represented by general formula (X-5-1).

[Chem. 129]

(X-5-1)
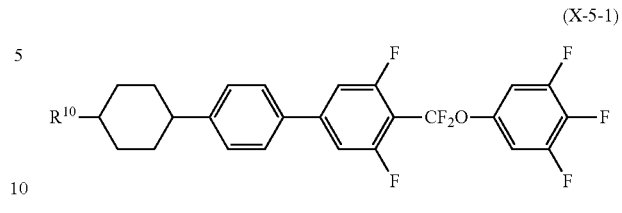

(In the formula, $R^{10}$ represents an alkyl group having 1 to 5 carbon atoms, an alkenyl group having 2 to 5 carbon atoms, or an alkoxy group having 1 to 4 carbon atoms.)

Although the number of compounds that can be combined with each other is not particularly limited, one or more of the plurality of compounds represented by the general formula (X-5-1) are preferably combined and one to three or more of the plurality of compounds are more preferably combined in consideration of solubility at low temperature, transition temperature, electrical reliability, double refractive index, and the like.

More specifically, the compounds represented by the general formula (X-5-1) and used for the liquid crystal composition of the present invention are preferably compounds represented by formula (43.1) to formula (43.4) and more preferably a compound represented by formula (43.2).

[Chem. 130]

(43.1)
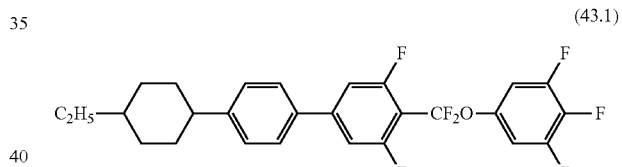

(43.2)
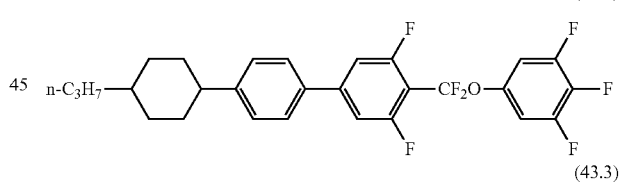

(43.3)
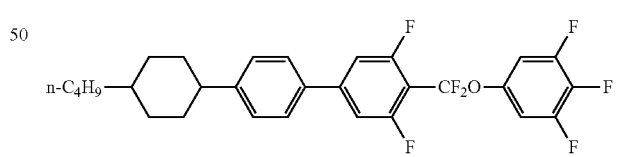

(43.4)
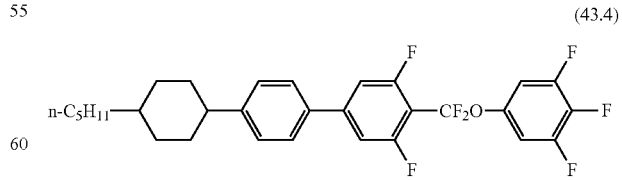

The liquid crystal composition of the present invention may also contain compounds represented by general formula (X'-7), which are similar to the compounds represented by the general formula (X).

[Chem. 131]

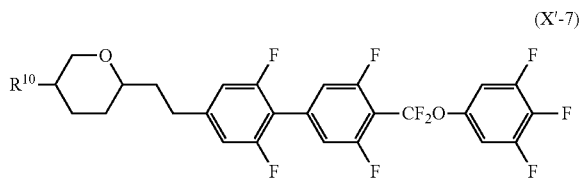

(X'-7)

(In the formula, $R^{10}$ represents an alkyl group having 1 to 5 carbon atoms, an alkenyl group having 2 to 5 carbon atoms, or an alkoxy group having 1 to 4 carbon atoms.)

Although the number of compounds that can be combined with each other is not particularly limited, one or more of the plurality of compounds represented by the general formula (X'-7) are preferably combined in consideration of solubility at low temperature, transition temperature, electrical reliability, double refractive index, and the like.

The content of the compounds represented by the general formula (X'-7) has an upper limit and a lower limit for each embodiment in consideration of characteristics such as solubility at low temperature, transition temperature, electrical reliability, and double refractive index.

For example, the content of the compounds is 4 to 30 mass % relative to the total mass of the liquid crystal composition of the present invention in one embodiment of the present invention, 5 to 30 mass % in another embodiment, 6 to 30 mass % in still another embodiment, 8 to 30 mass % in still yet another embodiment, 9 to 30 mass % in still yet another embodiment, 11 to 30 mass % in still yet another embodiment, 14 to 30 mass % in still yet another embodiment, and 18 to 30 mass % in still yet another embodiment.

Furthermore, for example, the content of the compounds is 4 to 30 mass % relative to the total mass in one embodiment of the present invention, 4 to 20 mass % in another embodiment, 4 to 13 mass % in still another embodiment, 4 to 10 mass % in still yet another embodiment, and 4 to 7 mass % in still yet another embodiment.

More specifically, the compounds represented by the general formula (X'-7) and used for the liquid crystal composition of the present invention are preferably compounds represented by formula (44.11) to formula (44.14) and more preferably a compound represented by formula (44.13).

[Chem. 132]

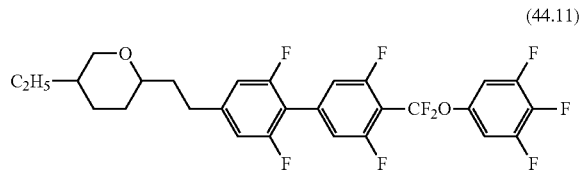

(44.11)

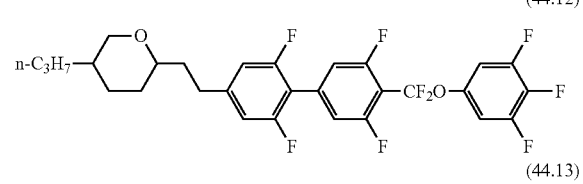

(44.12)

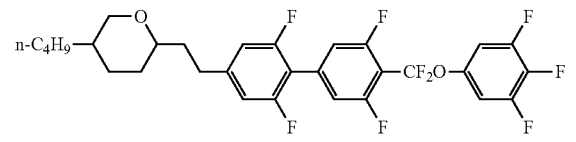

(44.13)

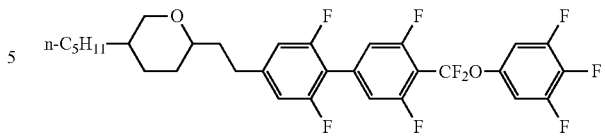

(44.14)

Furthermore, the compounds represented by the general formula (X) are preferably compounds selected from the group of compounds represented by general formula (XI).

[Chem. 133]

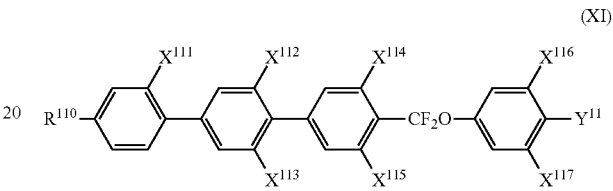

(XI)

(In the formula, $X^{111}$ to $X^{117}$ each independently represent a fluorine atom or a hydrogen atom, where at least one of $X^{111}$ to $X^{117}$ represents a fluorine atom; $R^{110}$ represents an alkyl group having 1 to 5 carbon atoms, an alkenyl group having 2 to 5 carbon atoms, or an alkoxy group having 1 to 4 carbon atoms; and $Y^{11}$ represents a fluorine atom or $-OCF_3$.)

Although the number of compounds that can be combined with each other is not particularly limited, one to three or more of the plurality of compounds represented by the general formula (XI) are preferably combined in consideration of solubility at low temperature, transition temperature, electrical reliability, double refractive index, and the like.

The content of the compounds represented by the general formula (XI) has an upper limit and a lower limit for each embodiment in consideration of characteristics such as solubility at low temperature, transition temperature, electrical reliability, and double refractive index. For example, the content of the compounds is 2 to 30 mass % relative to the total mass of the liquid crystal composition of the present invention in one embodiment of the present invention, 4 to 30 mass % in another embodiment, 5 to 30 mass % in still another embodiment, 7 to 30 mass % in still yet another embodiment, 9 to 30 mass % in still yet another embodiment, 10 to 30 mass % in still yet another embodiment, 12 to 30 mass % in still yet another embodiment, 13 to 30 mass % in still yet another embodiment, 15 to 30 mass % in still yet another embodiment, and 18 to 30 mass % in still yet another embodiment.

Furthermore, for example, the content of the compounds is 2 to 30 mass % relative to the total mass in one embodiment of the present invention, 2 to 25 mass % in another embodiment, 2 to 20 mass % in still another embodiment, 2 to 15 mass % in still yet another embodiment, 2 to 10 mass % in still yet another embodiment, and 2 to 5 mass % in still yet another embodiment.

When the liquid crystal composition of the present invention is used for liquid crystal display devices having a small cell gap, it is suitable to increase the content of the compounds represented by the general formula (XI). When the liquid crystal composition of the present invention is used for liquid crystal display devices having a low drive voltage, it is suitable to increase the content of the compounds represented by the general formula (XI). When the liquid crystal composition of the present invention is used for liquid crystal display devices which are operated in a low-temperature environment, it is suitable to decrease the content of the compounds represented by the general formula (XI). When the liquid crystal composition of the present invention is used for liquid crystal display devices having a high response speed, it is suitable to decrease the content of the compounds represented by the general formula (XI).

Furthermore, the compounds represented by the general formula (XI) and used for the liquid crystal composition of the present invention are preferably compounds represented by general formula (XI-1).

[Chem. 134]

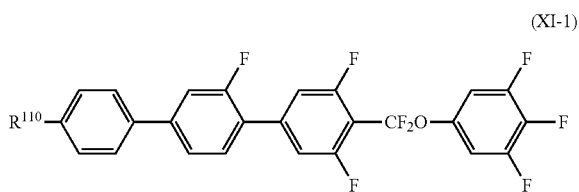

(XI-1)

(In the formula, $R^{110}$ represents an alkyl group having 1 to 5 carbon atoms, an alkenyl group having 2 to 5 carbon atoms, or an alkoxy group having 1 to 4 carbon atoms.)

Although the number of compounds that can be combined with each other is not particularly limited, the plurality of compounds represented by the general formula (XI-1) can be suitably combined for each embodiment in consideration of solubility at low temperature, transition temperature, electrical reliability, double refractive index, and the like. For example, the number of the compounds is one in one embodiment of the present invention. The number of the compounds is two in another embodiment. The number of the compounds is three or more in still another embodiment.

The content of the compounds represented by the general formula (XI-1) is preferably 1 mass % or more and 20 mass % or less, more preferably 3 mass % or more and 20 mass % or less, more preferably 4 mass % or more and 20 mass % or less, more preferably 6 mass % or more and 15 mass % or less, and particularly preferably 9 mass % or more and 12 mass % or less relative to the total mass of the liquid crystal composition of the present invention in consideration of solubility at low temperature, transition temperature, electrical reliability, and the like.

More specifically, the compounds represented by the general formula (XI-1) and used for the liquid crystal composition of the present invention are preferably compounds represented by formula (45.1) to formula (45.4), more preferably compounds represented by formula (45.2) to formula (45.4), and more preferably a compound represented by formula (45.2).

[Chem. 135]

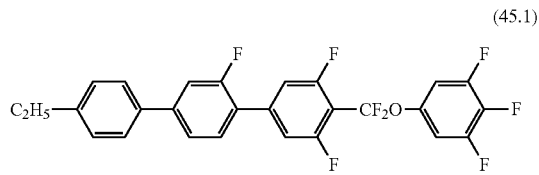

(45.1)

-continued

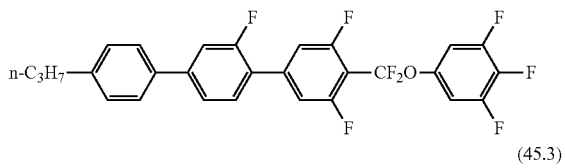

(45.2)

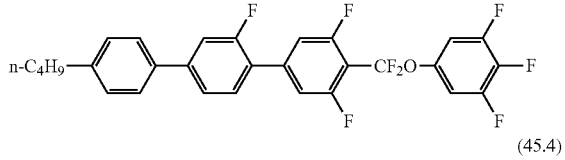

(45.3)

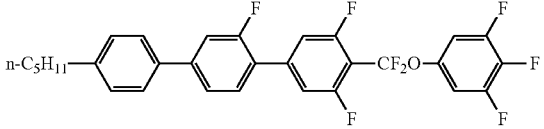

(45.4)

In the liquid crystal composition of the present invention, the content of the compound represented by the formula (45.2) is preferably 1 mass % or more and 25 mass % or less, more preferably 2 mass % or more and 15 mass % or less, and more preferably 3 mass % or more and 10 mass % or less relative to the total mass of the liquid crystal composition of the present invention in consideration of solubility at low temperature, transition temperature, electrical reliability, and the like.

Examples of the content in the more preferable range include 3 mass % or more and 7 mass % or less, 3 mass % or more and 6 mass % or less, 3 mass % or more and 5 mass % or less, 3 mass % or more and 4 mass % or less, 4 mass % or more and 10 mass % or less, 5 mass % or more and 10 mass % or less, 6 mass % or more and 10 mass % or less, 7 mass % or more and 10 mass % or less, and 8 mass % or more and 10 mass % or less.

In the liquid crystal composition of the present invention, the content of the compound represented by the formula (45.3) is preferably 1 mass % or more and 25 mass % or less, more preferably 2 mass % or more and 20 mass % or less, and more preferably 3 mass % or more and 15 mass % or less relative to the total mass of the liquid crystal composition of the present invention in consideration of solubility at low temperature, transition temperature, electrical reliability, and the like.

In the liquid crystal composition of the present invention, the content of the compound represented by the formula (45.4) is preferably 1 mass % or more and 25 mass % or less, more preferably 2 mass % or more and 20 mass % or less, and more preferably 3 mass % or more and 15 mass % or less relative to the total mass of the liquid crystal composition of the present invention in consideration of solubility at low temperature, transition temperature, electrical reliability, and the like.

Furthermore, the compounds represented by the general formula (XI) and used for the liquid crystal composition of the present invention are preferably compounds represented by general formula (XI-2).

[Chem. 136]

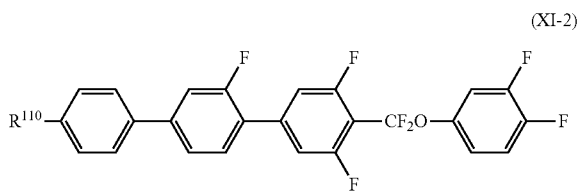

(XI-2)

(In the formula, $R^{110}$ represents an alkyl group having 1 to 5 carbon atoms, an alkenyl group having 2 to 5 carbon atoms, or an alkoxy group having 1 to 4 carbon atoms.)

Although the number of compounds that can be combined with each other is not particularly limited, a plurality of the compounds represented by the general formula (XI-2) can be suitably combined for each embodiment in consideration of solubility at low temperature, transition temperature, electrical reliability, double refractive index, and the like. For example, the number of the compounds is one in one embodiment of the present invention. The number of the compounds is two in another embodiment. The number of the compounds is three or more in still another embodiment.

The content of the compounds represented by the general formula (XI-2) is preferably 1 mass % or more and 20 mass % or less, more preferably 3 mass % or more and 20 mass % or less, more preferably 4 mass % or more and 20 mass % or less, more preferably 6 mass % or more and 15 mass % or less, and particularly preferably 9 mass % or more and 12 mass % or less relative to the total mass of the liquid crystal composition of the present invention in consideration of solubility at low temperature, transition temperature, electrical reliability, and the like.

More specifically, the compounds represented by the general formula (XI-2) and used for the liquid crystal composition of the present invention are preferably compounds represented by formula (45.11) to formula (45.14), more preferably compounds represented by formula (45.12) to formula (45.14), and more preferably a compound represented by formula (45.12).

[Chem. 137]

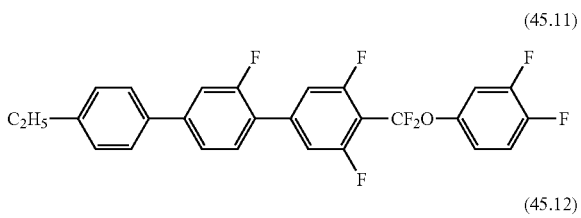

(45.11)

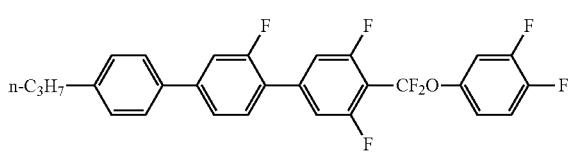

(45.12)

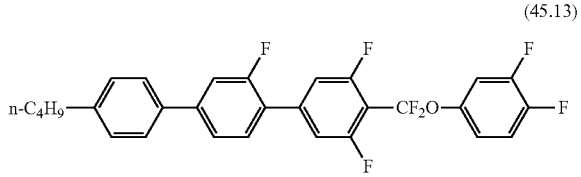

(45.13)

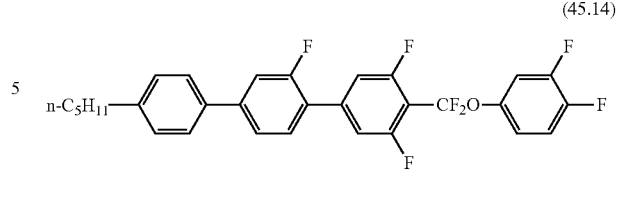

(45.14)

Furthermore, the compounds represented by the general formula (X) are preferably compounds selected from the group of compounds represented by general formula (XII).

[Chem. 138]

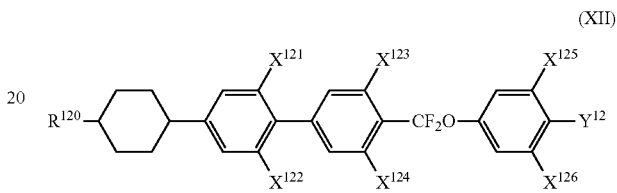

(XII)

(In the formula, $X^{121}$ to $X^{126}$ each independently represent a fluorine atom or a hydrogen atom; $R^{120}$ represents an alkyl group having 1 to 5 carbon atoms, an alkenyl group having 2 to 5 carbon atoms, or an alkoxy group having 1 to 4 carbon atoms; and $Y^{12}$ represents a fluorine atom or —$OCF_3$.)

Although the number of compounds that can be combined with each other is not particularly limited, one to three or more of the plurality of compounds represented by the general formula (XII) are preferably combined and one to four or more of the plurality of compounds are more preferably combined in consideration of solubility at low temperature, transition temperature, electrical reliability, double refractive index, and the like.

Furthermore, the compounds represented by the general formula (XII) and used for the liquid crystal composition of the present invention are preferably compounds represented by general formula (XII-1).

[Chem. 139]

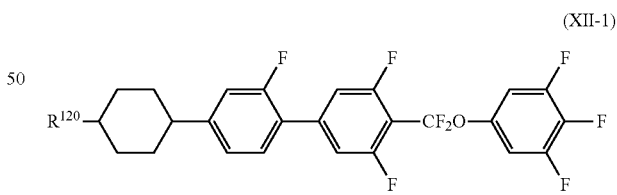

(XII-1)

(In the formula, $R^{120}$ represents an alkyl group having 1 to 5 carbon atoms, an alkenyl group having 2 to 5 carbon atoms, or an alkoxy group having 1 to 4 carbon atoms.)

Although the number of compounds that can be combined with each other is not particularly limited, one or more of the plurality of compounds represented by the general formula (XII-1) are preferably combined and one to three or more of the plurality of compounds are more preferably combined in consideration of solubility at low temperature, transition temperature, electrical reliability, double refractive index, and the like.

The content of the compounds represented by the general formula (XII-1) is preferably 1 mass % or more and 15 mass % or less, more preferably 2 mass % or more and 10 mass % or less, more preferably 3 mass % or more and 8 mass % or less, and particularly preferably 4 mass % or more and 6 mass % or less relative to the total mass of the liquid crystal composition of the present invention in consideration of solubility at low temperature, transition temperature, electrical reliability, and the like.

More specifically, the compounds represented by the general formula (XII-1) and used for the liquid crystal composition of the present invention are preferably compounds represented by formula (46.1) to formula (46.4) and more preferably compounds represented by formula (46.2) to formula (46.4).

[Chem. 140]

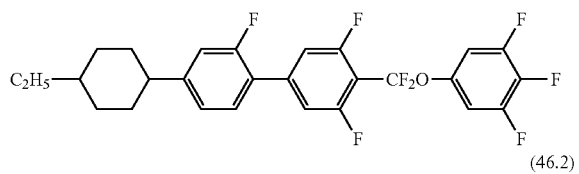
(46.1)

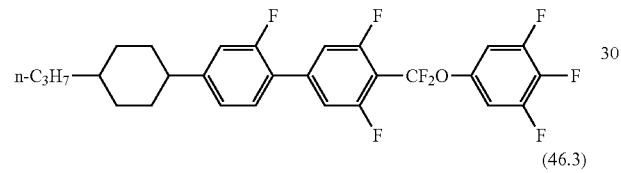
(46.2)

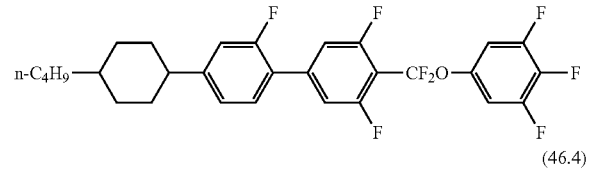
(46.3)

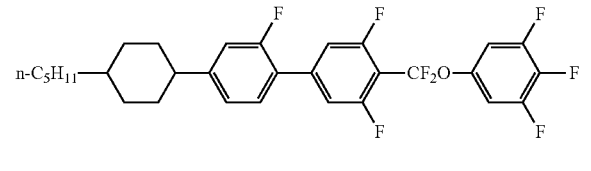
(46.4)

Furthermore, the compounds represented by the general formula (XII) are preferably compounds represented by general formula (XII-2).

[Chem. 141]

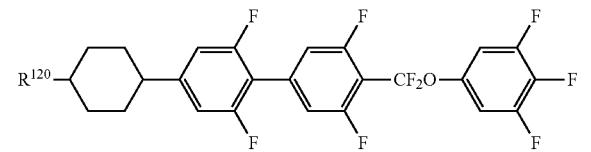
(XII-2)

(In the formula, $R^{120}$ represents an alkyl group having 1 to 5 carbon atoms, an alkenyl group having 2 to 5 carbon atoms, or an alkoxy group having 1 to 4 carbon atoms.)

Although the number of compounds that can be combined with each other is not particularly limited, one or more of the plurality of compounds represented by the general formula (XII-2) are preferably combined and one to three or more of the plurality of compounds are more preferably combined in consideration of solubility at low temperature, transition temperature, electrical reliability, double refractive index, and the like.

The content of the compounds represented by the general formula (XII-2) is preferably 1 mass % or more and 20 mass % or less, more preferably 3 mass % or more and 20 mass % or less, more preferably 4 mass % or more and 17 mass % or less, more preferable 6 mass % or more and 15 mass % or less, and particularly preferably 9 mass % or more and 13 mass % or less relative to the total mass of the liquid crystal composition of the present invention in consideration of solubility at low temperature, transition temperature, electrical reliability, and the like.

More specifically, the compounds represented by the general formula (XII-2) and used for the liquid crystal composition of the present invention are preferably compounds represented by formula (47.1) to formula (47.4) and more preferably compounds represented by formula (47.2) to formula (47.4).

[Chem. 142]

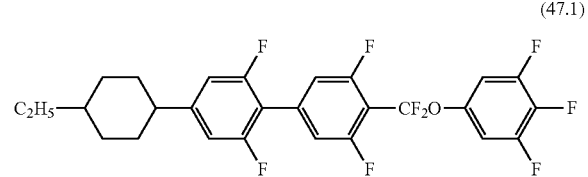
(47.1)

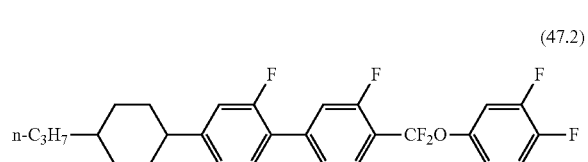
(47.2)

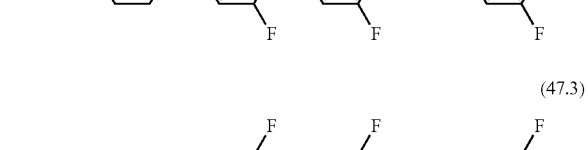
(47.3)

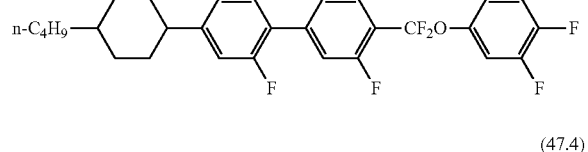
(47.4)

Furthermore, the compounds represented by the general formula (M) are preferably compounds selected from the group of compounds represented by general formula (XIII).

[Chem. 143]

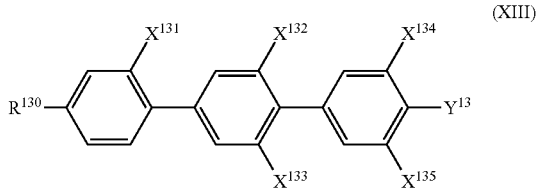

(XIII)

(In the formula, $X^{131}$ to $X^{135}$ each independently represent a fluorine atom or a hydrogen atom; $R^{130}$ represents an alkyl group having 1 to 5 carbon atoms, an alkenyl group having 2 to 5 carbon atoms, or an alkoxy group having 1 to 4 carbon atoms; and $Y^{13}$ represents a fluorine atom or —OCF$_3$.)

Although the number of compounds that can be combined with each other is not particularly limited, one or two of the plurality of compounds represented by the general formula (XIII) are preferably contained, one to three of the compounds are more preferably contained, and one to four of the compounds are more preferably contained.

The content of the compounds represented by the general formula (XIII) has an upper limit and a lower limit for each embodiment in consideration of characteristics such as solubility at low temperature, transition temperature, electrical reliability, and double refractive index.

For example, the content of the compounds is 2 to 30 mass % relative to the total mass of the liquid crystal composition of the present invention in one embodiment of the present invention, 4 to 30 mass % in another embodiment, 5 to 30 mass % in still another embodiment, 7 to 30 mass % in still yet another embodiment, 9 to 30 mass % in still yet another embodiment, 11 to 30 mass % in still yet another embodiment, 13 to 30 mass % in still yet another embodiment, 14 to 30 mass % in still yet another embodiment, 16 to 30 mass % in still yet another embodiment, and 20 to 30 mass % in still yet another embodiment.

Furthermore, for example, the content of the compounds is 2 to 30 mass % relative to the total mass in one embodiment of the present invention, 2 to 25 mass % in another embodiment, 2 to 20 mass % in still another embodiment, 2 to 15 mass % in still yet another embodiment, 2 to 10 mass % in still yet another embodiment, and 2 to 5 mass % in still yet another embodiment.

When the liquid crystal composition of the present invention is used for liquid crystal display devices having a small cell gap, it is suitable to increase the content of the compounds represented by the general formula (XIII). When the liquid crystal composition of the present invention is used for liquid crystal display devices having a low drive voltage, it is suitable to increase the content of the compounds represented by the general formula (XIII). When the liquid crystal composition of the present invention is used for liquid crystal display devices which are operated in a low-temperature environment, it is suitable to decrease the content of the compounds represented by the general formula (XIII). When the liquid crystal composition of the present invention is used for liquid crystal display devices having a high response speed, it is suitable to decrease the content of the compounds represented by the general formula (XIII).

Furthermore, the compounds represented by the general formula (XIII) are preferably compounds represented by general formula (XIII-1).

[Chem. 144]

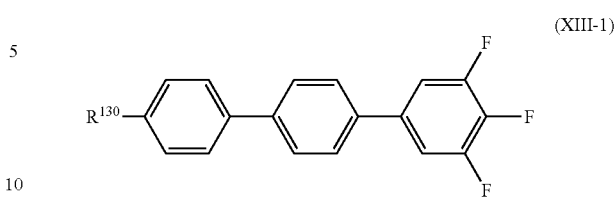

(XIII-1)

(In the formula, $R^{130}$ represents an alkyl group having 1 to 5 carbon atoms, an alkenyl group having 2 to 5 carbon atoms, or an alkoxy group having 1 to 4 carbon atoms.)

The content of the compounds represented by the general formula (XIII-1) is preferably 1 mass % or more and 25 mass % or less, more preferably 3 mass % or more and 25 mass % or less, more preferably 5 mass % or more and 20 mass % or less, and particularly preferably 10 mass % or more and 15 mass % or less relative to the total mass of the liquid crystal composition of the present invention.

Furthermore, the compounds represented by the general formula (XIII-1) are preferably compounds represented by formula (48.1) to formula (48.4) and more preferably a compound represented by formula (48.2).

[Chem. 145]

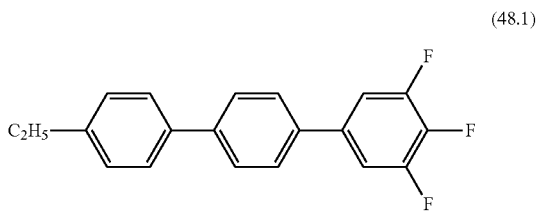

(48.1)

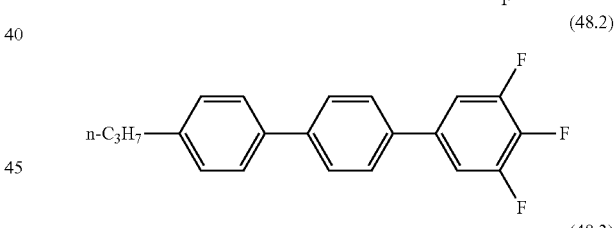

(48.2)

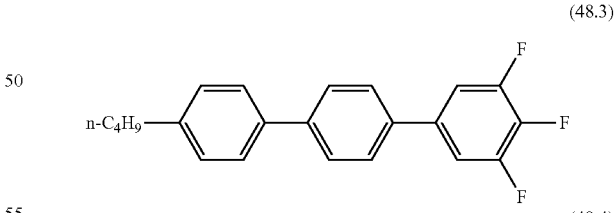

(48.3)

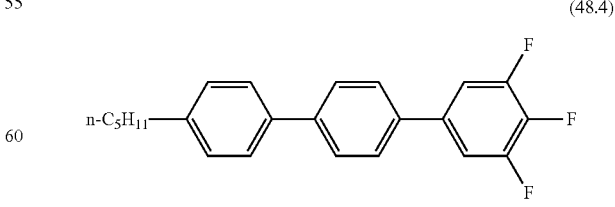

(48.4)

Furthermore, the compounds represented by the general formula (XIII) are preferably compounds represented by general formula (XIII-2).

[Chem. 146]

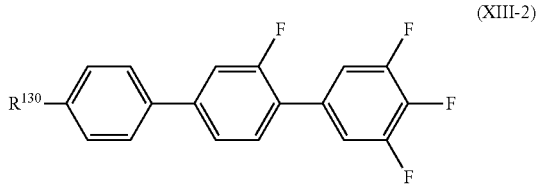

(XIII-2)

(In the formula, $R^{130}$ represents an alkyl group having 1 to 5 carbon atoms, an alkenyl group having 2 to 5 carbon atoms, or an alkoxy group having 1 to 4 carbon atoms.)

Although the number of compounds that can be combined with each other is not particularly limited, one or more of the plurality of compounds represented by the general formula (XIII-2) are preferably contained.

The content of the compounds represented by the general formula (XIII-2) is preferably 5 mass % or more and 25 mass % or less, more preferably 6 mass % or more and 25 mass % or less, more preferably 8 mass % or more and 20 mass % or less, and particularly preferably 10 mass % or more and 15 mass % or less relative to the total mass of the liquid crystal composition of the present invention.

Furthermore, the compounds represented by the general formula (XIII-2) are preferably compounds represented by formula (49.1) to formula (49.4) and more preferably a compound represented by formula (49.1) or formula (49.2).

[Chem. 147]

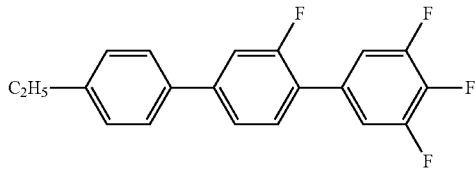

(49.1)

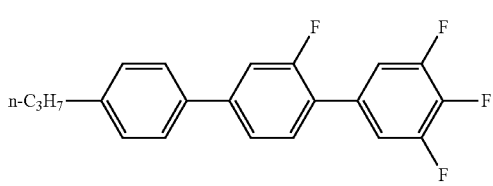

(49.2)

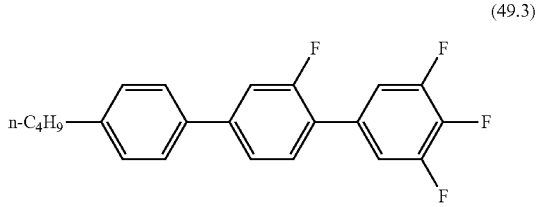

(49.3)

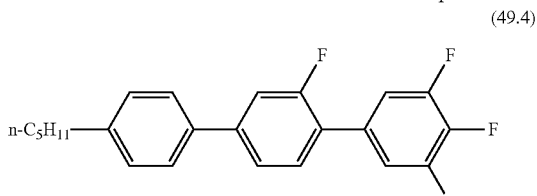

(49.4)

Furthermore, the compounds represented by the general formula (XIII) are preferably compounds represented by general formula (XIII-3).

[Chem. 148]

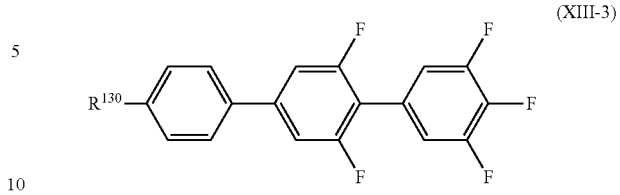

(XIII-3)

(In the formula, $R^{130}$ represents an alkyl group having 1 to 5 carbon atoms, an alkenyl group having 2 to 5 carbon atoms, or an alkoxy group having 1 to 4 carbon atoms.)

Although the number of compounds that can be combined with each other is not particularly limited, one or two of the plurality of compounds represented by the general formula (XIII-3) are preferably contained.

The content of the compounds represented by the general formula (XIII-3) is preferably 2 mass % or more and 20 mass % or less, more preferably 4 mass % or more and 20 mass % or less, more preferably 9 mass % or more and 17 mass % or less, and particularly preferably 11 mass % or more and 14 mass % or less relative to the total mass of the liquid crystal composition of the present invention.

Furthermore, the compounds represented by the general formula (XIII-3) are preferably compounds represented by formula (50.1) to formula (50.4) and more preferably a compound represented by formula (50.1) or formula (50.2).

[Chem. 149]

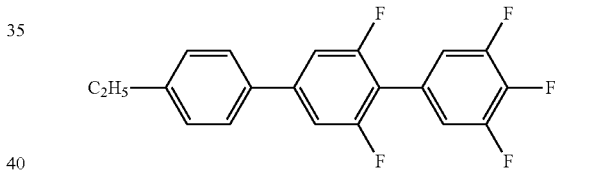

(50.1)

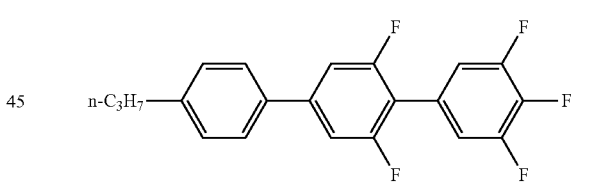

(50.2)

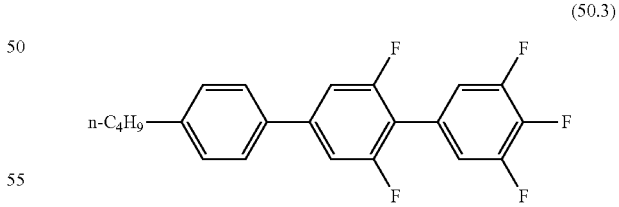

(50.3)

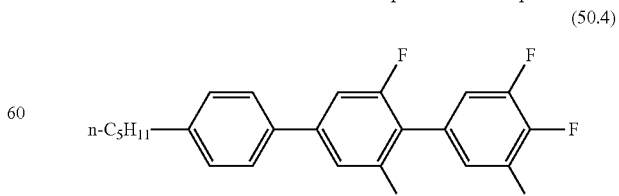

(50.4)

Furthermore, the compounds represented by the general formula (M) are preferably compounds selected from the group of compounds represented by general formula (XIV).

[Chem. 150]

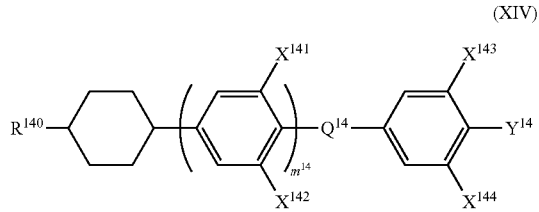

(In the formula, $R^{140}$ represents an alkyl group having 1 to 7 carbon atoms, an alkenyl group having 2 to 7 carbon atoms, or an alkoxy group having 1 to 7 carbon atoms; $X^{141}$ to $X^{144}$ each independently represent a fluorine atom or a hydrogen atom; $Y^{14}$ represents a fluorine atom, a chlorine atom, or —$OCF_3$; $Q^{14}$ represents a single bond, —COO—, or —$CF_2O$—; and $m^{14}$ represents 0 or 1.)

Although the number of compounds that can be combined with each other is not particularly limited, a plurality of the compounds represented by the general formula (XIV) can be suitably combined for each embodiment in consideration of solubility at low temperature, transition temperature, electrical reliability, double refractive index, and the like. For example, the number of the compounds is one in one embodiment of the present invention. The number of the compounds is two in another embodiment of the present invention. The number of the compounds is three in still another embodiment of the present invention. The number of the compounds is four in still yet another embodiment of the present invention. The number of the compounds is five in still yet another embodiment of the present invention. The number of the compounds is six or more in still yet another embodiment of the present invention.

The content of the compounds represented by the general formula (XIV) has an upper limit and a lower limit for each embodiment in consideration of characteristics such as solubility at low temperature, transition temperature, electrical reliability, and double refractive index.

For example, the content of the compounds is 3 to 40 mass % relative to the total mass of the liquid crystal composition of the present invention in one embodiment of the present invention, 7 to 40 mass % in another embodiment, 8 to 40 mass % in still another embodiment, 11 to 40 mass % in still yet another embodiment, 12 to 40 mass % in still yet another embodiment, 16 to 40 mass % in still yet another embodiment, 18 to 40 mass % in still yet another embodiment, 19 to 40 mass % in still yet another embodiment, 22 to 40 mass % in still yet another embodiment, and 25 to 40 mass % in still yet another embodiment.

Furthermore, for example, the content of the compounds is 3 to 40 mass % relative to the total mass in one embodiment of the present invention, 3 to 35 mass % in another embodiment, 3 to 30 mass % in still another embodiment, 3 to 25 mass % in still yet another embodiment, 3 to 20 mass % in still yet another embodiment, and 3 to 15 mass % in still yet another embodiment.

When the liquid crystal composition of the present invention is used for liquid crystal display devices having a low drive voltage, it is suitable to increase the content of the compounds represented by the general formula (XIV). When the liquid crystal composition of the present invention is used for liquid crystal display devices having a high response speed, it is suitable to decrease the content of the compounds represented by the general formula (XIV).

Furthermore, the compounds represented by the general formula (XIV) are preferably compounds represented by general formula (XIV-1).

[Chem. 151]

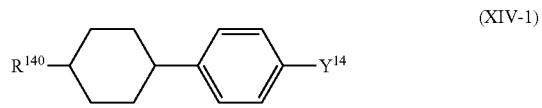

(In the formula, $R^{140}$ represents an alkyl group having 1 to 7 carbon atoms, an alkenyl group having 2 to 7 carbon atoms, or an alkoxy group having 1 to 7 carbon atoms; and $Y^{14}$ represents a fluorine atom, a chlorine atom, or —$OCF_3$.)

Although the number of compounds that can be combined with each other is not particularly limited, one to three of the plurality of compounds represented by the general formula (XIV-1) are preferably combined in consideration of solubility at low temperature, transition temperature, electrical reliability, double refractive index, and the like.

Furthermore, the compounds represented by the general formula (XIV-1) are preferably compounds represented by general formula (XIV-1-1).

[Chem. 152]

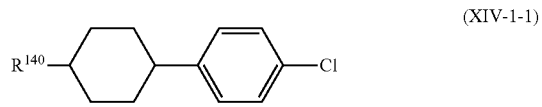

(In the formula, $R^{140}$ represents an alkyl group having 1 to 7 carbon atoms, an alkenyl group having 2 to 7 carbon atoms, or an alkoxy group having 1 to 7 carbon atoms.)

The content of the compounds represented by the general formula (XIV-1) is preferably 2 mass % or more, more preferably 4 mass % or more, more preferably 7 mass % or more, more preferably 10 mass % or more, and particularly preferably 18 mass % or more relative to the total mass of the liquid crystal composition of the present invention. The maximum content is preferably 30 mass % or less, more preferably 27 mass % or less, more preferably 24 mass % or less, and particularly preferably less than 21 mass % in consideration of solubility at low temperature, transition temperature, electrical reliability, and the like.

More specifically, the compounds represented by the general formula (XIV-1-1) are preferably compounds represented by formula (51.1) to formula (51.4) and more preferably a compound represented by formula (51.1).

[Chem. 153]

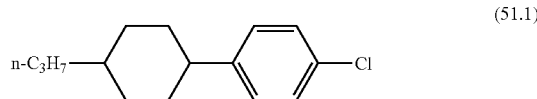

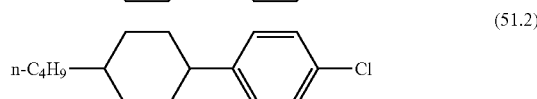

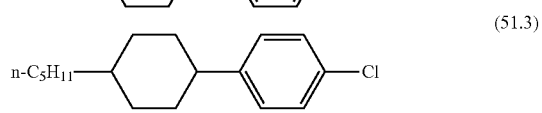

-continued

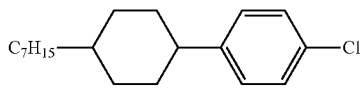
(51.4)

Furthermore, the compounds represented by the general formula (XIV-1) are preferably compounds represented by general formula (XIV-1-2).

[Chem. 154]

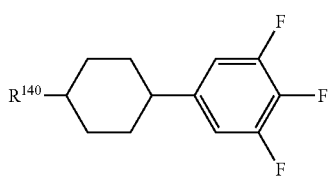
(XIV-1-2)

(In the formula, $R^{140}$ represents an alkyl group having 1 to 7 carbon atoms, an alkenyl group having 2 to 7 carbon atoms, or an alkoxy group having 1 to 7 carbon atoms.)

The content of the compounds represented by the general formula (XIV-1-2) is preferably 1 mass % or more and 15 mass % or less, more preferably 3 mass % or more and 13 mass % or less, more preferably 5 mass % or more and 11 mass % or less, and particularly preferably 7 mass % or more and 9 mass % or less relative to the total mass of the liquid crystal composition of the present invention in consideration of solubility at low temperature, transition temperature, electrical reliability, and the like.

More specifically, the compounds represented by the general formula (XIV-1-2) are preferably compounds represented by formula (52.1) to formula (52.4) and more preferably a compound represented by formula (52.4).

[Chem. 155]

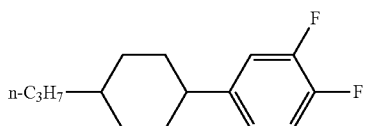
(52.1)

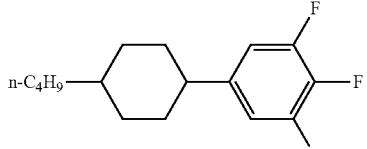
(52.2)

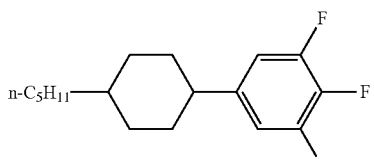
(52.3)

-continued

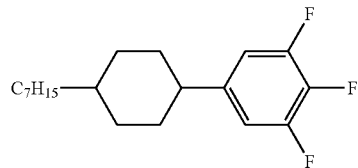
(52.4)

Furthermore, the compounds represented by the general formula (XIV) are preferably compounds represented by general formula (XIV-2).

[Chem. 156]

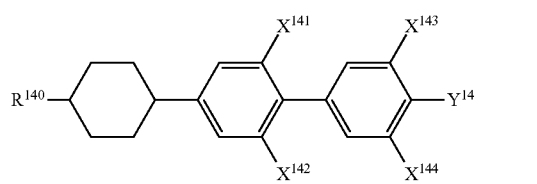
(XIV-2)

(In the formula, $R^{140}$ represents an alkyl group having 1 to 5 carbon atoms, an alkenyl group having 2 to 5 carbon atoms, or an alkoxy group having 1 to 4 carbon atoms; $X^{141}$ to $X^{144}$ each independently represent a fluorine atom or a hydrogen atom; and $Y^{14}$ represents a fluorine atom, a chlorine atom, or —$OCF_3$.)

Although the number of compounds that can be combined with each other is not particularly limited, a plurality of the compounds represented by the general formula (XIV-2) can be suitably combined for each embodiment in consideration of solubility at low temperature, transition temperature, electrical reliability, double refractive index, and the like. For example, the number of the compounds is one in one embodiment of the present invention. The number of the compounds is two in another embodiment of the present invention. The number of the compounds is three in still another embodiment of the present invention. The number of the compounds is four in still yet another embodiment of the present invention. The number of the compounds is five or more in still yet another embodiment of the present invention.

The content of the compounds represented by the general formula (XIV-2) has an upper limit and a lower limit for each embodiment in consideration of characteristics such as solubility at low temperature, transition temperature, electrical reliability, and double refractive index.

For example, the content of the compounds is 3 to 40 mass % relative to the total mass of the liquid crystal composition of the present invention in one embodiment of the present invention, 7 to 40 mass % in another embodiment, 8 to 40 mass % in still another embodiment, 10 to 40 mass % in still yet another embodiment, 11 to 40 mass % in still yet another embodiment, 12 to 40 mass % in still yet another embodiment, 18 to 40 mass % in still yet another embodiment, 19 to 40 mass % in still yet another embodiment, 21 to 40 mass % in still yet another embodiment, and 22 to 40 mass % in still yet another embodiment.

Furthermore, for example, the content of the compounds is 3 to 40 mass % relative to the total mass in one embodiment of the present invention, 3 to 35 mass % in another embodiment, 3 to 25 mass % in still another embodiment, 3 to 20 mass % in still yet another embodiment, 3 to 15 mass % in still yet another embodiment, and 3 to 10 mass % in still yet another embodiment.

When the liquid crystal composition of the present invention is used for liquid crystal display devices having a low drive voltage, it is suitable to increase the content of the compounds represented by the general formula (XIV-2). When the liquid crystal composition of the present invention is used for liquid crystal display devices having a high response speed, it is suitable to decrease the content of the compounds represented by the general formula (XIV-2).

Furthermore, the compounds represented by the general formula (XIV-2) are preferably compounds represented by general formula (XIV-2-1).

[Chem. 157]

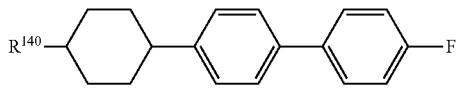

(XIV-2-1)

(In the formula, $R^{140}$ represents an alkyl group having 1 to 5 carbon atoms, an alkenyl group having 2 to 5 carbon atoms, or an alkoxy group having 1 to 4 carbon atoms.)

The content of the compounds represented by the general formula (XIV-2-1) is preferably 1 mass % or more and 15 mass % or less, more preferably 3 mass % or more and 13 mass % or less, more preferably 5 mass % or more and 11 mass % or less, and particularly preferably 7 mass % or more and 9 mass % or less relative to the total mass of the liquid crystal composition of the present invention in consideration of solubility at low temperature, transition temperature, electrical reliability, and the like.

More specifically, the compounds represented by the general formula (XIV-2-1) are preferably compounds represented by formula (53.1) to formula (53.4) and more preferably a compound represented by formula (53.4).

[Chem. 158]

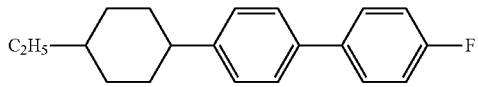

(53.1)

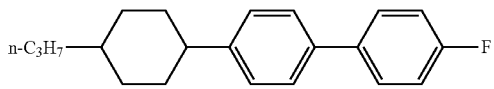

(53.2)

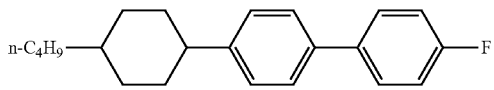

(53.3)

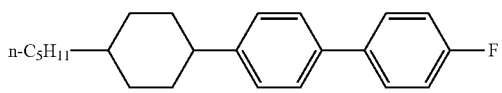

(53.4)

Furthermore, the compounds represented by the general formula (XIV-2) are preferably compounds represented by general formula (XIV-2-2).

[Chem. 159]

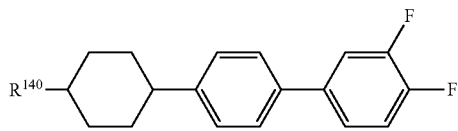

(XIV-2-2)

(In the formula, $R^{140}$ represents an alkyl group having 1 to 5 carbon atoms, an alkenyl group having 2 to 5 carbon atoms, or an alkoxy group having 1 to 4 carbon atoms.)

The content of the compounds represented by the general formula (XIV-2-2) is preferably 3 mass % or more and 20 mass % or less, more preferably 6 mass % or more and 17 mass % or less, more preferably 9 mass % or more and 15 mass % or less, and particularly preferably 12 mass % or more and 14 mass % or less relative to the total mass of the liquid crystal composition of the present invention in consideration of solubility at low temperature, transition temperature, electrical reliability, and the like.

More specifically, the compounds represented by the general formula (XIV-2-2) are preferably compounds represented by formula (54.1) to formula (54.4) and more preferably a compound represented by formula (54.2) and/or a compound represented by formula (54.4).

[Chem. 160]

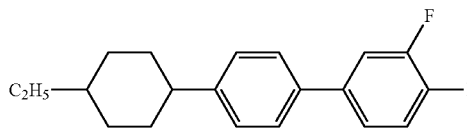

(54.1)

(54.2)

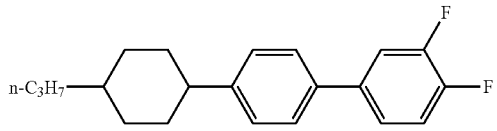

(54.3)

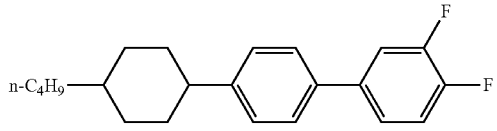

(54.4)

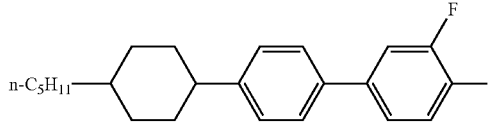

In the liquid crystal composition of the present invention, the content of the compound represented by formula (54.2) is preferably 5 mass % or more and 35 mass % or less, more preferably 5 mass % and 25 mass % or less, and more preferably 5 mass % or more and 20 mass % or less relative to the total mass of the liquid crystal composition of the present invention.

Furthermore, the compounds represented by the general formula (XIV-2) are preferably compounds represented by general formula (XIV-2-3).

[Chem. 161]

(XIV-2-3)

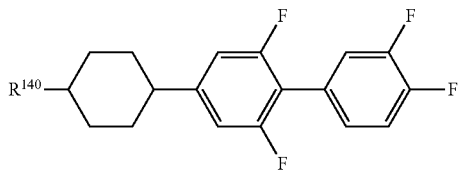

(In the formula, $R^{140}$ represents an alkyl group having 1 to 5 carbon atoms, an alkenyl group having 2 to 5 carbon atoms, or an alkoxy group having 1 to 4 carbon atoms.)

The content of the compounds represented by the general formula (XIV-2-3) is preferably 5 mass % or more and 30 mass % or less, more preferably 9 mass % or more and 27 mass % or less, more preferably 12 mass % or more and 24 mass % or less, and particularly preferably 12 mass % or more and 20 mass % or less relative to the total mass of the liquid crystal composition of the present invention in consideration of solubility at low temperature, transition temperature, electrical reliability, and the like.

More specifically, the compounds represented by the general formula (XIV-2-3) are preferably compounds represented by formula (55.1) to formula (55.4) and more preferably a compound represented by formula (55.2) and/or a compound represented by formula (55.4).

[Chem. 162]

(55.1)

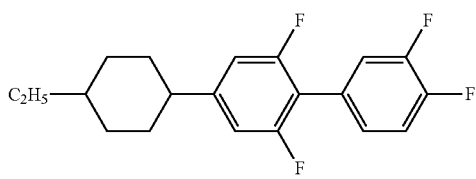

(55.2)

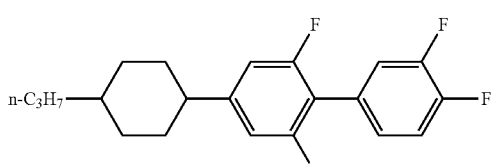

(55.3)

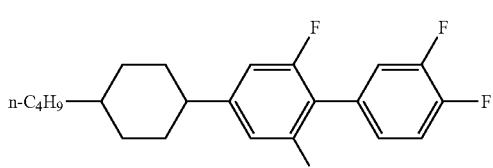

(55.4)

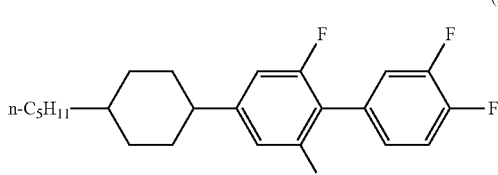

Furthermore, the compounds represented by the general formula (XIV-2) are preferably compounds represented by general formula (XIV-2-4).

[Chem. 163]

(XIV-2-4)

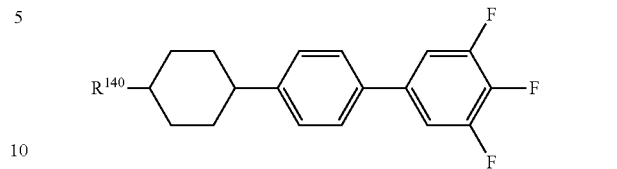

(In the formula, $R^{140}$ represents an alkyl group having 1 to 5 carbon atoms, an alkenyl group having 2 to 5 carbon atoms, or an alkoxy group having 1 to 4 carbon atoms.)

Although the number of compounds that can be combined with each other is not particularly limited, a plurality of the compounds represented by the general formula (XIV-2-4) can be suitably combined for each embodiment in consideration of solubility at low temperature, transition temperature, electrical reliability, double refractive index, and the like. For example, the number of the compounds is one in one embodiment of the present invention. The number of the compounds is two in another embodiment. The number of the compounds is three or more in still another embodiment.

The content of the compounds represented by the general formula (XIV-2-4) has an upper limit and a lower limit for each embodiment in consideration of characteristics such as solubility at low temperature, transition temperature, electrical reliability, and double refractive index.

For example, the content of the compounds is 2 to 35 mass % relative to the total mass of the liquid crystal composition of the present invention in one embodiment of the present invention, 5 to 35 mass % in another embodiment, 8 to 35 mass % in still another embodiment, 9 to 35 mass % in still yet another embodiment, 10 to 35 mass % in still yet another embodiment, 18 to 35 mass % in still yet another embodiment, 21 to 35 mass % in still yet another embodiment, 22 to 35 mass % in still yet another embodiment, and 24 to 35 mass % in still yet another embodiment.

Furthermore, for example, the content of the compounds is 2 to 35 mass % relative to the total mass in one embodiment of the present invention, 2 to 30 mass % in another embodiment, 2 to 25 mass % in still another embodiment, 2 to 20 mass % in still yet another embodiment, 2 to 15 mass % in still yet another embodiment, and 2 to 10 mass % in still yet another embodiment.

When the liquid crystal composition of the present invention is used for liquid crystal display devices having a low drive voltage, it is suitable to increase the content of the compounds represented by the general formula (XIV-2-4). When the liquid crystal composition of the present invention is used for liquid crystal display devices having a high response speed, it is suitable to decrease the content of the compounds represented by the general formula (XIV-2-4).

More specifically, the compounds represented by the general formula (XIV-2-4) are preferably compounds represented by formula (56.1) to formula (56.4) and more preferably a compound represented by formula (56.1), a compound represented by formula (56.2), and/or a compound represented by formula (56.4).

[Chem. 164]

(56.1)
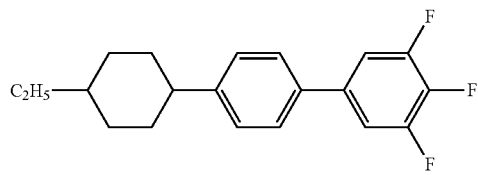

(56.2)
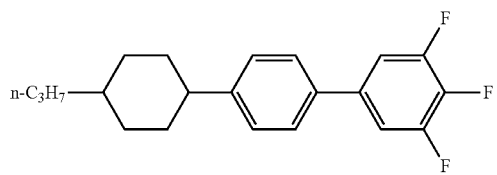

(56.3)
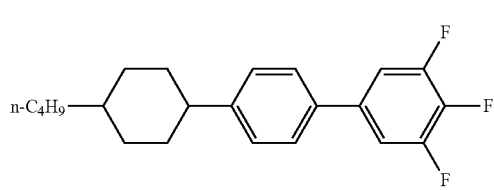

(56.4)
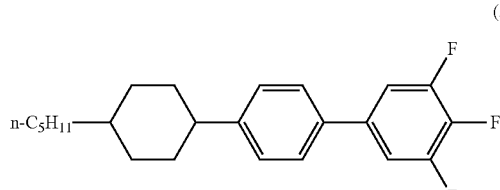

Furthermore, the compounds represented by the general formula (XIV-2) are preferably compounds represented by general formula (XIV-2-5).

[Chem. 165]

(XIV-2-5)
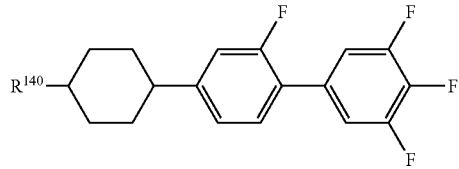

(In the formula, $R^{140}$ represents an alkyl group having 1 to 5 carbon atoms, an alkenyl group having 2 to 5 carbon atoms, or an alkoxy group having 1 to 4 carbon atoms.)

The content of the compounds represented by the general formula (XIV-2-5) is preferably 5 mass % or more and 25 mass % or less, more preferably 10 mass % or more and 22 mass % or less, more preferably 13 mass % or more and 18 mass % or less, and particularly preferably 13 mass % or more and 15 mass % or less relative to the total mass of the liquid crystal composition of the present invention in consideration of solubility at low temperature, transition temperature, electrical reliability, and the like.

More specifically, the compounds represented by the general formula (XIV-2-5) are compounds represented by formula (57.1) to formula (57.4) and preferably a compound represented by formula (57.1).

[Chem. 166]

(57.1)
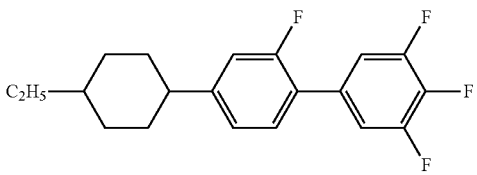

(57.2)
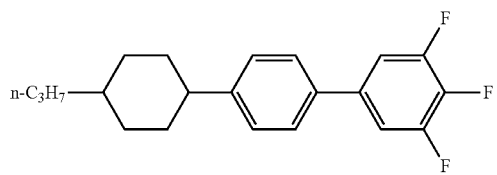

(57.3)
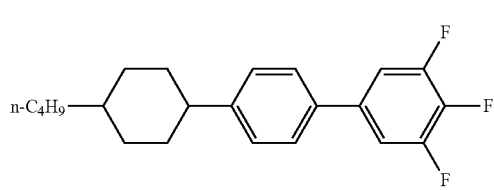

(57.4)
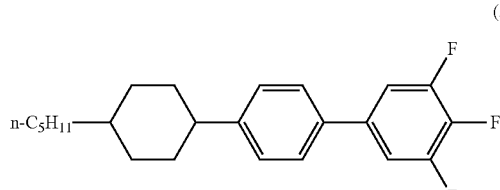

Furthermore, the compounds represented by the general formula (XIV-2) are preferably compounds represented by general formula (XIV-2-6).

[Chem. 167]

(XIV-2-6)
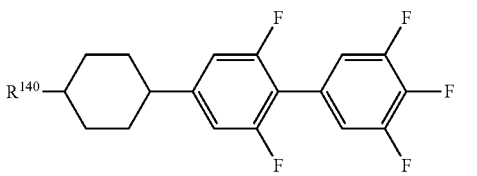

(In the formula, $R^{140}$ represents an alkyl group having 1 to 5 carbon atoms, an alkenyl group having 2 to 5 carbon atoms, or an alkoxy group having 1 to 4 carbon atoms.)

The content of the compounds represented by the general formula (XIV-2-6) is preferably 5 mass % or more and 25 mass % or less, more preferably 10 mass % or more and 22 mass % or less, more preferably 15 mass % or more and 20 mass % or less, and particularly preferably 15 mass % or more and 17 mass % or less relative to the total mass of the liquid crystal composition of the present invention in consideration of solubility at low temperature, transition temperature, electrical reliability, and the like.

More specifically, the compounds represented by the general formula (XIV-2-6) are preferably compounds represented by formula (58.1) to formula (58.4) and more preferably a compound represented by formula (58.2).

[Chem. 168]

(58.1)

(58.2)
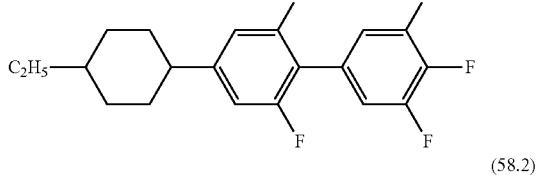

(58.3)
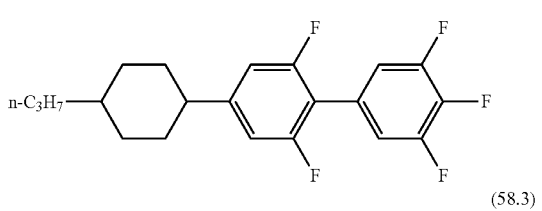

(58.4)
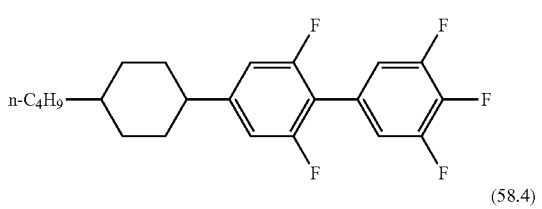

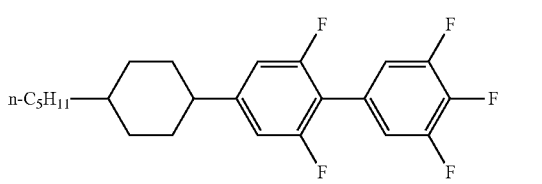

The compounds used in the present invention do not have a peracid (—CO—OO—) structure in their molecules. When an importance is given to the reliability and long-term stability of the liquid crystal composition, a compound having a carbonyl group is preferably not used. When an importance is given to the stability for UV irradiation, a compound subjected to substitution with chlorine atoms is desirably not used. The liquid crystal composition is also preferably constituted by only compounds in which all the intramolecular ring structures are six-membered rings.

The liquid crystal composition of the present invention preferably does not contain a compound intramolecularly having a structure in which oxygen atoms bond to each other, such as a peracid (—CO—OO—) structure.

When an importance is given to the reliability and long-term stability of the liquid crystal composition, the content of the compound having a carbonyl group is preferably 5 mass % or less, more preferably 3 mass % or less, and more preferably 1 mass % or less relative to the total mass of the composition. Most preferably, the liquid crystal composition substantially does not contain the compound having a carbonyl group.

When an importance is given to the stability for UV irradiation, the content of the compound subjected to substitution with chlorine atoms is preferably 15 mass % or less, more preferably 10 mass % or less, and more preferably 5 mass % or less relative to the total mass of the composition. Most preferably, the liquid crystal composition substantially does not contain the compound subjected to substitution with chlorine atoms.

The content of the compound in which all the intramolecular ring structures are six-membered rings is preferably increased. The content of the compound in which all the intramolecular ring structures are six-membered rings is preferably 80 mass % or more, more preferably 90 mass % or more, and more preferably 95 mass % or more relative to the total mass of the composition. Most preferably, the liquid crystal composition is substantially constituted by only compounds in which all the intramolecular ring structures are six-membered rings.

To suppress the degradation due to oxidation of the liquid crystal composition, the content of a compound having a cyclohexenylene group as a ring structure is preferably decreased. The content of the compound having a cyclohexenylene group is preferably 10 mass % or less and more preferably 5 mass % or less relative to the total mass of the composition. More preferably, the liquid crystal composition substantially does not contain the compound having a cyclohexenylene group.

When an importance is given to the improvement in viscosity and Tni, the content of a compound intramolecularly having a 2-methylbenzene-1,4-diyl group whose hydrogen atoms may be substituted with halogens is preferably decreased. The content of the compound intramolecularly having a 2-methylbenzene-1,4-diyl group is preferably 10 mass % or less and more preferably 5 mass % or less relative to the total mass of the composition. More preferably, the liquid crystal composition substantially does not contain the compound intramolecularly having a 2-methylbenzene-1,4-diyl group.

In the case where the compound contained in the composition according to the first embodiment of the present invention has an alkenyl group as a side chain, when the alkenyl group bonds to cyclohexane, the number of carbon atoms in the alkenyl group is preferably 2 to 5. When the alkenyl group bonds to benzene, the number of carbon atoms in the alkenyl group is preferably 4 or 5. The unsaturated bond of the alkenyl group is preferably not directly bonded to benzene.

The liquid crystal composition of the present invention may contain a polymerizable compound in order to produce, for example, a PS mode-, a transverse electric field-type PSA mode-, or a transverse electric field-type PSVA mode- liquid crystal display device. For example, a photopolymerizable monomer whose polymerization proceeds with energy rays such as light can be used as the polymerizable compound. In terms of structure, a polymerizable compound having a liquid crystal skeleton formed by bonding a plurality of six-membered rings, such as a biphenyl derivative or a terphenyl derivative is exemplified. More specifically, the polymerizable compound is preferably a bifunctional monomer represented by general formula (XX).

[Chem. 169]

(XX)
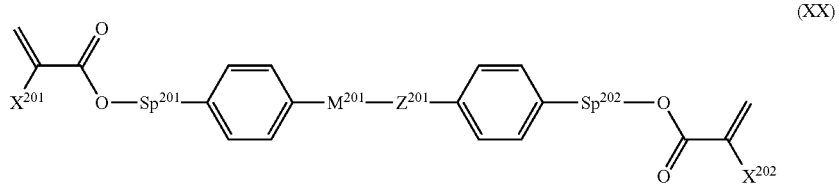

(In the formula, $X^{201}$ and $X^{202}$ each independently represent a hydrogen atom or a methyl group;
$Sp^{201}$ and $Sp^{202}$ each independently represent a single bond, an alkylene group having 1 to 8 carbon atoms, or —O—$(CH_2)_s$—
(where s represents an integer of 2 to 7 and the oxygen atom bonds to an aromatic ring);
$Z^{201}$ represents —OCH$_2$—, —CH$_2$O—, —COO—, —OCO—, —CF$_2$O—, —OCF$_2$—, —CH$_2$CH$_2$—, —CF$_2$CF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CY$^1$=CY$^2$— (where $Y^1$ and $Y^2$ each independently represent a fluorine atom or a hydrogen atom), —C≡C—, or a single bond; and
$M^{201}$ represents a 1,4-phenylene group, a trans-1,4-cyclohexylene group, or a single bond and, in all the 1,4-phenylene groups in the formula, any of hydrogen atoms may be substituted with fluorine atoms.)

The polymerizable compound is preferably any of a diacrylate derivative in which $X^{201}$ and $X^{202}$ each represent a hydrogen atom and a dimethacrylate derivative in which $X^{201}$ and $X^{202}$ each represent a methyl group, and is also preferably a compound in which one of $X^{201}$ and $X^{202}$ represents a hydrogen atom and the other represents a methyl group. Among these compounds, the diacrylate derivative has the highest rate of polymerization, the dimethacrylate derivative has a low rate of polymerization, and the asymmetrical compound has an intermediate rate of polymerization. A preferred one can be used in accordance with the applications. In PSA display devices, the dimethacrylate derivative is particularly preferably used.

$Sp^{201}$ and $Sp^{202}$ each independently represent a single bond, an alkylene group having 1 to 8 carbon atoms, or —O—$(CH_2)_s$—. In PSA display devices, at least one of $Sp^{201}$ and $Sp^{202}$ preferably represents a single bond. A compound in which $Sp^{201}$ and $Sp^{202}$ each represent a single bond or a compound in which one of $Sp^{201}$ and $Sp^{202}$ represents a single bond and the other represents an alkylene group having 1 to 8 carbon atoms or —O—$(CH_2)_s$— is preferred. In this case, an alkyl group having 1 to 4 carbon atoms is preferred and s is preferably 1 to 4.

$Z^{201}$ preferably represents —OCH$_2$—, —CH$_2$O—, —COO—, —OCO—, —CF$_2$O—, —OCF$_2$—, —CH$_2$CH$_2$—, —CF$_2$CF$_2$—, or a single bond, more preferably —COO—, —OCO—, or a single bond, and particularly preferably a single bond.

$M^{201}$ represents a 1,4-phenylene group in which any of hydrogen atoms may be substituted with fluorine atoms, a trans-1,4-cyclohexylene group, or a single bond and preferably represents a 1,4-phenylene group or a single bond. When $M^{201}$ represents a ring structure other than a single bond, $Z^{201}$ preferably represents a linking group other than a single bond. When $M^{201}$ represents a single bond, $Z^{201}$ preferably represents a single bond.

In view of the foregoing, the ring structure between $Sp^{201}$ and $Sp^{202}$ in the general formula (XX) is preferably the following structure.

In the case where $M^{201}$ represents a single bond and the ring structure is constituted by two rings in the general formula (XX), the ring structure is preferably represented by formula (XXa-1) to formula (XXa-5) below, more preferably represented by formula (XXa-1) to formula (XXa-3), and particularly preferably represented by formula (XXa-1).

[Chem. 170]

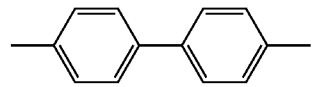

(XXa-1)

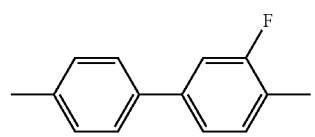

(XXa-2)

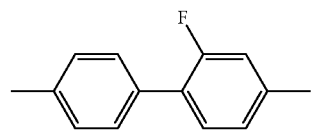

(XXa-3)

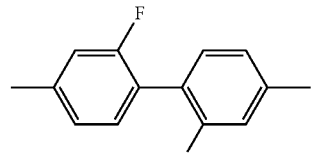

(XXa-4)

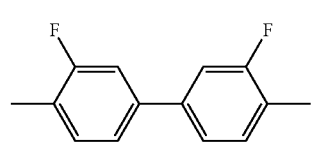

(XXa-5)

(In the formulae, both ends bond to $Sp^{201}$ and $Sp^{202}$.)

The anchoring strength after the polymerization of the polymerizable compound having such a skeleton is suitable for PSA mode liquid crystal display devices, and a good alignment state is achieved. Therefore, the display unevenness is suppressed or completely prevented.

Accordingly, the polymerizable monomer is particularly preferably represented by general formula (XX-1) to general formula (XX-4) and most preferably represented by general formula (XX-2).

[Chem. 171]

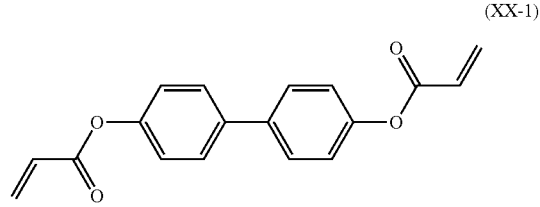

(XX-1)

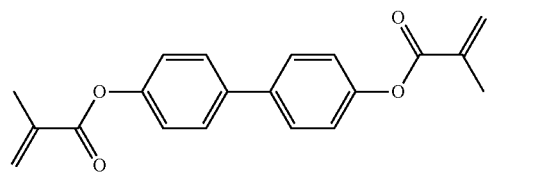

(XX-2)

-continued (XX-3)

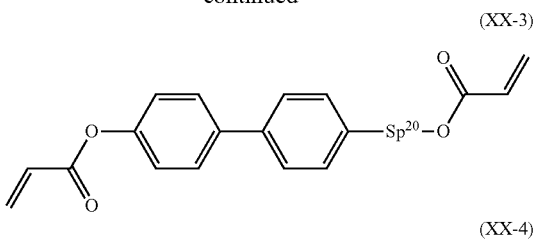

(XX-4)

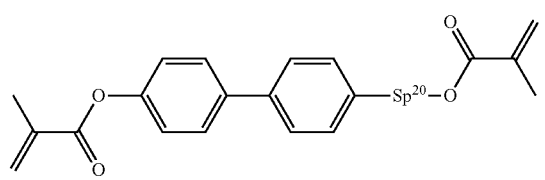

(In the formulae, Sp$^{20}$ represents an alkylene group having 2 to 5 carbon atoms.)

In the case where the monomer is added to the liquid crystal composition of the present invention, polymerization proceeds without a polymerization initiator, but a polymerization initiator may be contained to facilitate the polymerization. Examples of the polymerization initiator include benzoin ethers, benzophenones, acetophenones, benzylketals, and acylphosphine oxides.

The liquid crystal composition of the present invention may further contain compounds represented by general formula (Q).

[Chem. 172]

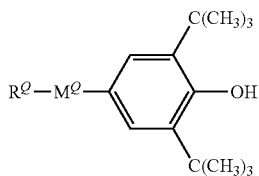

(Q)

(In the formula, R$^Q$ represents a linear or branched alkyl group having 1 to 22 carbon atoms, where one or more CH$_2$ groups in the alkyl group may be substituted with —O—, —CH=CH—, —CO—, —OCO—, —COO—, —C≡C—, —CF$_2$O—, or —OCF$_2$— so that oxygen atoms are not directly adjacent to each other; and M$^Q$ represents a trans-1,4-cyclohexylene group, a 1,4-phenylene group, or a single bond.)

R$^Q$ represents a linear or branched alkyl group having 1 to 22 carbon atoms, where one or more CH$_2$ groups in the alkyl group may be substituted with —O—, —CH=CH—, —CO—, —OCO—, —COO—, —C≡C—, —CF$_2$O—, or —OCF$_2$— so that oxygen atoms are not directly adjacent to each other. R$^Q$ preferably represents a linear alkyl group, a linear alkoxy group, a linear alkyl group in which one CH$_2$ group is substituted with —OCO— or —COO—, a branched alkyl group, a branched alkoxy group, or a branched alkyl group in which one CH$_2$ group is substituted with —OCO— or —COO—, all of which have 1 to 10 carbon atoms. R$^Q$ more preferably represents a linear alkyl group, a linear alkyl group in which one CH$_2$ group is substituted with —OCO— or —COO—, a branched alkyl group, a branched alkoxy group, or a branched alkyl group in which one CH$_2$ group is substituted with —OCO— or —COO—, all of which have 1 to 20 carbon atoms. M$^Q$ represents a trans-1,4-cyclohexylene group, a 1,4-phenylene group, or a single bond. M$^Q$ preferably represents a trans-1,4-cyclohexylene group or a 1,4-phenylene group.

More specifically, the compounds represented by the general formula (Q) are preferably compounds represented by general formula (Q-a) to general formula (Q-d) below.

[Chem. 173]

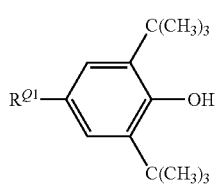

(Q-a)

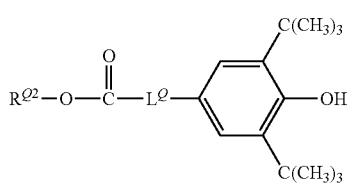

(Q-b)

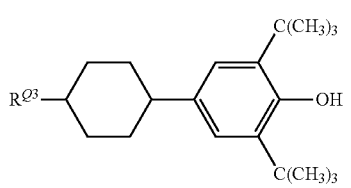

(Q-c)

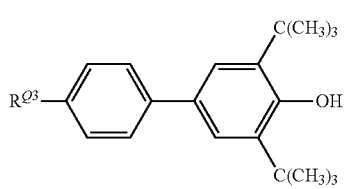

(Q-d)

In the formula, R$^{Q1}$ preferably represents a linear alkyl group or branched alkyl group having 1 to 10 carbon atoms; R$^{Q2}$ preferably represents a linear alkyl group or branched alkyl group having 1 to 20 carbon atoms; R$^{Q3}$ preferably represents a linear alkyl group, branched alkyl group, linear alkoxy group, or branched alkoxy group having 1 to 8 carbon atoms; and L$^Q$ preferably represents a linear alkylene group or branched alkylene group having 1 to 8 carbon atoms. Among the compounds represented by the general formula (Q-a) to the general formula (Q-d), the compounds represented by the general formula (Q-c) and the general formula (Q-d) are more preferable.

The liquid crystal composition of the present invention preferably contains one or two of the compounds represented by the general formula (Q) and more preferably contains one to five of the compounds. The content of the compounds is preferably 0.001 to 1 mass %, more preferably 0.001 to 0.1 mass %, and particularly preferably 0.001 to 0.05 mass %.

<Liquid Crystal Display Device>

The liquid crystal composition containing the polymerizable compound according to the present invention is provided with liquid crystal alignment capability by polymerizing the polymerizable compound through irradiation with ultraviolet light and is used for liquid crystal display devices that control the amount of transmitted light by using the double refraction of the liquid crystal composition. The liquid crystal composition is useful for liquid crystal display devices such as an ECB-LCD, a VA-LCD, an FFS-LCD, an AM-LCD (active matrix liquid crystal display device), a TN (nematic liquid crystal display device), an STN-LCD (super-twisted nematic liquid crystal display device), an OCB-LCD, and an IPS-LCD (in-plane switching liquid crystal display device). The liquid crystal composition is particularly useful for AM-LCDs and can be used for transmission or reflection-type liquid crystal display devices.

Two substrates of a liquid crystal cell used in a liquid crystal display device may be composed of glass or a flexible transparent material such as a plastic material. One of the substrates may be composed of an opaque material such as silicon. A transparent substrate having a transparent electrode layer can be produced by, for example, sputtering indium tin oxide (ITO) on a transparent substrate such as a glass plate.

A color filter can be produced by, for example, a pigment dispersion method, a printing method, an electrodeposition method, or a staining method. A method for producing a color filter will be described by taking the pigment dispersion method as an example. A curable coloring composition for color filters is applied onto the above-described transparent substrate and patterned. The curable coloring composition is then cured by heating or light irradiation. This process is performed for each of three colors of red, green, and blue. Thus, pixel portions of the color filter can be formed. Furthermore, pixel electrodes each including an active element such as a TFT or a thin-film diode may be disposed on the substrate.

The substrates are arranged so as to face each other such that the transparent electrode layer is disposed inside. Herein, the gap between the substrates may be adjusted with a spacer disposed therebetween. In this case, the gap is preferably adjusted so that the thickness of a light-modulating layer obtained is 1 to 100 µm, and more preferably 1.5 to 10 µm. When a polarizing plate is used, it is preferable to adjust the product of the refractive index anisotropy $\Delta n$ of the liquid crystal and a cell thickness d so that the maximum contrast is achieved. When two polarizing plates are used, the polarizing axis of each of the polarizing plates may be adjusted so that a satisfactory viewing angle and contrast can be achieved. Furthermore, a retardation film for widening the viewing angle may also be used. Examples of the spacer include glass particles, plastic particles, alumina particles, and pillar-shaped spacers composed of a photoresist material or the like. Subsequently, a sealant such as an epoxy thermosetting composition is applied onto the substrate by screen printing while a liquid-crystal injection port is formed. The substrates are bonded to each other, and the sealant is thermally cured by heating.

A commonly used vacuum injection method, an ODF method, or the like can be employed as a method for interposing the polymerizable compound-containing liquid crystal composition between the two substrates. In the vacuum injection method, although drop marks are not generated, this method has a problem in that marks of injection are left. However, in the present invention, the liquid crystal composition can be suitably used for display devices produced by using the ODF method. In the production process of a liquid crystal display device by the ODF method, a sealant such as an epoxy-based photothermal dual curing sealant is applied onto one of the substrates serving as a backplane and a frontplane using a dispenser so as to form a closed-loop bank-like shape. A predetermined amount of the liquid crystal composition is dropped therein under deaeration, and then the frontplane and the backplane are bonded to each other to produce a liquid crystal display device. The liquid crystal composition of the present invention can be suitably used because the dropping of the liquid crystal composition can be stably performed in the ODF process.

As a method for polymerizing the polymerizable compound, a method in which polymerization is conducted by irradiation with active energy rays such as ultraviolet light and an electron beam, which can be used alone, in combination, or sequentially, is preferred because a moderate rate of polymerization is desirable in order to achieve good liquid crystal alignment capability. In the case where ultraviolet light is used, either a polarized light source or an unpolarized light source may be used. When polymerization is conducted while the polymerizable compound-containing liquid crystal composition is interposed between the two substrates, it is necessary that at least a substrate on the irradiation surface side have transparency appropriate for the active energy rays. Only specific portions may be polymerized using a mask during light irradiation, and unpolymerized portions may then be polymerized by further irradiation with active energy rays while the alignment state of the unpolymerized portions is changed by changing a condition such as the electric field, the magnetic field, or the temperature. In particular, when ultraviolet exposure is performed, the ultraviolet exposure is preferably performed while an alternating electric field is applied to the polymerizable compound-containing liquid crystal composition. Regarding the alternating electric field applied, an alternating current having a frequency of preferably 10 Hz to 10 kHz and more preferably 60 Hz to 10 kHz is applied, and the voltage applied is selected in accordance with a desired pre-tilt angle of the liquid crystal display device. That is, the pre-tilt angle of the liquid crystal display device can be controlled by controlling the voltage applied. In a transverse electric field-type MVA mode liquid crystal display device, it is preferable to control the pre-tilt angle to 80 to 89.9 degrees from the viewpoint of the alignment stability and the contrast.

The temperature during the irradiation is preferably within a temperature range in which the liquid crystal state of the liquid crystal composition of the present invention is maintained. Polymerization is preferably conducted at a temperature close to room temperature, that is, typically at a temperature of 15° C. to 35° C. A metal halide lamp, a high-pressure mercury lamp, an ultrahigh-pressure mercury lamp, or the like can be used as a lamp for generating ultraviolet light. Regarding the wavelength of ultraviolet light for irradiation, it is preferable to perform irradiation with ultraviolet light in a wavelength range which is not included in an absorption wavelength range of the liquid crystal composition. When necessary, part of the ultraviolet light is preferably cut off and used. The intensity of ultraviolet light for irradiation is preferably 0.1 mW/cm$^2$ to 100 W/cm$^2$ and more preferably 2 mW/cm$^2$ to 50 W/cm$^2$. The amount of energy of the ultraviolet light for irradiation can be appropriately adjusted, and is preferably 10 mJ/cm$^2$ to 500 J/cm$^2$ and more preferably 100 mJ/cm$^2$ to 200 J/cm$^2$. During the irradiation with ultraviolet light, the intensity of the ultraviolet light may be changed. The ultraviolet-irradiation time is appropriately selected in accordance with the intensity of the ultraviolet light for irradiation, and is preferably 10 to 3600 seconds and more preferably 10 to 600 seconds.

The liquid crystal display device using the liquid crystal composition of the present invention is a useful display device which realizes both high-speed response and suppression of display defects. The liquid crystal display device is particularly useful as a liquid crystal display device for active-matrix driving and can be applied to a VA mode, PSVA mode, PSA mode, IPS (in-plane switching) mode, FSS (fringe-field switching) mode, or ECB mode liquid crystal display device.

A preferred embodiment of a liquid crystal display apparatus (liquid crystal display) according to the present invention will be described in detail with reference to the attached drawings.

FIG. 1 is a cross-sectional view showing a liquid crystal display device including two substrates facing each other, a sealing material disposed between the substrates, and liquid crystal sealed in a sealing region surrounded by the sealing material.

A specific embodiment of the liquid crystal display device includes a backplane that includes a TFT layer 102 and a pixel electrode 103 disposed on a first substrate 100, and a passivation film 104 and a first alignment film 105 disposed thereon; a frontplane that faces the backplane and that includes a black matrix 202, a color filter 203, a planarizing film (overcoat layer) 201, and a transparent electrode 204 disposed on a second substrate 200, and a second alignment film 205 disposed thereon; a sealing material 301 disposed between the substrates; a liquid crystal layer 303 sealed in a sealing region surrounded by the sealing material; and projections (columnar spacers) 302 and 304 on the surface of the substrate in contact with the sealing material 301.

The first substrate and the second substrate may be composed of any material that is substantially transparent and glass, ceramic, plastic, and the like can be used. Examples of a material that can be used for a plastic substrate include cellulose, cellulose derivatives such as triacetyl cellulose and diacetyl cellulose, polycycloolefin derivatives, polyesters such as polyethylene terephthalate and polyethylene naphthalate, polyolefins such as polypropylene and polyethylene, polycarbonate, polyvinyl alcohols, polyvinyl chloride, polyvinylidene chloride, polyamide, polyimide, polyimide amide, polystyrene, polyacrylate, polymethyl methacrylate, polyether sulfone, polyarylate, and inorganic-organic composite materials such as glass fiber-epoxy resin and glass fiber-acrylic resin.

In the case where a plastic substrate is used, a barrier film is preferably provided. The function of the barrier film is to decrease the moisture permeability of the plastic substrate and improve the reliability of the electric properties of the liquid crystal display device. The barrier film is not particularly limited as long as the film has high transparency and low water vapor permeability. Typically, a thin film formed by using an inorganic material such as silicon oxide through vapor deposition, sputtering, or chemical vapor deposition (CVD) is used.

In the present invention, the same material or different materials may be used in the first substrate and the second substrate. Glass substrates are preferably used because a liquid crystal display device having good heat resistance and dimensional stability can be fabricated. Plastic substrates are also preferably used because they are suitable for performing a roll-to-roll production method, achieving light weight, and providing flexibility. If flatness and heat resistance are desirable, a plastic substrate and a glass substrate are preferably used in combination, which can yield preferable results.

In Examples described below, substrates are used as the materials for the first substrate 100 and the second substrate 200.

In the backplane, the TFT layer 102 and the pixel electrode 103 are disposed on the first substrate 100. The TFT layer 102 and the pixel electrode 103 are produced in a typical array process. The passivation film 104 and the first alignment film 105 are formed thereon and a backplane is obtained as a result.

The passivation film 104 (also referred to as an inorganic protective film) is a film for protecting the TFT layer and is typically formed by, for example, a chemical vapor deposition (CVD) technique as a nitride film (SiNx), an oxide film (SiOx), or the like.

The first alignment film 105 has a function of aligning liquid crystal and a polymer material such as polyimide is often used for the first alignment film 105. An alignment agent solution composed of a polymer material and a solvent is used as the coating solution. The alignment film has a possibility of inhibiting adhesive force to the sealing material and is thus patterned and applied in the sealing region. A printing method such as flexographic printing or a droplet ejection method such as ink jet is employed for application. After the solvent is evaporated by precuring, the applied alignment agent solution is crosslinked and cured by baking. Subsequently, an aligning process is performed to generate an aligning function.

The aligning process is usually performed by a rubbing technique. The polymer film formed as described above is rubbed in one direction with a rubbing cloth composed of fiber such as rayon so as to generate liquid crystal alignment capability.

Alternatively, an optical alignment technique is sometimes employed. The optical alignment technique is a technique of generating the alignment capability by irradiating an alignment film containing a photosensitive organic material with polarized light. According to this technique, scratching of the substrate and generation of dust that occur in the rubbing technique do not occur. An example of the organic material used in the optical alignment technique is a material that contains dichroic dyes. Examples of the dichroic dyes that can be used include those that have groups (hereinafter simply referred to as optical alignment groups) that induce molecular alignment by the Weigert's effect resulting from dichroism or induce optical reaction from which the liquid crystal alignment capability originates, such as isomerization reaction (e.g., azobenzene group), dimerization reaction (e.g., cinnamoyl group), optical crosslinking reaction (e.g., benzophenone group), or photolytic reaction (e.g., polyimide group). The applied aligning agent solution is precured to evaporate the solvent and then irradiated with light (polarized light) having a desired polarization to obtain an alignment film having alignment capability in the desired direction.

The frontplane includes the black matrix 202, the color filter 203, the planarizing film 201, the transparent electrode 204, and the second alignment film 205 disposed on the second substrate 200.

The black matrix 202 is, for example, fabricated by a pigment dispersion method. Specifically, a color resin solution containing a uniformly dispersed black colorant for forming a black matrix is applied onto the second substrate 200 having the barrier film 201 formed thereon to form a coloring layer. The coloring layer is then cured by baking. A photoresist is applied onto the coloring layer and prebaked. The photoresist is exposed through a mask pattern and then developed to pattern the coloring layer. Subsequently, the photoresist layer is removed and the coloring layer is baked to form the black matrix 202.

Alternatively, a photoresist-type pigment dispersion liquid may be used. In this case, a photoresist-type pigment dispersion liquid is applied, prebaked, exposed through a mask pattern, and then developed to pattern the coloring layer. Then, the photoresist layer is removed and the coloring layer is baked to form the black matrix 202.

The color filter 203 is prepared by a pigment dispersion method, an electrodeposition method, a printing method, a staining method, or the like. For example, in the pigment dispersion method, a color resin solution in which a pigment (e.g., a red pigment) is uniformly dispersed is applied onto the second substrate 200 and cured by baking. Then, a photoresist is applied thereon and prebaked. The photoresist is exposed through a mask pattern and then developed to perform patterning. The photoresist layer is then removed and baking is performed again. As a result, a (red) color filter 203 is prepared. The order of color in which the filters are made is not particularly limited. A green color filter 203 and a blue color filter 203 are prepared in the same manner.

The transparent electrode 204 is formed on the color filter 203 (if needed, an overcoat layer (201) for planarizing the surface is formed on the color filter 203). The transmittance of the transparent electrode 204 is preferably high and the electrical resistance of the transparent electrode 204 is preferably low. The transparent electrode 204 is formed by performing sputtering-deposition or the like of an oxide film composed of, for example, ITO.

A passivation film is sometimes formed on the transparent electrode 204 to protect the transparent electrode 204.

The second alignment film 205 is the same as the first alignment film 105.

Although specific embodiments of the backplane and the frontplane used in the present invention have been described above, the present invention is not limited to these specific embodiments and these embodiments may be freely altered depending on the desired liquid crystal display device.

The shape of the columnar spacers is not particularly limited and its horizontal cross section may have a variety of shapes such as a circle and polygons, e.g., a quadrilateral. Considering the misalignment margin during the process, the horizontal cross section particularly preferably has a circular or regular polygonal shape. The shape of the projections is preferably a truncated cone or truncated pyramid shape.

The material of the columnar spacers is not particularly limited as long as it is a material that does not dissolve in the sealing material, the organic solvent used in the sealing material, or the liquid crystal. From the viewpoints of processing and weight reduction, a synthetic resin (curable resin) is preferable. The projections can be formed by a photolithographic method or a droplet ejection method on the surface of the first substrate that comes into contact with the sealing material. For these reasons, it is preferable to use a photocurable resin suitable for a photolithographic method or a droplet ejection method.

Figure 2:
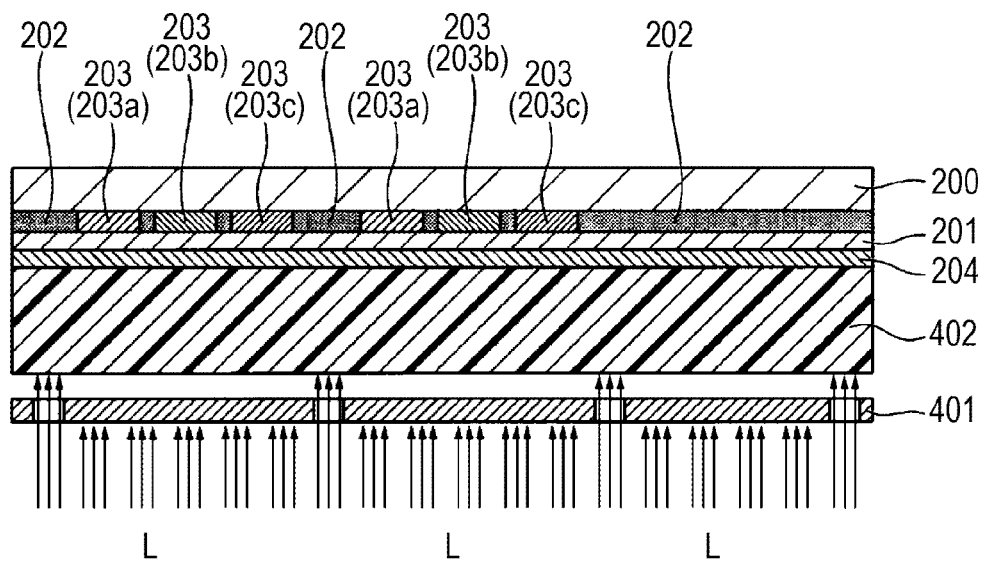
FIG. 2 is a diagram of an exposure process that uses a pattern for forming columnar spacers, the pattern being formed on a black matrix so as to function as a photomask pattern.

The case in which the columnar spacers are obtained by a photolithographic method will be described below as an example. FIG. 2 is a diagram of an exposure process that uses a pattern for forming columnar spacers, the pattern being formed on the black matrix so as to function as a photomask pattern.

A resin solution for forming columnar spacers (not containing colorants) is applied onto the transparent electrode 204 of the frontplane. Then, this resin layer 402 is cured by baking. A photoresist is applied thereon and prebaked. The photoresist is exposed through a mask pattern 401 and then developed to pattern the resin layer. The photoresist layer is then removed and the resin layer is baked to form the columnar spacers (302 and 0304 in FIG. 1).

The positions of the columnar spacers formed can be determined as desired by using a mask pattern. Accordingly, the columnar spacers can be formed inside the sealing region and outside the sealing region (portion where the sealing material is applied) simultaneously. The columnar spacers are preferably formed so as to be located on the black matrix so that the quality of the sealing region does not degrade. The columnar spacers fabricated by a photolithographic method as such are sometimes called column spacers or photo spacers.

A mixture containing, for example, a triazole initiator, an acrylic acid copolymer, a polyfunctional acrylic monomer, or a negative-type water-soluble resin such as PVA-stilbazo photosensitive resin is used as the material for the spacers. Alternatively, a method that uses a color resin in which a colorant is dispersed in a polyimide resin is employed. In the present invention, the spacers can be obtained without any limitation by using a known material in accordance with the compatibility with the liquid crystal and the sealing material used.

After the columnar spacers are formed on the surface of the frontplane where a sealing region is to be formed, a sealing material (301 in FIG. 1) is applied onto the surface of the backplane that comes into contact with the sealing material.

The material for the sealing material is not particularly limited, and a curable resin composition obtained by adding a polymerization initiator to an epoxy-based or acrylic-based photocurable, thermally curable, or photothermal dual curing resin is used. In order to control the moisture permeability, elastic modulus, and viscosity, a filler composed of an inorganic matter or an organic matter may be added. The shape of the filler is not particularly limited and may be spherical, fibrous, or irregular. A spherical gap material that has a monodisperse diameter or a fibrous gap material may be mixed in order to satisfactorily control the cell gap or a fibrous substance that easily becomes entangled with the projections on the substrate may be mixed in order to further strengthen the adhesive force to the substrate. The diameter of the fibrous substance used here is preferably about $1/5$ to $1/10$ of the cell gap or less. The length of the fibrous substance is preferably smaller than the width of the applied seal.

The material of the fibrous substance is not particularly limited as long as a particular shape can be obtained. A synthetic fiber such as cellulose, polyamide, or polyester, or an inorganic material such as glass or carbon can be appropriately selected.

A printing method and a dispensing method are available as the method for applying the sealing material. A dispensing method that uses less sealing material is preferable. The positions where the sealing material is applied are usually on a black matrix so as not to adversely affect the sealing region. In order to form a liquid crystal dropping region in the next step (in order to prevent leakage of the liquid crystal), the sealing material is applied so as to have a closed loop shape.

Liquid crystal is dropped in the closed loop (sealing region) of the frontplane to which the sealing material has been applied. Typically, a dispenser is used. The amount of liquid crystal to be dropped is basically equal to the volume obtained by multiplying the area of the applied seal and the height of the columnar spacer in order for the amount of the liquid crystal dropped to be equal to the cell volume.

However, to deal with liquid crystal leakage that occurs in the cell bonding step and optimize the display properties, the amount of the liquid crystal to be dropped may be appropriately adjusted or the positions where the liquid crystal is to be dropped may be scattered.

Next, the frontplane onto which the sealing material has been applied and the liquid crystal has been dropped is bonded to the backplane. Specifically, the frontplane and the backplane are adsorbed to stages having a substrate adsorbing mechanism such as an electrostatic chuck and are arranged in such a manner that the second alignment film of the frontplane and the first alignment film of the backplane face each other and in such a position (distance) that the sealing material does not contact the other substrate. In this state, the pressure in the system is reduced. Upon completion of the pressure reduction, the positions of the two substrates are adjusted (alignment operation) while checking the position where the frontplane and the backplane are to be bonded to each other. After adjustment of the bonding position is finished, the substrates are brought to be close to each other to a position where the sealing material on the frontplane contacts the backplane. In this state, the interior of the system is filled with inert gas and the pressure is returned to normal pressure by gradually releasing the pressure-reduced state. Herein, the frontplane and the backplane are bonded to each other due to atmospheric pressure, and a cell gap is formed at a height position of the columnar spacers. In this state, the sealing material is cured by being irradiated with ultraviolet light to form a liquid crystal cell. Subsequently, a heating step is performed in some cases so as to accelerate curing of the sealing material. A heating step is often performed in order to strengthen the adhesive force of the sealing material and improve the reliability of electrical properties.

EXAMPLES

The present invention will now be further described below in detail based on Examples, but is not limited to Examples. In the compositions of Examples and Comparative Examples below, "%" means "% by mass".

The properties that were measured in Examples are as follows.

Tni: nematic phase-isotropic liquid phase transition temperature (° C.)

Δn: refractive index anisotropy at 298 K (in other words, double refractive index)

Δ∈: dielectric anisotropy at 298 K

η: viscosity (mPa·s) at 293 K

γ1: rotational viscosity (mPa·s) at 298 K

Initial voltage holding ratio (initial VHR): voltage holding ratio (%) at a frequency of 60 Hz and an applied voltage of 4 V at 323 K Voltage holding ratio after heating (VHR after heating): voltage holding ratio (%) measured under the same conditions as those of the initial VHR after holding was performed at 423 K for one hour <Image Sticking Evaluation>

Image sticking evaluation for the liquid crystal display device was performed by performing uniform display in the entire screen after displaying a particular fixed pattern in a display area for 1176 hours, and visually evaluating the degree of the afterimage of the fixed pattern based on the four-grade evaluation below:

A: No afterimage was observed.

B: Faint afterimage was observed but the degree of the afterimage was acceptable.

C: Afterimage was observed and the degree of the afterimage was unacceptable.

D: Very poor afterimage was observed.

<Evaluation of Volatility (Production Facility Contamination Property)>

The volatility of the liquid crystal material was evaluated through visual observation of foaming of the liquid crystal material while observing the operation state of a vacuum stirring defoaming mixer with a stroboscope. Specifically, 0.8 kg of a liquid crystal composition was placed in a special container for a vacuum stirring defoaming mixer having a capacity of 2.0 L, the vacuum stirring defoaming mixer was driven at a reduced pressure of 4 kPa, a revolution velocity of 15 $S^{-1}$, and a rotation velocity of 7.5 $S^{-1}$, and the following four-grade evaluation was conducted based on the time taken until foaming starts.

A: It took 2 minutes or longer until foaming. The possibility of contamination of facility by evaporation is low.

B: It took 1 minute or longer but less than 2 minutes until foaming. There is a concern that minor facility contamination may occur by evaporation.

C: It took 30 seconds or longer but less than 1 minute until foaming. The facility will be contaminated by evaporation.

D: It took less than 30 seconds until foaming. There is a concern for serious contamination of the facility by evaporation.

<Evaluation of Process Compatibility>

Liquid crystal was dropped 100,000 times at 50 pL per dropping using a constant volume pump in an ODF process and, the changes in the amount of liquid crystal dropped for every 100 droppings, namely, "0 to 100th dropping, 101st to 200th dropping, 201st to 300th dropping, . . . 99901st to 100000th dropping", were evaluated on the following four grades.

A: Very little change was observed (liquid crystal display devices can be stably produced).

B: Slight change was observed but the degree thereof was acceptable.

C: The degree of change was unacceptable (yield was degraded due to generation of nonuniformity).

D: Considerable change was observed (liquid crystal leakage and vacuum bubbles occurred).

<Evaluation of Solubility at Low Temperature>

The solubility at low temperature was evaluated as follows. After a liquid crystal composition was prepared, 0.5 g of the liquid crystal composition was weighed and placed in a 1 mL sample bottle. The resulting sample was continuously exposed to temperature change cycles, each cycle including "−25° C. (retained for 1 hour)→heating (0.2° C./min)→0° C. (retained for 1 hour)→heating (0.2° C./min)→25° C. (retained for 1 hour)→cooling (−0.2° C./min)→0° C. (retained for 1 hour)→cooling (−0.2° C./min)→−25° C." in a temperature control test chamber. Generation of precipitates from the liquid crystal composition was visually observed and the following four-grade evaluation was performed.

A: No precipitates were observed for 500 hours or longer.

B: No precipitates were observed for 300 hours or longer.

C: Precipitates were observed within 100 hours.

D: Precipitates were observed within 50 hours.

Example 1 and Comparative Examples 1 and 2

Compositions were prepared using compounds represented by chemical formulae below. Physical properties of the compositions were measured. Table 1 shows the results.

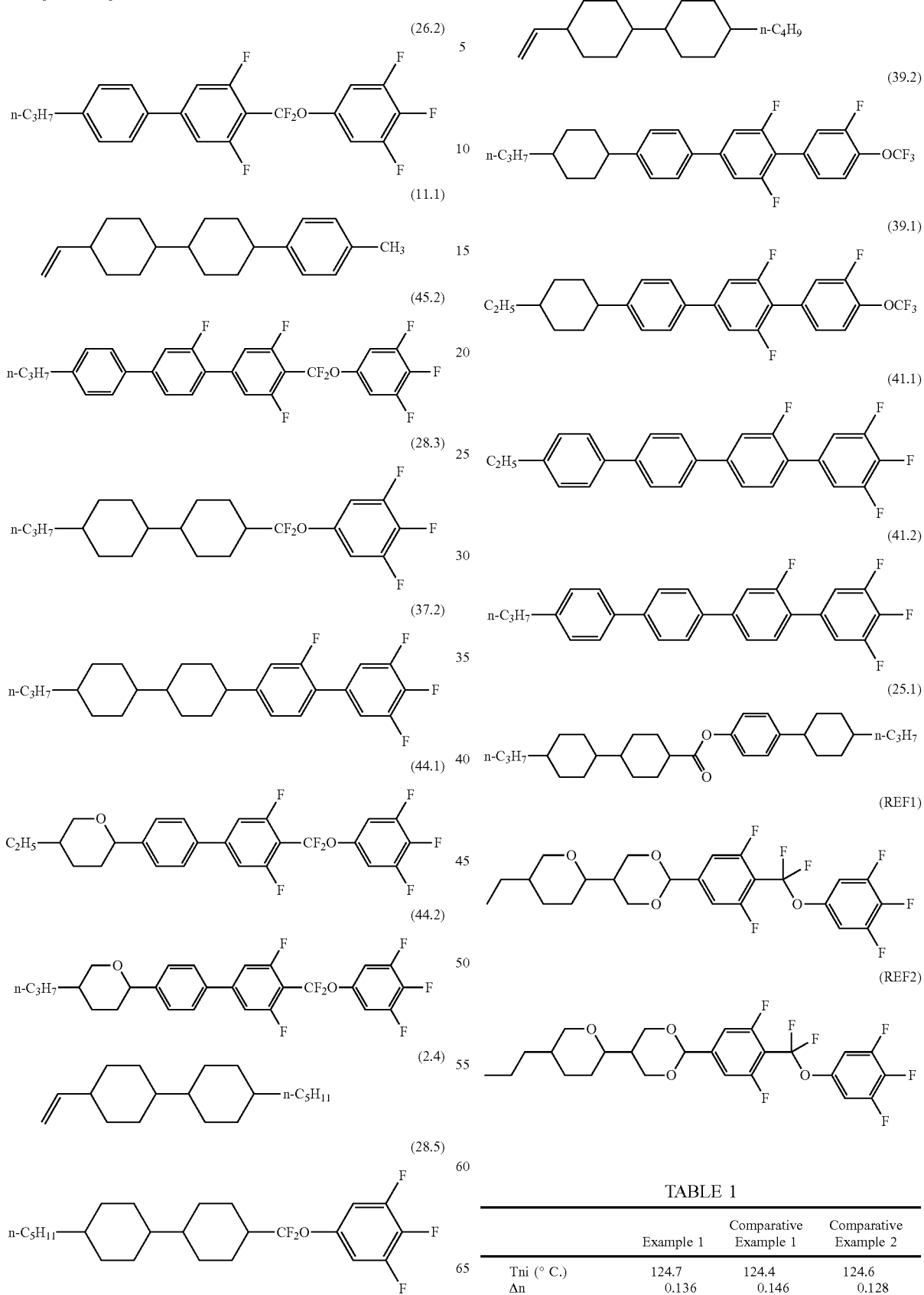
TABLE 1
|  | Example 1 | Comparative Example 1 | Comparative Example 2 |
|---|---|---|---|
| Tni (° C.) | 124.7 | 124.4 | 124.6 |
| Δn | 0.136 | 0.146 | 0.128 |

TABLE 1-continued

|  | Example 1 | Comparative Example 1 | Comparative Example 2 |
|---|---|---|---|
| Δε | 19.8 | 20.0 | 22.4 |
| η (mPa·s) | 51 | 59 | 59 |
| Formula (26.2) | 5 | 5 | 5 |
| Formula (11.1) | 10 | 10 | 10 |
| Formula (45.2) | 10 | 10 | 18 |
| Formula (28.3) | 5 | 5 | 5 |
| Formula (37.2) | 5 | 3 | 5 |
| Formula (44.1) | 10 | 10 | 0 |
| Formula (44.2) | 10 | 10 | 0 |
| Formula (2.4) | 5 | 5 | 5 |
| Formula (28.5) | 5 | 5 | 5 |
| Formula (2.3) | 15 | 15 | 12 |
| Formula (39.2) | 8 | 0 | 10 |
| Formula (39.1) | 7 | 0 | 0 |
| Formula (41.1) | 0 | 7 | 0 |
| Formula (41.2) | 0 | 8 | 0 |
| Formula (25.1) | 5 | 7 | 5 |
| Formula (REF1) | 0 | 0 | 10 |
| Formula (REF2) | 0 | 0 | 10 |

The values for each formula in Table 1 each represent a ratio (unit: mass %) of a compound contained in the composition.

The liquid crystal composition of Comparative Example 1 is a liquid crystal composition obtained by substituting the compounds represented by the general formula (ii) and contained in the liquid crystal composition of Example 1 (the compounds represented by the formula (39.1) and the formula (39.2)) with the compounds represented by the formula (41.1) and the formula (41.2).

As a result of comparison of physical properties between Example 1 and Comparative Example 1, Tni in Example 1 is equal to Tni in Comparative Example 1, but the viscosity η increases due to the absence of the compounds represented by the general formula (ii). Therefore, the viscosity η is lower in Example 1 than in Comparative Example 1. When such a liquid crystal composition is used for liquid crystal devices, a high response speed is achieved.

The liquid crystal composition of Comparative Example 2 is a liquid crystal composition obtained by substituting the compounds represented by the general formula (i) and contained in the liquid crystal composition of Example 1 (the compounds represented by the formula (44.1) and the formula (44.2)) with the compounds represented by the formula (REF1) and the formula (REF2).

As a result of comparison of physical properties between Example 1 and Comparative Example 2, Tni in Example 1 is equal to Tni in Comparative Example 2, but the viscosity η increases due to the absence of the compounds represented by the general formula (i). Therefore, the viscosity η is lower in Example 1 than in Comparative Example 2. When such a liquid crystal composition is used for liquid crystal devices, a high response speed is achieved.

Examples 2 to 5

Compositions were prepared using compounds represented by chemical formulae below. Physical properties of the compositions were measured. Table 2 shows the results.

[Chem. 175]

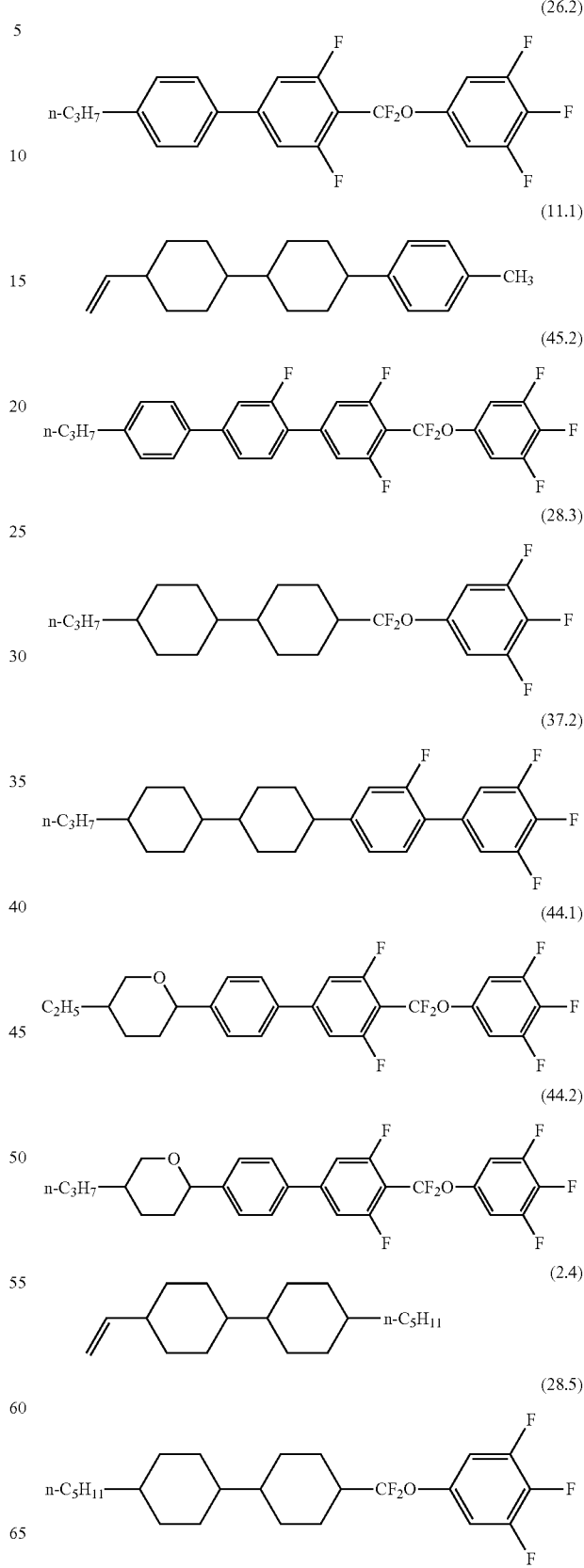

-continued

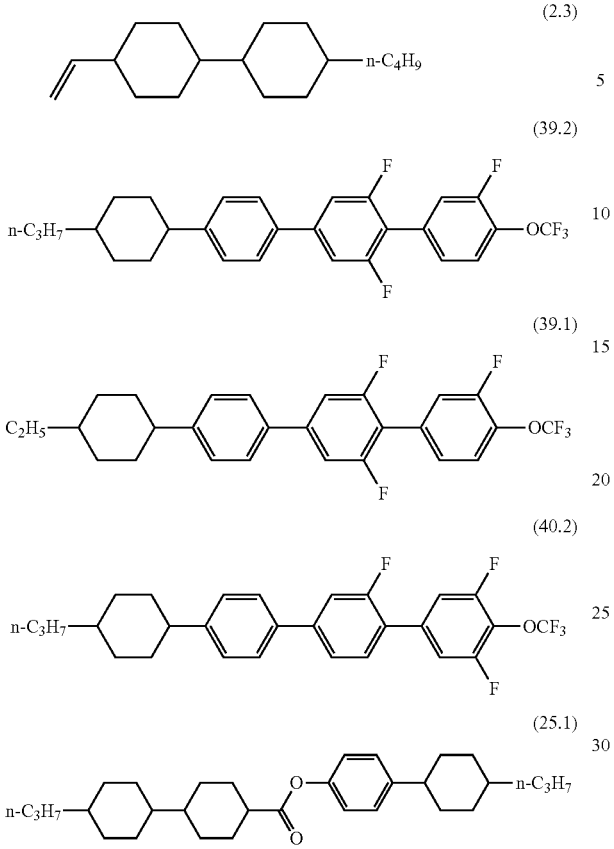

TABLE 2

|  | Example 2 | Example 3 | Example 4 | Example 5 |
|---|---|---|---|---|
| Tni (° C.) | 94.8 | 99.9 | 98.8 | 92.8 |
| Δn | 0.121 | 0.123 | 0.120 | 0.109 |
| Δε | 17.1 | 16.9 | 17.9 | 11.6 |
| η (mPa · s) | 35 | 34 | 38 | 23 |
| γ1 (mPa · s) | 190 | 186 | 252 | 133 |
| Formula (26.2) | 15 | 15 | 10 | 10 |
| Formula (11.1) | 8 | 8 | 5 | 8 |
| Formula (45.2) | 7 | 7 | 7 | 7 |
| Formula (28.3) | 7 | 7 | 7 | 7 |
| Formula (37.2) | 3 | 5 | 4 | 3 |
| Formula (44.1) | 7 | 5 | 11 | 6 |
| Formula (44.2) | 8 | 5 | 11 | 6 |
| Formula (2.4) | 6 | 7 | 5 | 5 |
| Formula (28.5) | 8 | 7 | 8 | 8 |
| Formula (2.3) | 22 | 20 | 25 | 25 |
| Formula (39.2) | 6 | 6 | 4 | 6 |
| Formula (39.1) | 0 | 5 | 0 | 0 |
| Formula (40.2) | 0 | 0 | 0 | 6 |
| Formula (25.1) | 3 | 3 | 3 | 3 |

The values for each formula in Table 2 each represent a ratio (unit: mass %) of a compound contained in the composition.

Table 3 shows the initial VHR, the VHR after heating (423 K, 1 hour), the image sticking evaluation, the evaluation of volatility, the evaluation of process compatibility, and the evaluation of solubility at low temperature of the liquid crystal compositions in Examples 2 to 5.

TABLE 3

|  | Example 2 | Example 3 | Example 4 | Example 5 |
|---|---|---|---|---|
| Initial VHR (%) | 99.2 | 99.4 | 99.1 | 99.2 |
| VHR after heating (%) | 98.3 | 98.2 | 98.2 | 98.1 |
| Image sticking | A | A | A | A |
| Volatility | A | A | A | A |
| Process compatibility | A | B | A | B |
| Solubility at low temperature | A | A | B | A |

Examples 6 to 9

Compositions were prepared using compounds represented by chemical formulae below. Physical properties of the compositions were measured. Table 4 shows the results.

[Chem. 176]

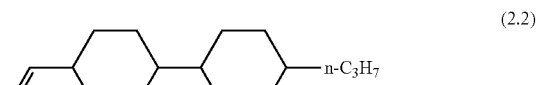

(2.2)

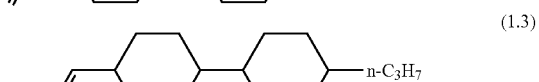

(1.3)

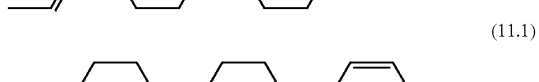

(11.1)

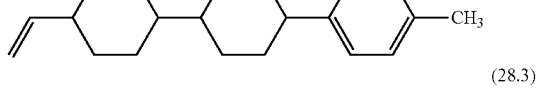

(28.3)

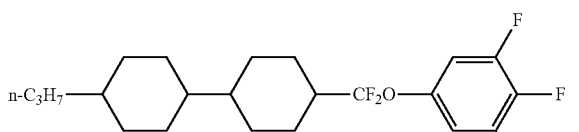

(26.2)

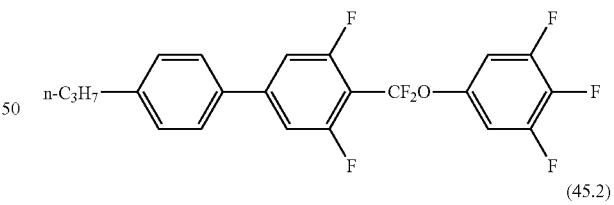

(45.2)

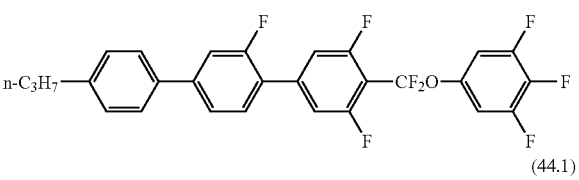

(44.1)

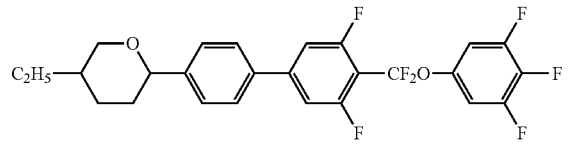

-continued

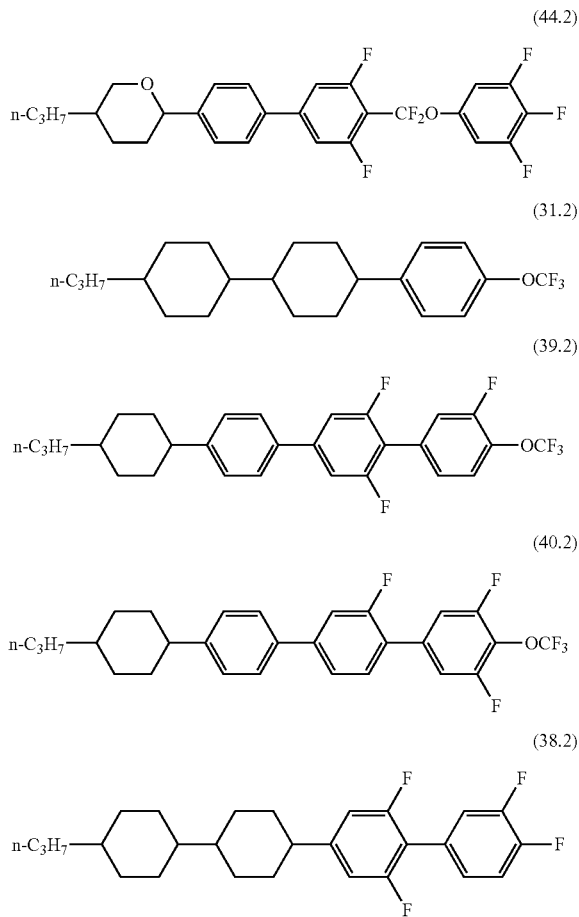

TABLE 4

| | Example 6 | Example 7 | Example 8 | Example 9 |
|---|---|---|---|---|
| Tni (° C.) | 94.5 | 94.2 | 98.1 | 94.5 |
| Δn | 0.120 | 0.122 | 0.124 | 0.120 |
| Δε | 17.2 | 19.5 | 18.5 | 17.2 |
| η (mPa · s) | 35 | 39 | 38 | 35 |
| γ1 (mPa · s) | 186 | 230 | 222 | 186 |
| Formula (2.2) | 40 | 44 | 38 | 40 |
| Formula (1.3) | 16 | 10 | 17 | 16 |
| Formula (11.1) | 5 | 5 | 3 | 5 |
| Formula (28.3) | 2 | 2 | 3 | 2 |
| Formula (26.2) | 8 | 7 | 6 | 8 |
| Formula (45.2) | 4 | 3 | 6 | 4 |
| Formula (44.1) | 4 | 8 | 3 | 4 |
| Formula (44.2) | 4 | 7 | 3 | 4 |
| Formula (31.2) | 6 | 5 | 6 | 6 |
| Formula (39.2) | 6 | 4 | 10 | 3 |
| Formula (40.2) | 0 | 0 | 0 | 3 |
| Formula (38.2) | 5 | 5 | 5 | 5 |

The values for each formula in Table 4 each represent a ratio (unit: mass %) of a compound contained in the composition.

Table 5 shows the initial VHR, the VHR after heating (423 K, 1 hour), the image sticking evaluation, the evaluation of volatility, the evaluation of process compatibility, and the evaluation of solubility at low temperature of the liquid crystal compositions in Examples 6 to 9.

TABLE 5

| | Example 6 | Example 7 | Example 8 | Example 9 |
|---|---|---|---|---|
| Initial VHR (%) | 99.3 | 99.2 | 99.0 | 99.1 |
| VHR after heating (%) | 98.4 | 98.2 | 98.2 | 98.3 |
| Image sticking | A | A | A | A |
| Volatility | A | A | A | A |
| Process compatibility | A | A | B | A |
| Solubility at low temperature | A | B | A | A |

The structures and combinations described in the embodiments above are merely examples and addition to the structures, omission, substitution, and other modifications are possible without departing from the scope of the present invention. The present invention is not limited to the embodiments and is limited only by the claims.

INDUSTRIAL APPLICABILITY

The liquid crystal composition according to the present invention can be widely applied in fields of liquid crystal display devices and liquid crystal displays.

REFERENCE SIGNS LIST

100 first substrate
102 TFT layer
103 pixel electrode
104 passivation film
105 first alignment film
200 second substrate
201 planarizing film (overcoat layer)
202 black matrix
203 color filter
204 transparent electrode
205 second alignment film
301 sealing material
302 projection (columnar spacer)
303 liquid crystal layer
304 projection (columnar spacer)
401 mask pattern
402 resin layer
L light

The invention claimed is:

1. A liquid crystal composition comprising:
   one or more of compounds represented by general formula (i) below;
   one or more of compounds represented by general formula (ii) below; and
   one or more of compounds represented by general formula (M') below;

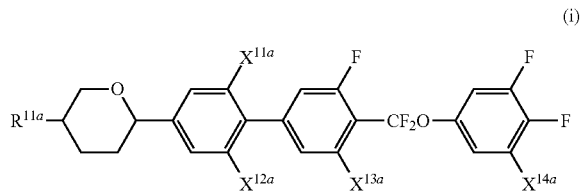

-continued

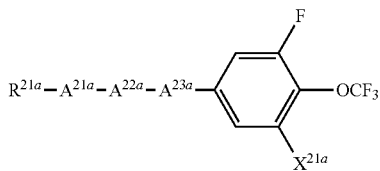
(ii)

in the formulae (i) and (ii), $R^{11a}$ and $R^{21a}$ each independently represent an alkyl group having 1 to 8 carbon atoms where one —$CH_2$— or two or more non-adjacent —$CH_2$— in the alkyl group may each independently be substituted with —CH=CH—, —C≡C—, —O—, —CO—, —COO—, or —OCO—; one or more hydrogen atoms in the alkyl group may be substituted with a fluorine atom or a chlorine atom; $X^{11a}$, $X^{12a}$, $X^{13a}$, $X^{14a}$, and $X^{21a}$ each independently represent a hydrogen atom or a fluorine atom; $A^{21a}$, and $A^{22a}$ each independently represent a trans-1,4-cyclohexylene group or a 1,4-phenylene group whose hydrogen atom may be substituted with a fluorine atom or a chlorine atom; $A^{23a}$ in the general formula (ii) represents a 1,4-phenylene group in which two hydrogen atoms that bond to the 1,4-phenylene group is substituted with fluorine atoms,

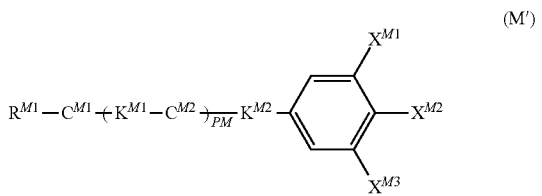
(M')

in the formula (M'), $R^{M1}$ represents an alkyl group having 1 to 8 carbon atoms where one —$CH_2$— or two or more non-adjacent —$CH_2$— in the alkyl group may each independently be substituted with —CH=CH—, —C≡C—, —O—, —CO—, —COO—, or —OCO—;

PM represents 1;

$C^{M1}$ represents a 1,4-cyclohexylene group (one —$CH_2$— or two or more non-adjacent —$CH_2$-present in the group may be substituted with —O— or —S—);

$C^{M2}$ represents a group selected from the group consisting of:
(d) a 1,4-cyclohexylene group (one —$CH_2$— or two or more non-adjacent —$CH_2$— present in the group may be substituted with —O— or —S—) and
(e) a 1,4-phenylene group (one —CH= or two or more non-adjacent —CH= present in the group may be substituted with —N=), where the group (d) and the group (e) may each independently be substituted with a cyano group, a fluorine atom, or a chlorine atom;

$K^{M1}$ and $K^{M2}$ each represent a single bond;

$X^{M1}$ and $X^{M3}$ each independently represent a hydrogen atom, a chlorine atom, or a fluorine atom; and $X^{M2}$ represents a trifluoromethoxy group.

2. The liquid crystal composition according to claim 1, wherein $X^{11a}$ and $X^{12a}$ in the general formula (i) each represent a hydrogen atom.

3. The liquid crystal composition according to claim 1, wherein $X^{13a}$ in the general formula (i) represents a fluorine atom.

4. The liquid crystal composition according to claim 1, wherein $X^{14a}$ in the general formula (i) represents a fluorine atom.

5. The liquid crystal composition according to claim 1, wherein $X^{21a}$ in the general formula (ii) represents a hydrogen atom.

6. The liquid crystal composition according to claim 1, wherein the compounds represented by the general formula (ii) correspond to a compound represented by formula (39.2) below

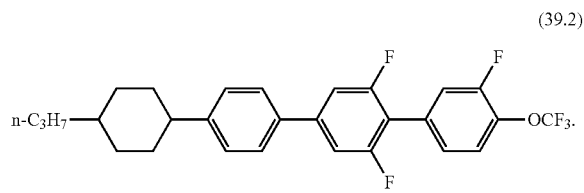
(39.2)

7. The liquid crystal composition according to claim 1, comprising a compound represented by general formula (L) below:

$$R^{L1}-B^{L1}-L^{L1}-B^{L2}-(L^{L2}-B^{L3})_{OL}-R^{L2} \quad (L)$$

(in the formula, $R^{L1}$ and $R^{L2}$ each independently represent an alkyl group having 1 to 8 carbon atoms where one —$CH_2$— or two or more non-adjacent —$CH_2$— in the alkyl group may each independently be substituted with —CH=CH—, —C≡C—, —O—, —CO—, —COO—, or —OCO—;

OL represents 0, 1, 2, or 3;

$B^{L1}$, $B^{L2}$, and $B^{L3}$ each independently represent a group selected from the group consisting of:
(a) a 1,4-cyclohexylene group (one —$CH_2$— or two or more non-adjacent —$CH_2$— present in the group may be substituted with —O—) and
(b) a 1,4-phenylene group (one —CH= or two or more non-adjacent —CH= present in the group may be substituted with —N=), where one or more hydrogen atoms in the group (a) and the group (b) may each independently be substituted with a cyano group, a fluorine atom, or a chlorine atom;

$L^{L1}$ and $L^{L2}$ each independently represent a single bond, —$CH_2CH_2$—, —$(CH_2)_4$—, —$OCH_2$—, —$CH_2O$—, —COO—, —OCO—, —$OCF_2$—, —$CF_2O$—, —CH=N—N=CH—, —CH=CH—, —CF=CF—, or —C≡C—; and when OL represents 2 or 3 and thus a plurality of $L^{L2}$ are present, the plurality of $L^{L2}$ may be the same or different and when OL represents 2 or 3 and thus a plurality of $B^{L3}$ are present, the plurality of $B^{L3}$ may be the same or different.

8. The liquid crystal composition according to claim 1, further comprising a compound represented by general formula (M) below:

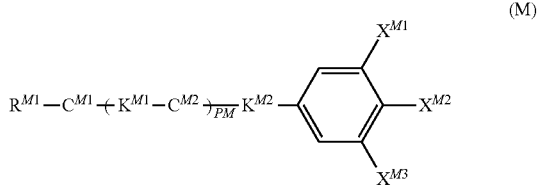
(M)

(in the formula, $R^{M1}$ represents an alkyl group having 1 to 8 carbon atoms where one —$CH_2$— or two or more non-adjacent —CH$_2$— in the alkyl group may each independently be substituted with —CH=CH—, —C≡C—, —O—, —CO—, —COO—, or —OCO—;

PM represents 0, 1, 2, 3, or 4;

C$^{M1}$ and C$^{M2}$ each independently represent a group selected from the group consisting of:

(d) a 1,4-cyclohexylene group (one —CH$_2$— or two or more non-adjacent —CH$_2$— present in the group may be substituted with —O— or —S—) and (e) a 1,4-phenylene group (one —CH= or two or more non-adjacent —CH= present in the group may be substituted with —N=), where one or more hydrogen atoms in the group (d) and the group (e) may each independently be substituted with a cyano group, a fluorine atom, or a chlorine atom;

K$^{M1}$ and K$^{M2}$ each independently represent a single bond, —CH$_2$CH$_2$—, —(CH$_2$)$_4$—, —OCH$_2$—, —CH$_2$O—, —OCF$_2$—, —CF$_2$O—, —COO—, —OCO—, or —C≡C—;

when PM represents 2, 3, or 4 and thus a plurality of K$^{M1}$ are present, the plurality of K$^{M1}$ may be the same or different and when PM represents 2, 3, or 4 and thus a plurality of C$^{M2}$ are present, the plurality of C$^{M2}$ may be the same or different;

X$^{M1}$ and X$^{M3}$ each independently represent a hydrogen atom, a chlorine atom, or a fluorine atom; and X$^{M2}$ represents a hydrogen atom, a fluorine atom, a chlorine atom, a cyano group, a trifluoromethyl group, a fluoromethoxy group, a difluoromethoxy group, a trifluoromethoxy group, or a 2,2,2-trifluoroethyl group, the compound represented by the general formula (M) excluding the compounds represented by the general formula (M'), the compounds represented by the general formula (i), and the compounds represented by the general formula (ii).

9. The liquid crystal composition according to claim 1, further comprising a compound represented by formula (1.3) below.

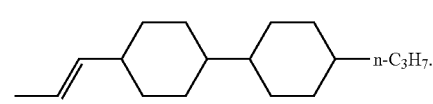

(1.3)

10. A liquid crystal display device using the liquid crystal composition according to claim 1.

11. A liquid crystal display device for an IPS mode, an OCB mode, an ECB mode, a VA mode, a VA-IPS mode, or an FFS mode, the liquid crystal display device using the liquid crystal composition according to claim 1.

12. The liquid crystal composition according to claim 1, wherein as said one or more of the compounds represented by general formula (i), the liquid crystal composition comprises both compounds represented by formulae (44.1) and (44.2):

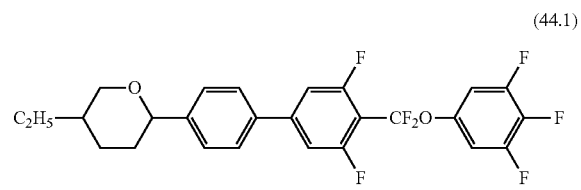

(44.1)

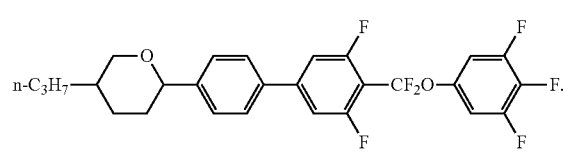

(44.2)

13. The liquid crystal composition according to claim 12, wherein X$^{21a}$ in the general formula (ii) represents a hydrogen atom.

14. The liquid crystal composition according to claim 12, wherein the compounds represented by the general formula (ii) correspond to a compound represented by formula (39.2) below

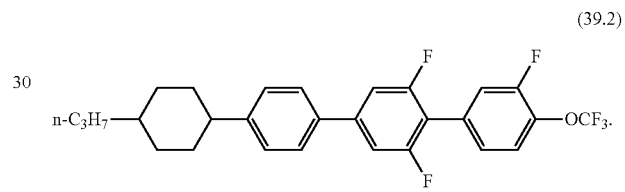

(39.2)

15. The liquid crystal composition according to claim 1, further comprising a compound represented by formula (11.1):

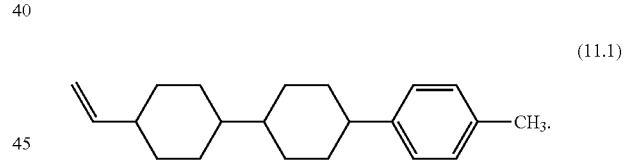

(11.1)

16. The liquid crystal composition according to claim 12, wherein two or more of said compounds represented by general formula (i) are included in the liquid crystal composition.

17. The liquid crystal composition according to claim 1, wherein all of intermolecular ring structures included in the liquid crystal composition are six-membered ring.

* * * * *